US012753217B2

(12) United States Patent
Gorby et al.

(10) Patent No.: US 12,753,217 B2
(45) Date of Patent: Oct. 6, 2026

(54) IL-10 MUTEINS

(71) Applicants: University of Dundee, Dundee (GB); INSERM (Institut National de la Santé et de la Recherche Médicale), Paris (FR); Université de Lille, Lille (FR); Centre Hospitalier Régional Universitaire de Lille, Lille (FR)

(72) Inventors: Claire Gorby, Dundee (GB); Ignacio Moraga Gonzalez, Dundee (GB); Suman Mitra, Lille Cedex (FR)

(73) Assignees: Université de Lille, Lille (FR); University of Dundee, Dundee (GB)

( * ) Notice: Subject to any disclaimer, the term of this patent is extended or adjusted under 35 U.S.C. 154(b) by 859 days.

(21) Appl. No.: 17/910,720

(22) PCT Filed: Mar. 10, 2021

(86) PCT No.: PCT/GB2021/050592
§ 371 (c)(1),
(2) Date: Sep. 9, 2022

(87) PCT Pub. No.: WO2021/181091
PCT Pub. Date: Sep. 16, 2021

(65) Prior Publication Data

US 2023/0203117 A1 Jun. 29, 2023

(30) Foreign Application Priority Data

Mar. 10, 2020 (GB) ...................................... 2003428

(51) Int. Cl.
*A61K 38/20* (2006.01)
*A61P 37/02* (2006.01)
*C07K 14/54* (2006.01)

(52) U.S. Cl.
CPC .......... *C07K 14/5428* (2013.01); *A61P 37/02* (2018.01); *C07K 14/5406* (2013.01); *C07K 2319/30* (2013.01)

(58) Field of Classification Search
CPC .......................... C07K 14/5428; A61K 38/204
See application file for complete search history.

(56) References Cited

U.S. PATENT DOCUMENTS

| | | | |
|---|---|---|---|
| 10,851,143 | B2 | 12/2020 | Van Roon et al. |
| 2016/0068583 | A1 | 3/2016 | Van Vlasselaer et al. |

FOREIGN PATENT DOCUMENTS

| | | | |
|---|---|---|---|
| EP | 0 405 980 | A1 | 1/1991 |
| WO | 9100349 | A1 | 1/1991 |
| WO | 2013/070076 | A1 | 5/2013 |
| WO | 2014/023673 | A1 | 2/2014 |
| WO | 2014/176373 | A2 | 10/2014 |
| WO | WO 2015/070060 | A1 | 5/2015 |
| WO | WO 2020/082057 | A1 | 4/2020 |

OTHER PUBLICATIONS

Bork. Powers and Pitfalls in Sequence Analysis: The 70% Hurdle. Genome Research, 2000, 10:398-400 (Year: 2000).*

Greenspan et al. 1999. Defining epitopes: It's not as easy as it seems; Nature Biotechnology, 17:936-937 (Year: 1999).*

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

Asadullah et al., "Interleukin-10 therapy: Review of a new approach", *Pharmacol Rev.*, 55(2); pp. 241-269, (2003).

Josephson et al., "Design and analysis of an engineered human interleukin-10 monomer", *J Biol Chem*, 275, pp. 13552-13557, (2000).

Mendoza et al., "The IFN-lambda-IFN-lambda R1-IL-10R beta Complex Reveals Structural Features Underlying Type III IFN Functional Plasticity", *Immunity*, 46(3), pp. 379-392, (2017).

Steen-Louws et al., "IL4-10 fusion protein: a novel immunoregulatory drug combining activities of interleukin 4 and interleukin 10", *Clinical & Experimental Immunology*, 195(1), pp. 1-9, (2019).

Yoon et al., "Conformational Changes Mediate Interleukin-10 Receptor 2 (IL-10R2) Binding to IL-10 and Assembly of the Signaling Complex," The Journal of Biological Chemistry, vol. 281, No. 46, p. 35088-35096, (2006).

* cited by examiner

*Primary Examiner* — Prema M Mertz
(74) *Attorney, Agent, or Firm* — Hoxie & Associates LLC

(57) ABSTRACT

The present disclosure relates to modified forms, or muteins, of IL-10, as well as variants thereof, which display improved features as compared to wild-type IL-10. The present invention further relates to the use of such modified forms, or muteins, of IL-10, as well as variants thereof in methods, including therapeutic methods.

16 Claims, 61 Drawing Sheets

Specification includes a Sequence Listing.

Figure 1A:
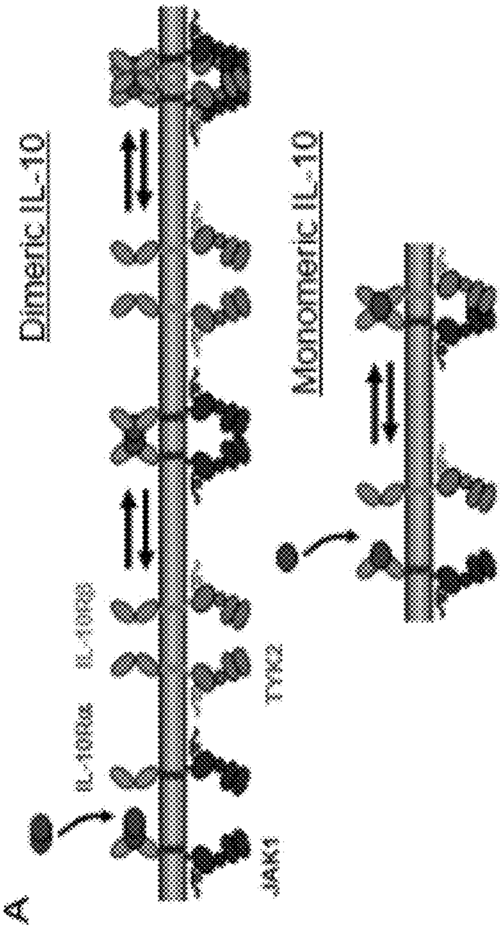
Figure 1B:
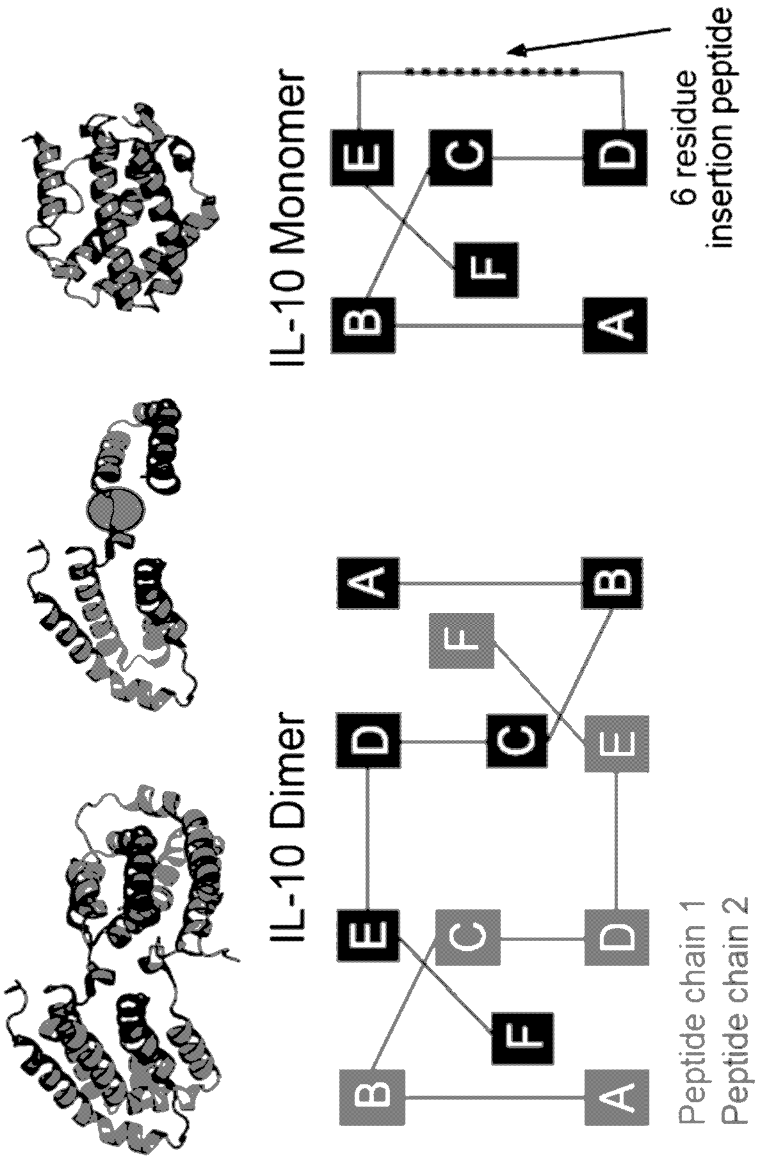
Figure 1D:
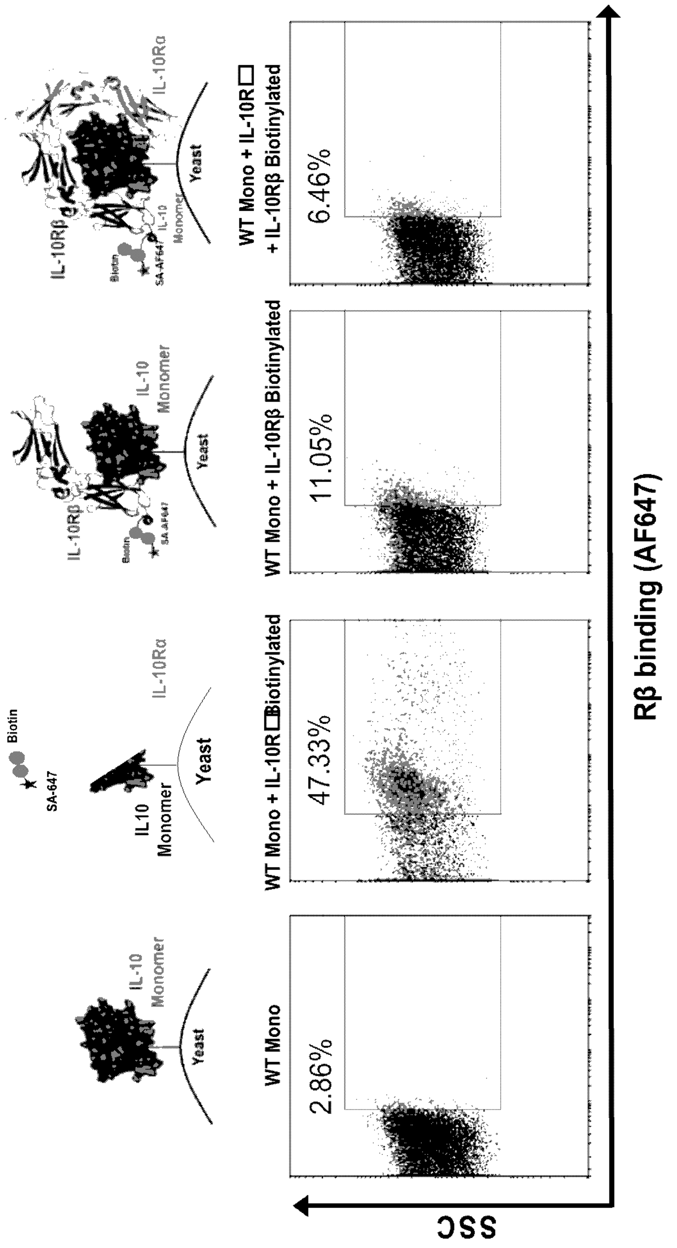
Figure 1E:
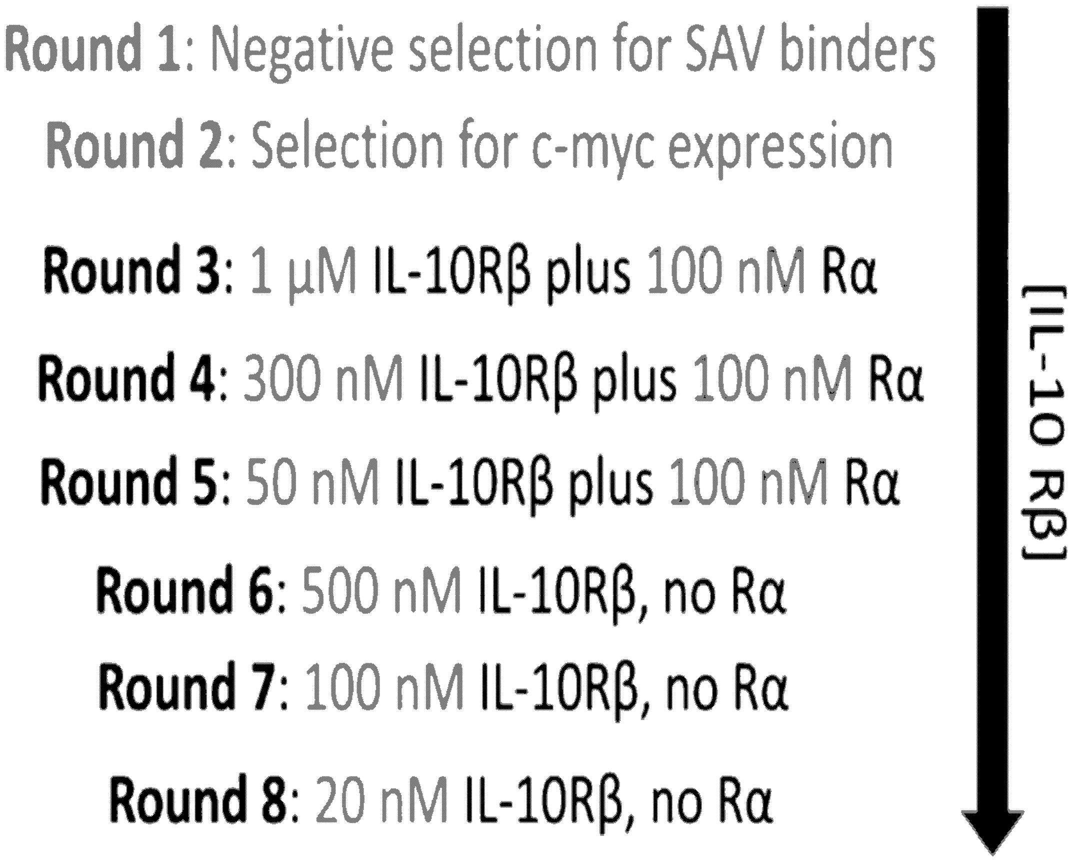
Figure 1:
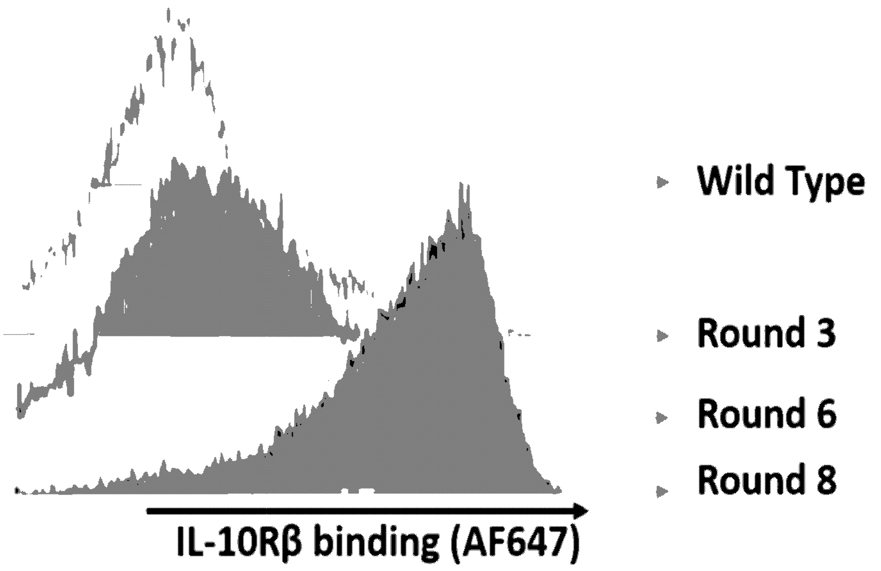

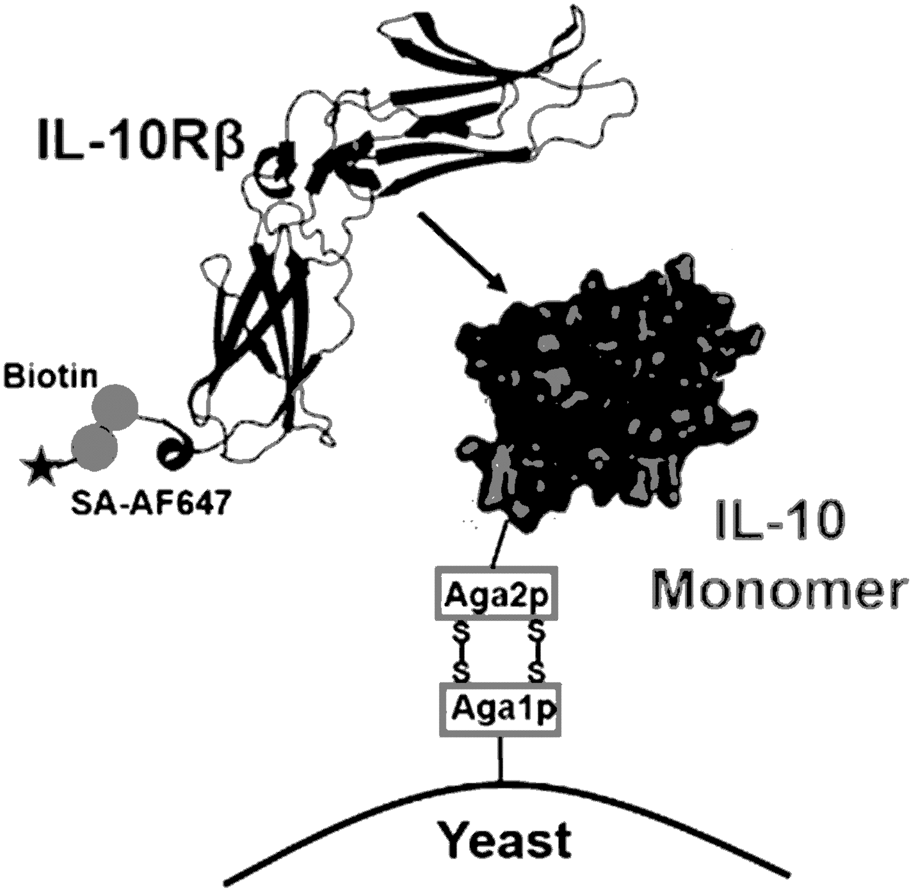
Figure 1 (C

| WT | N18 | D55 | I69 | N92 | N97 | K99 | R110 | F111 | N148 |
|---|---|---|---|---|---|---|---|---|---|
| A11 | Y | | | I | | N | | | H |
| B11 | Y | V | M | I | K | | W | | |
| R5A11 | I | | | I | | N | | L | |
| G3 | Y | V | M | I | | N | W | | |

On-yeast dose response

IL-10:IL-10Rβ binding

| Protein (Monomer) | $K_D$ (μM) |
|---|---|
| WT | ND |
| A11 | 2.4 |
| B11 | 9.4 |
| R5A11 | 8.9 |
| G3 | 2.4 |

IL-10/IL-10Rα:IL-10Rβ binding

| Protein (Monomer) | $K_D$ (μM) |
|---|---|
| WT (+Rα) | ND |
| A11 (+Rα) | 0.023 |
| B11 (+Rα) | 0.065 |
| R5A11 (+Rα) | 0.1 |
| G3 (+Rα) | 0.008 |

Biacore

SEQUENCE LISTING

```
<160> NUMBER OF SEQ ID NOS: 24

<210> SEQ ID NO 1
<211> LENGTH: 178
<212> TYPE: PRT
<213> ORGANISM: Artificial Sequence
<220> FEATURE:
<223> OTHER INFORMATION: Wild type dimeric IL-10

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 2
<211> LENGTH: 534
<212> TYPE: DNA
<213> ORGANISM: Artificial Sequence
<220> FEATURE:
<223> OTHER INFORMATION: Wild type dimeric IL-10

<400> SEQUENCE: 2

atgcacagct cagcactgct ctgttgcctg gtcctcctga ctggggtgag ggccagccca      60

ggccagggca cccagtccga gaacagttgc acgcactttc cgggcaacct tcctaacatg     120

cttcgcgacc tgcgagatgc gttctctcga gtgaaaactt tctttcagat gaaagatcag     180

ttggataatt tgctcctcaa ggagtccctt ctcgaagact ttaaaggata cctggggtgc     240

caggcgctta gcgagatgat acagttctat ctggaggaag tgatgcccca agcagaaaat     300

caagatcccg atattaaggc ccatgtcaac agccttggcg aaaatttgaa aactctcaga     360
```

ctccgacttc gccgatgcca caggtttttg ccatgtgaga ataagtccaa ggccgttgag 420
caggtgaaaa acgctttcaa caaactgcaa gaaaagggga tctacaaagc gatgtcagag 480
ttcgacatat ttataaacta catagaagcc tatatgacga tgaaaatccg caac 534

<210> SEQ ID NO 3
<211> LENGTH: 184
<212> TYPE: PRT
<213> ORGANISM: Artificial Sequence
<220> FEATURE:
<223> OTHER INFORMATION: Wild type dimeric IL-10

<400> SEQUENCE: 3

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Gly Gly Gly Ser Gly Gly Lys Ser Lys Ala
    130                 135                 140

Val Glu Gln Val Lys Asn Ala Phe Asn Lys Leu Gln Glu Lys Gly Ile
145                 150                 155                 160

Tyr Lys Ala Met Ser Glu Phe Asp Ile Phe Ile Asn Tyr Ile Glu Ala
                165                 170                 175

Tyr Met Thr Met Lys Ile Arg Asn
            180
```

<210> SEQ ID NO 4
<211> LENGTH: 552
<212> TYPE: DNA
<213> ORGANISM: Artificial Sequence
<220> FEATURE:
<223> OTHER INFORMATION: Wild type monomeric IL-10

<400> SEQUENCE: 4
atgcacagct cagcactgct ctgttgcctg gtcctcctga ctggggtgag ggccagccca 60
ggccagggca cccagtccga gaacagttgc acgcactttc cgggcaacct tcctaacatg 120
cttcgcgacc tgcgagatgc gttctctcga gtgaaaactt tctttcagat gaaagatcag 180
ttggataatt tgctcctcaa ggagtccctt ctcgaagact ttaaaggata cctggggtgc 240
caggcgctta gcgagatgat acagttctat ctggaggaag tgatgcccca agcagaaaat 300
caagatcccg atattaaggc ccatgtcaac agccttggcg aaaatttgaa aactctcaga 360
ctccgacttc gccgatgcca caggtttttg ccatgtgaga atgggggtgg ttccgggggt 420
aagtccaagg ccgttgagca ggtgaaaaac gctttcaaca aactgcaaga aaaggggatc 480
tacaaagcga tgtcagagtt cgacatattt ataaactaca tagaagccta tatgacgatg 540
aaaatccgca ac 552

<210> SEQ ID NO 5
<211> LENGTH: 178
<212> TYPE: PRT
<213> ORGANISM: Artificial Sequence
<220> FEATURE:
<223> OTHER INFORMATION: A11 dimer mutein

<400> SEQUENCE: 5

Met His Ser Ser Ala Leu Leu Cys Cys Leu Val Leu Leu Thr Gly Val
1 5 10 15

Arg Ala Ser Pro Gly Gln Gly Thr Gln Ser Glu Asn Ser Cys Thr His
20 25 30

Phe Pro Gly Tyr Leu Pro Asn Met Leu Arg Asp Leu Arg Asp Ala Phe
35 40 45

Ser Arg Val Lys Thr Phe Phe Gln Met Lys Asp Gln Leu Asp Asn Leu
50 55 60

Leu Leu Lys Glu Ser Leu Leu Glu Asp Phe Lys Gly Tyr Leu Gly Cys
65 70 75 80

Gln Ala Leu Ser Glu Met Ile Gln Phe Tyr Leu Glu Glu Val Met Pro
85 90 95

Gln Ala Glu Asn Gln Asp Pro Asp Ile Lys Ala His Val Ile Ser Leu
100 105 110

Gly Glu Asn Leu Asn Thr Leu Arg Leu Arg Leu Arg Arg Cys His Arg
115 120 125

Phe Leu Pro Cys Glu Asn Lys Ser Lys Ala Val Glu Gln Val Lys Asn
130 135 140

Ala Phe Asn Lys Leu Gln Glu Lys Gly Ile Tyr Lys Ala Met Ser Glu
145 150 155 160

Phe Asp Ile Phe Ile His Tyr Ile Glu Ala Tyr Met Thr Met Lys Ile
165 170 175

Arg Asn

<210> SEQ ID NO 6
<211> LENGTH: 534
<212> TYPE: DNA
<213> ORGANISM: Artificial Sequence
<220> FEATURE:
<223> OTHER INFORMATION: A11 dimer mutein

<400> SEQUENCE: 6
atgcacagct cagcactgct ctgttgcctg gtcctcctga ctggggtgag ggccagccca 60
ggccagggca cccagtccga gaacagttgc acgcactttc cgggctacct tcctaacatg 120
cttcgcgacc tgcgagatgc gttctctcga gtgaaaactt tctttcagat gaaagatcag 180
ttggataatt tgctcctcaa ggagtccctt ctcgaagact ttaaaggata cctggggtgc 240
caggcgctta gcgagatgat acagttctat ctggaggaag tgatgcccca agcagaaaat 300
caagatcccg atattaaggc ccatgtcatc agccttggcg aaaatttgaa cactctcaga 360
ctccgacttc gccgatgcca caggtttttg ccatgtgaga ataagtccaa ggccgttgag 420
caggtgaaaa acgctttcaa caaactgcaa gaaaagggga tctacaaagc gatgtcagag 480
ttcgacatat ttatacacta catagaagcc tatatgacga tgaaaatccg caac 534

<210> SEQ ID NO 7

<211> LENGTH: 178
<212> TYPE: PRT
<213> ORGANISM: Artificial Sequence
<220> FEATURE:
<223> OTHER INFORMATION: B11 dimer mutein

<400> SEQUENCE: 7

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Tyr Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Val Phe Lys Gly Tyr Leu Gly Cys
65                  70                  75                  80

Gln Ala Leu Ser Glu Met Met Gln Phe Tyr Leu Glu Glu Val Met Pro
                85                  90                  95

Gln Ala Glu Asn Gln Asp Pro Asp Ile Lys Ala His Val Ile Ser Leu
            100                 105                 110

Gly Glu Lys Leu Lys Thr Leu Arg Leu Arg Leu Arg Arg Cys His Trp
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 8
<211> LENGTH: 534
<212> TYPE: DNA
<213> ORGANISM: Artificial Sequence
<220> FEATURE:
<223> OTHER INFORMATION: B11 dimer mutein

<400> SEQUENCE: 8

```
atgcacagct cagcactgct ctgttgcctg gtcctcctga ctggggtgag ggccagccca      60

ggccagggca cccagtccga gaacagttgc acgcactttc cgggctacct tcctaacatg     120

cttcgcgacc tgcgagatgc gttctctcga gtgaaaactt tctttcagat gaaagatcag     180

ttggataatt tgctcctcaa ggagtccctt ctcgaagtct ttaaaggata cctggggtgc     240

caggcgctta gcgagatgat gcagttctat ctggaggaag tgatgcccca agcagaaaat     300

caagatcccg atattaaggc ccatgtcatc agccttggcg aaaagttgaa aactctcaga     360

ctccgacttc gccgatgcca ctggtttttg ccatgtgaga ataagtccaa ggccgttgag     420

caggtgaaaa acgctttcaa caaactgcaa gaaaagggga tctacaaagc gatgtcagag     480

ttcgacatat ttataaacta catagaagcc tatatgacga tgaaaatccg caac           534
```

<210> SEQ ID NO 9
<211> LENGTH: 184
<212> TYPE: PRT
<213> ORGANISM: Artificial Sequence
<220> FEATURE:
<223> OTHER INFORMATION: R5A11 monomer mutein

<400> SEQUENCE: 9

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Ile Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Ile Ser Leu
            100                 105                 110

Gly Glu Asn Leu Asn Thr Leu Arg Leu Arg Leu Arg Arg Cys His Arg
        115                 120                 125

Leu Leu Pro Cys Glu Asn Gly Gly Gly Ser Gly Gly Lys Ser Lys Ala
    130                 135                 140

Val Glu Gln Val Lys Asn Ala Phe Asn Lys Leu Gln Glu Lys Gly Ile
145                 150                 155                 160

Tyr Lys Ala Met Ser Glu Phe Asp Ile Phe Ile Asn Tyr Ile Glu Ala
                165                 170                 175

Tyr Met Thr Met Lys Ile Arg Asn
            180
```

<210> SEQ ID NO 10
<211> LENGTH: 552
<212> TYPE: DNA
<213> ORGANISM: Artificial Sequence
<220> FEATURE:
<223> OTHER INFORMATION: R5A11 monomer mutein

<400> SEQUENCE: 10

```
atgcacagct cagcactgct ctgttgcctg gtcctcctga ctggggtgag ggccagccca     60

ggccagggca cccagtccga gaacagttgc acgcactttc cgggcatcct tcctaacatg    120

cttcgcgacc tgcgagatgc gttctctcga gtgaaaactt tctttcagat gaaagatcag    180

ttggataatt tgctcctcaa ggagtccctt ctcgaagact ttaaaggata cctggggtgc    240

caggcgctta gcgagatgat acagttctat ctggaggaag tgatgcccca agcagaaaat    300

caagatcccg atattaaggc ccatgtcatc agccttggcg aaaatttgaa tactctcaga    360

ctccgacttc gccgatgcca caggcttttg ccatgtgaga atgggggtgg ttccgggggt    420

aagtccaagg ccgttgagca ggtgaaaaac gctttcaaca aactgcaaga aaaggggatc    480

tacaaagcga tgtcagagtt cgacatattt ataaactaca tagaagccta tatgacgatg    540

aaaatccgca ac                                                        552
```

<210> SEQ ID NO 11
<211> LENGTH: 178
<212> TYPE: PRT
<213> ORGANISM: Artificial Sequence
<220> FEATURE:
<223> OTHER INFORMATION: R5A11 dimer mutein

<400> SEQUENCE: 11

```
Met His Ser Ser Ala Leu Leu Cys Cys Leu Val Leu Leu Thr Gly Val
```

```
1               5                   10                  15

Arg Ala Ser Pro Gly Gln Gly Thr Gln Ser Glu Asn Ser Cys Thr His
            20                  25                  30

Phe Pro Gly Ile Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Ile Ser Leu
            100                 105                 110

Gly Glu Asn Leu Asn Thr Leu Arg Leu Arg Leu Arg Arg Cys His Arg
        115                 120                 125

Leu Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 12
<211> LENGTH: 534
<212> TYPE: DNA
<213> ORGANISM: Artificial Sequence
<220> FEATURE:
<223> OTHER INFORMATION: R5A11 dimer mutein

<400> SEQUENCE: 12

```
atgcacagct cagcactgct ctgttgcctg gtcctcctga ctggggtgag ggccagccca     60

ggccagggca cccagtccga gaacagttgc acgcactttc cgggcatcct tcctaacatg    120

cttcgcgacc tgcgagatgc gttctctcga gtgaaaactt tctttcagat gaaagatcag    180

ttggataatt tgctcctcaa ggagtccctt ctcgaagact ttaaaggata cctggggtgc    240

caggcgctta gcgagatgat acagttctat ctggaggaag tgatgcccca agcagaaaat    300

caagatcccg atattaaggc ccatgtcatc agccttggcg aaaatttgaa tactctcaga    360

ctccgacttc gccgatgcca caggcttttg ccatgtgaga ataagtccaa ggccgttgag    420

caggtgaaaa acgctttcaa caaactgcaa gaaaagggga tctacaaagc gatgtcagag    480

ttcgacatat ttataaacta catagaagcc tatatgacga tgaaaatccg caac          534
```

<210> SEQ ID NO 13
<211> LENGTH: 184
<212> TYPE: PRT
<213> ORGANISM: Artificial Sequence
<220> FEATURE:
<223> OTHER INFORMATION: G3 monomer mutein

<400> SEQUENCE: 13

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Tyr Leu Pro Asn Met Leu Arg Asp Leu Arg Asp Ala Phe
```

```
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Val Phe Lys Gly Tyr Leu Gly Cys
65                  70                  75                  80

Gln Ala Leu Ser Glu Met Met Gln Phe Tyr Leu Glu Glu Val Met Pro
                85                  90                  95

Gln Ala Glu Asn Gln Asp Pro Asp Ile Lys Ala His Val Ile Ser Leu
            100                 105                 110

Gly Glu Asn Leu Asn Thr Leu Arg Leu Arg Leu Arg Arg Cys His Trp
        115                 120                 125

Phe Leu Pro Cys Glu Asn Gly Gly Gly Ser Gly Gly Lys Ser Lys Ala
    130                 135                 140

Val Glu Gln Val Lys Asn Ala Phe Asn Lys Leu Gln Glu Lys Gly Ile
145                 150                 155                 160

Tyr Lys Ala Met Ser Glu Phe Asp Ile Phe Ile Asn Tyr Ile Glu Ala
                165                 170                 175

Tyr Met Thr Met Lys Ile Arg Asn
            180


<210> SEQ ID NO 14
<211> LENGTH: 552
<212> TYPE: DNA
<213> ORGANISM: Artificial Sequence
<220> FEATURE:
<223> OTHER INFORMATION: G3 monomer mutein

<400> SEQUENCE: 14

atgcacagct cagcactgct ctgttgcctg gtcctcctga ctggggtgag ggccagccca     60

ggccagggca cccagtccga gaacagttgc acgcactttc cgggctacct tcctaacatg    120

cttcgcgacc tgcgagatgc gttctctcga gtgaaaactt tctttcagat gaaagatcag    180

ttggataatt tgctcctcaa ggagtccctt ctcgaagtct ttaaaggata cctggggtgc    240

caggcgctta gcgagatgat gcagttctat ctggaggaag tgatgcccca agcagaaaat    300

caagatcccg atattaaggc ccatgtcatc agccttggcg aaaatttgaa cactctcaga    360

ctccgacttc gccgatgcca ctggtttttg ccatgtgaga atgggggtgg ttccgggggt    420

aagtccaagg ccgttgagca ggtgaaaaac gctttcaaca aactgcaaga aaaggggatc    480

tacaaagcga tgtcagagtt cgacatattt ataaactaca tagaagccta tatgacgatg    540

aaaatccgca ac                                                         552


<210> SEQ ID NO 15
<211> LENGTH: 178
<212> TYPE: PRT
<213> ORGANISM: Artificial Sequence
<220> FEATURE:
<223> OTHER INFORMATION: G3 dimer mutein

<400> SEQUENCE: 15

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Tyr Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
```

```
    50                  55                  60

Leu Leu Lys Glu Ser Leu Leu Glu Val Phe Lys Gly Tyr Leu Gly Cys
65                  70                  75                  80

Gln Ala Leu Ser Glu Met Met Gln Phe Tyr Leu Glu Glu Val Met Pro
                85                  90                  95

Gln Ala Glu Asn Gln Asp Pro Asp Ile Lys Ala His Val Ile Ser Leu
            100                 105                 110

Gly Glu Asn Leu Asn Thr Leu Arg Leu Arg Leu Arg Arg Cys His Trp
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 16
<211> LENGTH: 534
<212> TYPE: DNA
<213> ORGANISM: Artificial Sequence
<220> FEATURE:
<223> OTHER INFORMATION: G3 dimer mutein

<400> SEQUENCE: 16

atgcacagct cagcactgct ctgttgcctg gtcctcctga ctggggtgag ggccagccca     60

ggccagggca cccagtccga gaacagttgc acgcactttc cgggctacct tcctaacatg    120

cttcgcgacc tgcgagatgc gttctctcga gtgaaaactt tctttcagat gaaagatcag    180

ttggataatt tgctcctcaa ggagtccctt ctcgaagtct ttaaaggata cctggggtgc    240

caggcgctta gcgagatgat gcagttctat ctggaggaag tgatgcccca agcagaaaat    300

caagatcccg atattaaggc ccatgtcatc agccttggcg aaaatttgaa tactctcaga    360

ctccgacttc gccgatgcca ctggtttttg ccatgtgaga ataagtccaa ggccgttgag    420

caggtgaaaa acgctttcaa caaactgcaa gaaaagggga tctacaaagc gatgtcagag    480

ttcgacatat ttataaacta catagaagcc tatatgacga tgaaaatccg caac          534


<210> SEQ ID NO 17
<211> LENGTH: 302
<212> TYPE: PRT
<213> ORGANISM: Artificial Sequence
<220> FEATURE:
<223> OTHER INFORMATION: IL-10 pentameric variant

<400> SEQUENCE: 17

Gly Leu Asn Asp Ile Phe Glu Ala Gln Lys Ile Glu Trp His Glu Gly
1               5                   10                  15

Gly Ser Phe His Thr Asp Trp Leu Thr Leu Asn Val Gly Gly Arg Tyr
            20                  25                  30

Phe Thr Thr Thr Arg Ser Thr Leu Val Asn Lys Glu Pro Asp Ser Met
        35                  40                  45

Leu Ala His Met Phe Lys Asp Lys Gly Val Trp Gly Asn Lys Gln Asp
    50                  55                  60

His Arg Gly Ala Phe Leu Ile Asp Arg Ser Pro Glu Tyr Phe Glu Pro
65                  70                  75                  80

Ile Leu Asn Tyr Leu Arg His Gly Gln Leu Ile Val Asn Asp Gly Ile
```

```
                85                  90                  95

Asn Leu Leu Gly Val Leu Glu Glu Ala Arg Phe Phe Gly Ile Asp Ser
            100                 105                 110

Leu Ile Glu His Leu Glu Val Ala Ile Lys Asn Ser Gly Ser Gly Gly
        115                 120                 125

Ser Gly Ser Gly Gly Gly Gly Ser Gly Gly Gly Gly Ser Gly Ser Ser
    130                 135                 140

Glu Asn Ser Cys Thr His Phe Pro Gly Ile Leu Pro Asn Met Leu Arg
145                 150                 155                 160

Asp Leu Arg Asp Ala Phe Ser Arg Val Lys Thr Phe Phe Gln Met Lys
                165                 170                 175

Asp Gln Leu Asp Asn Leu Leu Leu Lys Glu Ser Leu Leu Glu Asp Phe
            180                 185                 190

Lys Gly Tyr Leu Gly Cys Gln Ala Leu Ser Glu Met Ile Gln Phe Tyr
        195                 200                 205

Leu Glu Glu Val Met Pro Gln Ala Glu Asn Gln Asp Pro Asp Ile Lys
    210                 215                 220

Ala His Val Ile Ser Leu Gly Glu Asn Leu Asn Thr Leu Arg Leu Arg
225                 230                 235                 240

Leu Arg Arg Cys His Arg Leu Leu Pro Cys Glu Asn Gly Gly Gly Ser
                245                 250                 255

Gly Gly Lys Ser Lys Ala Val Glu Gln Val Lys Asn Ala Phe Asn Lys
            260                 265                 270

Leu Gln Glu Lys Gly Ile Tyr Lys Ala Met Ser Glu Phe Asp Ile Phe
        275                 280                 285

Ile Asn Tyr Ile Glu Ala Tyr Met Thr Met Lys Ile Arg Asn
    290                 295                 300
```

<210> SEQ ID NO 18
<211> LENGTH: 906
<212> TYPE: DNA
<213> ORGANISM: Artificial Sequence
<220> FEATURE:
<223> OTHER INFORMATION: Il-10 pentameric variant

<400> SEQUENCE: 18

```
ggtctgaacg acatcttcga ggctcagaaa atcgaatggc acgaaggtgg aagtttccac      60

acagactggc tgacattaaa tgttggaggg cggtacttta caactacacg gagcacttta     120

gtgaataaag aacctgacag tatgctggcc cacatgttta aggacaaagg tgtctgggga     180

aataagcaag atcatagagg agctttctta attgaccgaa gtcctgagta cttcgaaccc     240

attttgaact acttgcgtca tggacagctc attgtaaatg atggcattaa tttattgggt     300

gtgttagaag aagcaagatt ttttggtatt gactcattga ttgaacacct agaagtggca     360

ataaagaatt ctggttcagg tggaagtggc agcggcggtg gtggttccgg aggcggcggt     420

tctggatcct ccgagaacag ttgcacgcac tttccgggca tccttcctaa catgcttcgc     480

gacctgcgag atgcgttctc tcgagtgaaa actttctttc agatgaaaga tcagttggat     540

aatttgctcc tcaaggagtc ccttctcgaa gactttaaag gatacctggg gtgccaggcg     600

cttagcgaga tgatacagtt ctatctggag gaagtgatgc cccaagcaga aaatcaagat     660

cccgatatta aggcccatgt catcagcctt ggcgaaaatt tgaatactct cagactccga     720

cttcgccgat gccacaggct tttgccatgt gagaatgggg gtggttccgg gggtaagtcc     780

aaggccgttg agcaggtgaa aaacgctttc aacaaactgc aagaaaaggg gatctacaaa     840
```

gcgatgtcag agttcgacat atttataaac tacatagaag cctatatgac gatgaaaatc 900
cgcaac 906

<210> SEQ ID NO 19
<211> LENGTH: 308
<212> TYPE: PRT
<213> ORGANISM: Artificial Sequence
<220> FEATURE:
<223> OTHER INFORMATION: R5A11-IL4

<400> SEQUENCE: 19

Ser Glu Asn Ser Cys Thr His Phe Pro Gly Ile Leu Pro Asn Met Leu
1 5 10 15

Arg Asp Leu Arg Asp Ala Phe Ser Arg Val Lys Thr Phe Phe Gln Met
20 25 30

Lys Asp Gln Leu Asp Asn Leu Leu Leu Lys Glu Ser Leu Leu Glu Asp
35 40 45

Phe Lys Gly Tyr Leu Gly Cys Gln Ala Leu Ser Glu Met Ile Gln Phe
50 55 60

Tyr Leu Glu Glu Val Met Pro Gln Ala Glu Asn Gln Asp Pro Asp Ile
65 70 75 80

Lys Ala His Val Ile Ser Leu Gly Glu Asn Leu Asn Thr Leu Arg Leu
85 90 95

Arg Leu Arg Arg Cys His Arg Leu Leu Pro Cys Glu Asn Gly Gly Gly
100 105 110

Ser Gly Gly Lys Ser Lys Ala Val Glu Gln Val Lys Asn Ala Phe Asn
115 120 125

Lys Leu Gln Glu Lys Gly Ile Tyr Lys Ala Met Ser Glu Phe Asp Ile
130 135 140

Phe Ile Asn Tyr Ile Glu Ala Tyr Met Thr Met Lys Ile Arg Asn Gly
145 150 155 160

Ile Leu Gly Ser Gly Gly Gly Gly Ser Gly Gly Gly Gly Ser Gly Gly
165 170 175

Gly Gly Ser His Lys Cys Asp Ile Thr Leu Gln Glu Ile Ile Lys Thr
180 185 190

Leu Asn Ser Leu Thr Glu Gln Lys Thr Leu Cys Thr Glu Leu Thr Val
195 200 205

Thr Asp Ile Phe Ala Ala Ser Lys Asn Thr Thr Glu Lys Glu Thr Phe
210 215 220

Cys Arg Ala Ala Thr Val Leu Arg Gln Phe Tyr Ser His His Glu Lys
225 230 235 240

Asp Thr Arg Cys Leu Gly Ala Thr Ala Gln Gln Phe His Arg His Lys
245 250 255

Gln Leu Ile Arg Phe Leu Lys Arg Leu Asp Arg Asn Leu Trp Gly Leu
260 265 270

Ala Gly Leu Asn Ser Cys Pro Val Lys Glu Ala Asn Gln Ser Thr Leu
275 280 285

Glu Asn Phe Leu Glu Arg Leu Lys Thr Ile Met Arg Glu Lys Tyr Ser
290 295 300

Lys Cys Ser Ser
305

<210> SEQ ID NO 20
<211> LENGTH: 924
<212> TYPE: DNA
<213> ORGANISM: Artificial Sequence

<220> FEATURE:
<223> OTHER INFORMATION: R5A11-IL4

<400> SEQUENCE: 20
tccgagaaca gttgcacgca ctttccgggc atccttccta acatgcttcg cgacctgcga 60
gatgcgttct ctcgagtgaa aactttcttt cagatgaaag atcagttgga taatttgctc 120
ctcaaggagt cccttctcga agactttaaa ggatacctgg ggtgccaggc gcttagcgag 180
atgatacagt tctatctgga ggaagtgatg ccccaagcag aaaatcaaga tcccgatatt 240
aaggcccatg tcatcagcct tggcgaaaat ttgaatactc tcagactccg acttcgccga 300
tgccacaggc ttttgccatg tgagaatggg ggtggttccg gggtaagtc caaggccgtt 360 gagcaggtga aaaacgcttt caacaaactg caagaaaagg ggatctacaa agcgatgtca 420
gagttcgaca tatttataaa ctacatagaa gcctatatga cgatgaaaat ccgcaacgga 480
attctaggtt ccggtggcgg tggcagcggc ggtggtggtt ccgggggcgg cggttctcac 540
aagtgcgata tcaccttaca ggagatcatc aaaactttga acagcctcac agagcagaag 600
actctgtgca ccgagttgac cgtaacagac atctttgctg cctccaagaa cacaactgag 660
aaggaaacct tctgcagggc tgcgactgtg ctccggcagt tctacagcca ccatgagaag 720
gacactcgct gcctgggtgc gactgcacag cagttccaca ggcacaagca gctgatccga 780
ttcctgaaac ggctcgacag gaacctctgg ggcctggcgg gcttgaattc ctgtcctgtg 840
aaggaagcca accagagtac gttggaaaac ttcttggaaa ggctaaagac gatcatgaga 900
gagaaatatt caaagtgttc gagc 924

<210> SEQ ID NO 21
<211> LENGTH: 307
<212> TYPE: PRT
<213> ORGANISM: Artificial Sequence
<220> FEATURE:
<223> OTHER INFORMATION: R5A11-IL4 (Q8A/R121A/Y124A)

<400> SEQUENCE: 21

Glu Asn Ser Cys Thr His Phe Pro Gly Ile Leu Pro Asn Met Leu Arg
1 5 10 15

Asp Leu Arg Asp Ala Phe Ser Arg Val Lys Thr Phe Phe Gln Met Lys
20 25 30

Asp Gln Leu Asp Asn Leu Leu Leu Lys Glu Ser Leu Leu Glu Asp Phe
35 40 45

Lys Gly Tyr Leu Gly Cys Gln Ala Leu Ser Glu Met Ile Gln Phe Tyr
50 55 60

Leu Glu Glu Val Met Pro Gln Ala Glu Asn Gln Asp Pro Asp Ile Lys
65 70 75 80

Ala His Val Ile Ser Leu Gly Glu Asn Leu Asn Thr Leu Arg Leu Arg
85 90 95

Leu Arg Arg Cys His Arg Leu Leu Pro Cys Glu Asn Gly Gly Gly Ser
100 105 110

Gly Gly Lys Ser Lys Ala Val Glu Gln Val Lys Asn Ala Phe Asn Lys
115 120 125

Leu Gln Glu Lys Gly Ile Tyr Lys Ala Met Ser Glu Phe Asp Ile Phe
130 135 140

Ile Asn Tyr Ile Glu Ala Tyr Met Thr Met Lys Ile Arg Asn Gly Ile
145 150 155 160

Leu Gly Ser Gly Gly Gly Gly Ser Gly Gly Gly Gly Ser Gly Gly Gly
165 170 175

Gly Ser His Lys Cys Asp Ile Thr Leu Ala Glu Ile Ile Lys Thr Leu
180 185 190

Asn Ser Leu Thr Glu Gln Lys Thr Leu Cys Thr Glu Leu Thr Val Thr
195 200 205

Asp Ile Phe Ala Ala Ser Lys Asn Thr Thr Glu Lys Glu Thr Phe Cys
210 215 220

Arg Ala Ala Thr Val Leu Arg Gln Phe Tyr Ser His His Glu Lys Asp
225 230 235 240

Thr Arg Cys Leu Gly Ala Thr Ala Gln Gln Phe His Arg His Lys Gln
245 250 255

Leu Ile Arg Phe Leu Lys Arg Leu Asp Arg Asn Leu Trp Gly Leu Ala
260 265 270

Gly Leu Asn Ser Cys Pro Val Lys Glu Ala Asn Gln Ser Thr Leu Glu
275 280 285

Asn Phe Leu Glu Arg Leu Lys Thr Ile Met Ala Glu Lys Ala Ser Lys
290 295 300

Cys Ser Ser
305

<210> SEQ ID NO 22
<211> LENGTH: 924
<212> TYPE: DNA
<213> ORGANISM: Artificial Sequence
<220> FEATURE:
<223> OTHER INFORMATION: R5A11-IL4 (Q8A/R121A/Y124A)

<400> SEQUENCE: 22
tccgagaaca gttgcacgca ctttccgggc atccttccta acatgcttcg cgacctgcga 60
gatgcgttct ctcgagtgaa aactttcttt cagatgaaag atcagttgga taatttgctc 120
ctcaaggagt cccttctcga agactttaaa ggatacctgg ggtgccaggc gcttagcgag 180
atgatacagt tctatctgga ggaagtgatg ccccaagcag aaaatcaaga tcccgatatt 240
aaggcccatg tcatcagcct tggcgaaaat ttgaatactc tcagactccg acttcgccga 300
tgccacaggc ttttgccatg tgagaatggg ggtggttccg gggtaagtc caaggccgtt 360 gagcaggtga aaaacgcttt caacaaactg caagaaaagg ggatctacaa agcgatgtca 420
gagttcgaca tatttataaa ctacatagaa gcctatatga cgatgaaaat ccgcaacgga 480
attctaggtt ccggtggcgg tggcagcggc ggtggtggtt ccgggggcgg cggttctcac 540
aagtgcgata tcaccttagc ggagatcatc aaaactttga acagcctcac agagcagaag 600
actctgtgca ccgagttgac cgtaacagac atctttgctg cctccaagaa cacaactgag 660
aaggaaacct tctgcagggc tgcgactgtg ctccggcagt tctacagcca ccatgagaag 720
gacactcgct gcctgggtgc gactgcacag cagttccaca ggcacaagca gctgatccga 780
ttcctgaaac ggctcgacag gaacctctgg ggcctggcgg gcttgaattc ctgtcctgtg 840
aaggaagcca accagagtac gttggaaaac ttcttggaaa ggctaaagac gatcatggca 900
gagaaagctt caaagtgttc gagc 924

<210> SEQ ID NO 23
<211> LENGTH: 307
<212> TYPE: PRT
<213> ORGANISM: Artificial Sequence
<220> FEATURE:
<223> OTHER INFORMATION: R5A11-IL4 (E12A/K84A)

<400> SEQUENCE: 23

```
Glu Asn Ser Cys Thr His Phe Pro Gly Ile Leu Pro Asn Met Leu Arg
1               5                   10                  15

Asp Leu Arg Asp Ala Phe Ser Arg Val Lys Thr Phe Phe Gln Met Lys
            20                  25                  30

Asp Gln Leu Asp Asn Leu Leu Leu Lys Glu Ser Leu Leu Glu Asp Phe
        35                  40                  45

Lys Gly Tyr Leu Gly Cys Gln Ala Leu Ser Glu Met Ile Gln Phe Tyr
    50                  55                  60

Leu Glu Glu Val Met Pro Gln Ala Glu Asn Gln Asp Pro Asp Ile Lys
65                  70                  75                  80

Ala His Val Ile Ser Leu Gly Glu Asn Leu Asn Thr Leu Arg Leu Arg
                85                  90                  95

Leu Arg Arg Cys His Arg Leu Leu Pro Cys Glu Asn Gly Gly Gly Ser
            100                 105                 110

Gly Gly Lys Ser Lys Ala Val Glu Gln Val Lys Asn Ala Phe Asn Lys
        115                 120                 125

Leu Gln Glu Lys Gly Ile Tyr Lys Ala Met Ser Glu Phe Asp Ile Phe
    130                 135                 140

Ile Asn Tyr Ile Glu Ala Tyr Met Thr Met Lys Ile Arg Asn Gly Ile
145                 150                 155                 160

Leu Gly Ser Gly Gly Gly Gly Ser Gly Gly Gly Gly Ser Gly Gly Gly
                165                 170                 175

Gly Ser His Lys Cys Asp Ile Thr Leu Gln Ala Ile Ile Lys Thr Leu
            180                 185                 190

Asn Ser Leu Thr Glu Gln Lys Thr Leu Cys Thr Glu Leu Thr Val Thr
        195                 200                 205

Asp Ile Phe Ala Ala Ser Lys Asn Thr Thr Glu Lys Glu Thr Phe Cys
    210                 215                 220

Arg Ala Ala Thr Val Leu Arg Gln Phe Tyr Ser His His Glu Lys Asp
225                 230                 235                 240

Thr Arg Cys Leu Gly Ala Thr Ala Gln Gln Phe His Arg His Lys Gln
                245                 250                 255

Leu Ile Arg Phe Leu Ala Arg Leu Asp Arg Asn Leu Trp Gly Leu Ala
            260                 265                 270

Gly Leu Asn Ser Cys Pro Val Lys Glu Ala Asn Gln Ser Thr Leu Glu
        275                 280                 285

Asn Phe Leu Glu Arg Leu Lys Thr Ile Met Arg Glu Lys Tyr Ser Lys
    290                 295                 300

Cys Ser Ser
305
```

<210> SEQ ID NO 24
<211> LENGTH: 924
<212> TYPE: DNA
<213> ORGANISM: Artificial Sequence
<220> FEATURE:
<223> OTHER INFORMATION: R5A11-IL4 (E12A/K84A)

<400> SEQUENCE: 24

```
tccgagaaca gttgcacgca ctttccgggc atccttccta acatgcttcg cgacctgcga     60

gatgcgttct ctcgagtgaa aactttcttt cagatgaaag atcagttgga taatttgctc    120

ctcaaggagt cccttctcga agactttaaa ggatacctgg ggtgccaggc gcttagcgag    180

atgatacagt tctatctgga ggaagtgatg ccccaagcag aaaatcaaga tcccgatatt    240
```

-continued

| | |
|---|---|
| aaggcccatg tcatcagcct tggcgaaaat ttgaatactc tcagactccg acttcgccga | 300 |
| tgccacaggc ttttgccatg tgagaatggg ggtggttccg ggggtaagtc caaggccgtt | 360 |
| gagcaggtga aaaacgcttt caacaaactg caagaaaagg ggatctacaa agcgatgtca | 420 |
| gagttcgaca tatttataaa ctacatagaa gcctatatga cgatgaaaat ccgcaacgga | 480 |
| attctaggtt ccggtggcgg tggcagcggc ggtggtggtt ccgggggcgg cggttctcac | 540 |
| aagtgcgata tcaccttaca ggctatcatc aaaactttga acagcctcac agagcagaag | 600 |
| actctgtgca ccgagttgac cgtaacagac atctttgctg cctccaagaa cacaactgag | 660 |
| aaggaaacct tctgcagggc tgcgactgtg ctccggcagt tctacagcca ccatgagaag | 720 |
| gacactcgct gcctgggtgc gactgcacag cagttccaca ggcacaagca gctgatccga | 780 |
| ttcctggctc ggctcgacag gaacctctgg ggcctggcgg gcttgaattc ctgtcctgtg | 840 |
| aaggaagcca accagagtac gttggaaaac ttcttggaaa ggctaaagac gatcatgaga | 900 |
| gagaaatatt caaagtgttc gagc | 924 |

IL-10 MUTEINS

CROSS REFERENCE TO RELATED APPLICATIONS

This application is a United States Application under 35 U.S.C. 371 claiming benefit of PCT Application No. PCT/GB2021/050592, filed on Mar. 10, 2021, which claims the benefit of United Kingdom Application No. 2003428.6, filed on Mar. 10, 2020, the contents of each of which are incorporated herein by reference.

FIELD OF THE INVENTION

The present disclosure relates to modified forms, or muteins, of IL-10, as well as variants thereof, which display improved features as compared to wild-type IL-10. The present invention further relates to the use of such modified forms, or muteins, of IL-10, as well as variants thereof in methods, including therapeutic methods.

BACKGROUND TO THE INVENTION

Interleukin-10 (IL-10) is a hallmark cytokine for immune regulation that elicits potent anti-inflammatory responses. IL-10 regulates the adaptive arm of the immune response by reducing the antigen presentation potential of innate cells through decreasing their surface major histocompatibility complex (MHC) levels and co-stimulatory molecules (de Waal Malefyt et al., 1991b, Willems et al., 1994). In addition, IL-10 potently suppresses the production of pro-inflammatory cytokines from a variety of cells types including monocytes, macrophages and T cells (Fiorentino et al., 1991a, Fiorentino et al., 1991b), further contributing to an anti-inflammatory environment. IL-10's critical contribution to a healthy immune response is further highlighted by the finding that IL-10 deficient humans develop severe autoimmune diseases such as Crohn's disease and colitis (Correa et al., 2009, Zhu et al., 2017). Despite IL-10's relevancy for human health, the molecular bases allowing IL-10 to elicit its broad spectrum of anti-inflammatory activities are poorly understood.

Because of its potent anti-inflammatory properties, IL-10 was regarded as a very attractive drug target to treat autoimmune disorders. However, despite efficacy in mouse studies (Saxena et al., 2015, Cardoso et al., 2018), IL-10 therapies failed to produce beneficial results in the clinic, with several clinical trials showing only mild efficacy and biased responses in patients (Colombel et al., 2001, Buruiana et al., 2010). A leading hypothesis to explain the poor clinical efficacy of IL-10 is that during IL-10 therapies low levels of this cytokine reach the gastrointestinal tract, thus failing to produce an effective response. However, to date we have a poor understanding of how IL-10 doses influence its immune-modulatory potential. Supporting this model, the development of strategies for a more targeted IL-10 delivery are showing enhanced clinical efficacy, although these studies are still at an early stage (Cardoso et al., 2018, Steidler et al., 2000, Shigemori and Shimosato, 2017, Braat et al., 2006). An IL-10 variant with the ability to elicit robust responses at therapeutically relevant doses would be highly desirable.

In addition to its anti-inflammatory activities, recent studies have shown that IL-10 can increase the cytotoxic function of CD8 T cells, augmenting their ability to target tumours and boosting the anti-cancer response (Oft, 2019). This seems paradoxical as IL-10 in the tumour microenvironment is linked to tumour evasion of the immune response, most likely due to IL-10's inhibitory effects on antigen presentation (Yue et al., 1997, Mannino et al., 2015). Despite this paradox, several studies have elegantly demonstrated that IL-10 can improve production of the CD8 effector molecules granzyme B and interferon gamma both in vitro and in vivo (Emmerich et al., 2012, Mumm et al., 2011, Mumm and Oft, 2013). Currently there are several clinical trials testing the anti-tumour properties of IL-10, with already initial promising results (Naing et al., 2019). In these trials high doses of PEGylated IL-10 (Pegilodekakin) were used, which resulted in prolonged IL-10 retention in the circulation to ensure efficacy, again highlighting that effective IL-10 in vivo responses need high concentrations and sustained levels of IL-10.

IL-10 is a dimeric cytokine, which exerts its activities by binding a surface receptor comprised of two IL-10Rα and two IL-10Rβ receptor subunits, triggering the activation of the JAK1/TYK2/STAT3/STAT1 signalling pathway and the induction of specific gene expression programs. Kinetically, IL-10 first binds with high affinity to two molecules of IL-10Rα and in a second step with low affinity, it recruits two molecules of IL-10Rβ forming the active signalling hexameric IL-10 complex. A striking feature of the IL-10 system when compared to other cytokines is that IL-10 binds with extremely weak affinity to IL-10Rβ, in the order of high μM/low mM range, (Logsdon et al., 2002) making this system exquisitely sensitive to changes in either ligand and/or receptor concentrations.

SUMMARY OF THE DISCLOSURE AND INVENTION

The present disclosure is based on an hypothesis that IL-10's poor in vivo activities result from its weak affinity for the IL-10Rβ subunit. An IL-10 variant binding IL-10Rβ with enhanced affinity has the potential to overcome the in vivo limitations of this cytokine and rescue IL-10 based therapies. To test this hypothesis, the present inventors have used a yeast surface display engineering platform to generate a new IL-10 variant, which binds IL-10Rβ 1000-fold better than IL-10 wild type (wt).

In a first aspect, there is provided an IL-10 mutein, wherein the IL-10 mutein comprises at least one amino acid substitution at positions 18, 92 and 99, as compared to full-length mature wild-type IL-10. Said another way, the IL-10 mutein comprises one or more amino acid substitutions at a position or positions selected from position(s) 18, 92 and 99. Numbering is with respect to the wild-type IL-10 sequence found shown in SEQ ID NO: 1, but excluding the signal peptide sequence which constitutes the first 18 amino acid residues in the wild type and mutein IL-10 sequences identified. For the avoidance of doubt, the mature wild-type sequence starts Ser Pro Gly. For the further avoidance of doubt, amino acid substitution as used herein refers to the substitution of an amino acid, with another naturally occurring amino acid, as exemplified herein.

In one embodiment, the IL-10 mutein comprises at least two amino acid substitutions, selected form, or at, positions 18, 92 and 99. In one embodiment, the IL-10 mutein comprises amino acid substitutions at all three positions, 18, 92 and 99.

In one embodiment where there is a substitution at position 18 and the substitution is Y or I (lettering according to recognised one-letter amino acid codes).

In one embodiment where there is a substitution at position 92 and the substitution is I.

In one embodiment where there is a substitution at position 99 and the substitution is N.

Optionally, the IL-10 mutein may comprise one or more further substitutions, but typically less than 10, 9, 8, or 7 substitutions as compared to the wild-type IL-10 sequence. In one embodiment said, one or more further substitutions may be at positions 55, 69, 97, 110, 111 and/or 148—again numbering is in comparison to the wt IL-10 sequence identified in SEQ ID NO:1, but excluding the signal peptide sequence which constitutes the first 18 amino acid residues in the wild type sequence.

In one embodiment, the IL-10 mutein, comprises, consists, or consists essentially of the sequence according to SEQ ID Nos: 5, 7, 11 or 15. In this context, "consists essentially of", refers to an IL-10 mutein which is at least 97, 98 or 99% identical to the sequence according to SEQ ID NO: 5, 7, 11 or 15, but comprises at least the amino acid substitutions identified in SEQ ID NO:5, 7, 11 or 15, which differ with respect to the wild-type IL-10 sequence (SEQ ID NO: 1).

Thus, in addition to the above-identified mutations, the IL-10 muteins of the invention may comprise one or more further amino acid modifications, e.g. substitutions (such as conservative substitutions), insertions, deletions, or inversions, providing that one or more further modifications, do not substantially affect the activity of the IL-10 mutein in a deleterious manner.

In its functionally active native state, IL-10 is found as a dimer formed from two identical monomers. The IL-10 muteins, as described herein, are generally described in terms of the monomeric sequence, but it will be appreciated that a dimer may be formed from two monomeric IL-10 mutein sequences. As will be described in more detail, the inventors have also developed IL-10 mutein fusions, which comprise an IL-10 mutein, as described herein, fused to another molecule. Additionally, the inventors describe a pentameric form of an IL-10 mutein as described.

Wild-type IL-10 is found in a dimeric form, which makes its manipulation challenging, the inventors have used a monomeric IL-10 variant previously described by the Walter group as an engineering scaffold (Josephson et al., 2000). The inventors generated monomeric IL-10 variants with increased affinity as compared to wild-type and then translated this into its natural dimeric conformation, thus obtaining IL-10 muteins in monomeric and dimeric form. These molecules provided the inventors with the unique opportunity to assess the contributions of IL-10 receptor binding affinity as well as IL-10 receptor complex stoichiometry to IL-10 biology. Data as presented herein shows that increasing the affinity of IL-10 for IL-10Rβ enhances IL-10's known properties at both the molecular and cellular level. Quantitative imaging studies revealed that IL-10 muteins described herein, either in monomeric or multimeric, such as dimeric forms, exhibited improved receptor complex assembly, which in turn, resulted in a more potent activation of STAT1 and STAT3 factors by the engineered cytokines. In agreement with their improved signalling profiles, affinity enhanced IL-10 variants induced more robust gene expression programs than the wild type ligands in monocytes and CD8 T cells and stronger cellular responses. The data presented further provides novel insights into how IL-10 doses regulate its immune-modulatory activities and show that IL-10 muteins described herein represent a clear therapeutic advantage over wild type IL-10 by eliciting more robust bioactivities at a wider range of doses.

Conveniently, the IL-10 muteins described herein may display increased IL-10 receptor binding affinity and/or functional activity, as compared to wild-type IL-10. In one embodiment, said IL-10 mutein binds with higher affinity to IL-10Rβ, as compared to wild-type IL-10. Conveniently, an increase in affinity may be determined in accordance with a suitable assay for determining IL-10 affinity known in the art (See Moraga et al, 2015a), or as described herein. Typically, the increase in affinity (typically in terms of Kd) may be at least 2-fold, such as 5-fold, 10-fold, 25 fold, 50 fold, 100-fold, 250 fold, 500-fold, 1000-fold, or higher. An increase in functional activity may be determined in relation to a suitable IL-10 activity assay as known by the skilled reader. Suitable activity assays may be directed to activation of STAT1 and/or STAT3 factors, enhanced gene expression and/or cellular responses, for example. Suitable assays for detecting such functional activity of IL-10 are known to the skilled addressee and are described for example in Moore et al, 2001.

In a further embodiment there is provided an IL-10 mutein as described herein, fused with a further different IL molecule, such as IL-4 (e.g. SEQ ID NO: 19), or other molecule. The further different IL molecule may be a wild-type or mutant IL molecule. In one embodiment there is provided an IL-10 mutein as described herein, fused with a mutant IL-4 molecule that does not bind a common gamma chain or IL-13Rα1 and therefore acts as an antagonist of IL4 and IL-13. In one embodiment, such an IL-10 mutein/IL-4 fusion may recruit a trimeric receptor complex comprising IL-10Rα/IL-10Rβ/IL-4Rα, which may display anti-inflammatory properties. An exemplary fusion protein comprises the sequence, which is at least 97, 98, 99%, or 100% identical to the sequence as identified in SEQ ID NO: 19, but comprises at least the amino acid substitutions identified in SEQ ID NO: 11 which differ with respect to the wild-type IL-10 sequence (SEQ ID NO: 1).

An IL-10 mutein as described herein may be fused to at least one polypeptide binding domain, such as an antibody or fragment thereof, for example a single chain antibody, such as a VHH. In certain teachings, the polypeptide binding domains may bind to one or more of any of the following:

to at least one checkpoint molecule selected from CD27, CD137, 2B4, TIGIT, CD155, ICOS, HVEM, CD40L, LIGHT, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDOI, ID02, TDO, KIR, LAG-3, TIM-3, and/or VISTA, conveniently PD-L1, PD1;

to at least one dendritic cell surface marker selected from CD1c, CD11c, SIRPa, CD206/MR, CD14, CD141, XCR1, Clec9a, CADM1/Necl2 (see Saxena & Bhardwaj, 2017), Clec9a, CD141, XCR1, CADM1, CD1c, CD32b, CD123, BDCA-2, BDCA-4, CD141, CD1c, CD11c, CD1a, Langerin/CD207, CD14 (see Rhodes et al., 2019), CD123, BDCA-2, BDCA-4, CD141, BDCA-1, CD1c, CD11c, Langerin/CD207 (see Collin & Bigley, 2018), DEC-205, DC-SIGN, DCIR2/Clec4A4 (see DEC-205, DC-SIGN, or DCIR2/Clec4A4 (see Moutel et al., 2020; WO 2018/069480 (A1));

to at least one inflammatory tissue marker selected from Alpha(v) integrins (such as αvβ1, αvβ3, αvβ5 and αvβ38), CH13L1 (YKL-40), CXCR4, E-Selectin, FAP, EDA and EDB Fibronectin, Galectin-3, ICAM-1, IGF2R (CI-MPR), LFA-1, MadCAM-1 (Adressin), MUC2, MUC4, PDGFR alpha, PDGFR beta, PSGL-1, STRA6 (RBP receptor), VCAM-1 (see Yazdani et al., 2017; Jin et al., 2018; Lemańska-Perek & Adamik, 2019; Farkas et al., 2006; Mejías-Luque et al., 2010; Kelly et al., 2012; Siew et al., 2019; Gonen et al., 2018; Kircher et al., 2018);

to at least one microglia marker selected from CD11b, CD40, CD45, CD68, CX3CR1, EMR1 (F4/80), Iba1, TMEM19 (see Bennett et al., 2016); and at least one tumor antigen selected from EpCAM, EGFR, HER-2, HER-3, c-Met, FolR, PSMA, CD38, BCMA, CEA, 5T4, AFP, B7-H3, Cadherin-6, CAIX, CD117, CD123, CD138, CD166, CD19, CD20, CD205, CD22, CD30, CD33, CD40, CD352, CD37, CD44, CD52, CD56, CD70, CD71, CD74, CD79b, CLDN18.2, DLL3, EphA2, ED-B fibronectin, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1 Muc16, NaPi2b, Nectin-4, P-cadherin, NY-ESO-1, PRLR, PSCA, PTK7, ROR1, SLC44A4, SLTRK5, SLTRK6, STEAP1, TIM1, Trop2, and/or WT1.

Additionally, or alternatively, an IL-10 mutein as described herein may be fused to a half-life extending molecule, for example, an immunoglobulin fragment such as an Fc molecule, or a polypeptide binding domain against a blood serum protein, for example, against albumin.

An alternative IL-10 mutein/IL-4 mutant fusion, may bind with reduced affinity to IL-4Ra. Thus, a further exemplary fusion protein comprises the sequence, which is at least 97, 98, 99%, or 100% identical to the sequence as identified in SEQ ID NO: 21, but comprises at least the amino acid substitutions identified in SEQ ID NO: 11 which differ with respect to the wild-type IL-10 sequence (SEQ ID NO: 1). Such a fusion molecule may be capable of triggering IL-10 and IL-4 signalling responses only in cells which express a fully functional IL-10 receptor complex, which may limit toxicity associated with systemic IL-4 stimulation.

Additionally, the present inventors have observed that the IL-10 muteins of the invention result in enhanced CD8 T cell cytotoxic activities. Thus, it is envisaged that the IL-10 muteins of the invention may facilitate CAR T cell based therapies. Thus, in a further teaching, the present invention provides an IL-10 mutein as described herein, for use in combination with a CAR T cell in a method of treatment, such as to enhance a cytotoxic effect of the CAR T cell, in absence of the IL-10 mutein.

In one embodiment, the IL-10 mutein is further modified such as by posttranslational modification, such as glycosylation and/or amidation. Other modifications include conjugating a further molecule, such as PEG, to the IL-10 muteins of the invention. Details of how wild-type IL-10 may be modified by pegylation and which may be adopted for the IL-10 muteins described herein, are described in U.S. Pat. No. 9,925,245, to which the skilled reader is directed and the entire contents of which are hereby incorporated by way of reference.

Also provided is a nucleic acid molecule, such as a DNA or RNA molecule encoding an IL-10 mutein, as well as the variants and modified forms, fusion proteins as described herein according to any of the provided embodiments. In some embodiments, the nucleic acid molecule is synthetic nucleic acid. In some embodiments, the nucleic acid molecule is cDNA.

Also provided is a vector containing the nucleic acid molecule according to any of the provided embodiments. In some cases, the vector is an expression vector. In some aspects, the vector is a mammalian expression vector or a viral vector. Such a vector may be in the form of a plasmid, viral vector or phagemid, for example.

Additionally, a polypeptide, polynucleotide or vector as described herein, may be provided with a suitable carrier molecule, such as a lipid or non-ionic surfactant vesicle, nanoparticle, lipoplex of the like.

Also provided is a cell, comprising the vector according to any of the provided embodiments. In some instances, the cell is a mammalian cell. In some aspects, the cell is a human cell. In some embodiments, the cell is an immune cell or lymphocyte.

Also provided is a method of producing an IL-10 mutein, as well as the variants and modified forms, fusion proteins as described herein, comprising introducing the nucleic acid molecule according to any of the provided embodiments or vector according to any of the provided embodiments into a host cell under conditions to express the protein in the cell. In some instances, the method further includes isolating or purifying an IL-10 mutein, as well as the variants and modified forms, fusion proteins as described herein from the cell.

Also provided is a method of engineering a cell expressing an IL-10 mutein, as well as the variants and modified forms, fusion proteins as described herein, including introducing a nucleic acid molecule encoding the IL-10 mutein, as well as the variants and modified forms, fusion proteins as described herein into a host cell under conditions in which the polypeptide is expressed in the cell.

The IL-10 muteins of the present invention, as well as the variants and modified forms, fusion proteins and combinations with other molecules as described herein, may find particular application in therapeutic methods. Thus, in one embodiment there is provided a pharmaceutical formulation comprising an IL-10 mutein, of the present invention, as well as the variants and modified forms, fusion proteins and combinations with other molecules as described herein, optionally together with a pharmaceutically acceptable excipient, for use in a method of treatment. There is also provided a method of treatment comprising administering an IL-10 mutein, of the present invention, as well as the variants and modified forms, fusion proteins and combinations with other molecules as described herein to a subject in need thereof.

Where an IL-10 mutein of the invention is administered in combination therapy with one, two, three, four or more, preferably one or two, preferably one other therapeutic agents, the IL-10 mutein can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The IL-10 muteins of the invention may also be administered in conjunction with a further—therapeutic(s) such as PD1 antibody, or other anti-cancer antibodies known in the art, or anti-TNF, or anti-IL6 antibodies designed to prevent inflammation. The subject is typically an animal, e.g. a mammal, especially a human.

By a therapeutically or prophylactically effective amount is meant one capable of achieving the desired response, and will be adjudged, typically, by a medical practitioner. The amount required will depend upon one or more of at least the active IL-10 muteins concerned, the patient, the condition it is desired to treat or prevent and the formulation of order of from 1 μg to 1 g of compound per kg of body weight of the patient being treated.

Different dosing regiments may likewise be administered, again typically at the discretion of the medical practitioner. The IL-10 muteins of the invention, allow for at least daily administration although regimes where the IL-10 muteins is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the IL-10 muteins or a physiologically acceptable salt, solvate, ester or amide thereof described herein may be presented as a pharmaceutical formulation, comprising the IL-10 mutein or physiologically acceptable salt, ester or other physiologically functional derivative thereof, together with one or more pharmaceutically acceptable carriers therefor and optionally other therapeutic and/or prophylactic ingredients. Any carriers) are acceptable in the sense of being compatible with the other ingredients of the formulation and not deleterious to the recipient thereof. Suitable further therapeutic and/or prophylactic agents include an anti-cancer agent, anti-inflammatory agent, or an immune tolerance promoting agent Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral or rectal administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers, which are sealed after introduction of the formulation until required for use.

Alternatively, an active compound may be in powder form, which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example; suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device; or alternatively as a self-propelling formulation comprising an active compound; a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation. Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or, 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like. Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated. Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus, particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the IL-10 mutein or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

Also provided are IL-10 muteins (and compositions, including the nucleic acid compositions), as well as the variants and modified forms, fusion proteins and combinations with other molecules as described herein, for use in methods for the treatment and/or prevention of diseases associated with reduced IL10 expression or function such as chronic inflammation, such as rheumatoid arthritis, graft vs host disease and inflammatory bowel disease/Crohn's disease. Further diseases which may be treated in accordance with the present invention include inflammatory disease, or autoimmune diseases is selected from arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phaco antigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

In view of its effect on CD8 T cell response, the IL-10 muteins (and compositions), as well as the variants and modified forms, fusion proteins and combinations with other molecules as described herein, may find use in methods for the treatment and/or prevention of cancers.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2nd ed. (1989) Cold Spring Harbor Laboratory Press, Cold Spring Harbor, N.Y., which is incorporated herein by reference), which are provided throughout this document. The nomenclature used herein and the laboratory procedures of analytical and synthetic organic chemistry described below are those well-known and commonly employed in the art. Standard techniques, or modifications thereof, are used for chemical syntheses and chemical analyses.

"wild type" as used herein refers to an amino acid sequence or a nucleotide sequence that is found in nature, including allelic variations. "Wild type IL-10" means IL-10, whether native or recombinant, having the 160 normally occurring amino acid sequence of native human IL-10, SEQ ID NO: 1 that does not include the 18-amino acid IL-10 signal peptide.

The term "polypeptide", "protein" or "peptide" refer to any chain of amino acid residues, regardless of its length or post-translational modification (e.g., glycosylation or phosphorylation).

As used herein, "mutein" means a polypeptide comprising amino acid insertions, deletions, substitutions and modifications at one or more sites relative to a wild type polypeptide. Exemplary muteins can include substitutions of 1, 2, 3, 4, 5, 6, 7, 8, 9, 10 or more amino acids.

As well as the defined mutations described herein, the muteins of the present invention may also include conservative modifications and substitutions throughout the wild type polypeptide or polynucleotide sequence (e.g., those that have a minimal effect on the secondary or tertiary structure of the mutein). Such conservative substitutions include those described by Dayhoff in The Atlas of Protein Sequence and Structure 5 (1978), and by Argos in EMBO J., 8:779-785 (1989).

The terms "treating" or "treatment" or "therapy or "therapies" refer to both therapeutic treatment and prophylactic or preventative measures, wherein the object is to prevent or slow down (lessen) the targeted pathologic condition or disorder.

The present invention will now be further described by way of example and with reference to the figures, which show:

FIG. 1. Generation of high affinity IL-10 variants by yeast surface display. A. Schematic of IL-10 stepwise receptor assembly for IL-10 dimer (top panel) and IL-10 monomer (bottom panel). B. Schematic of IL-10 dimer and IL-10 monomer secondary structure organisation as described by (Walter, 2014, Josephson et al., 2000). Extended linker region is highlighted in blue. C. Representation of IL-10 displayed on yeast cell surface and screening using fluorescently labelled recombinant IL-10Rβ. D. Yeast displayed wild type IL-10 IL-10Rα binding (panel 2) and IL-10Rβ binding in the absence (panel 3) or presence (panel 4) of IL-10Rα. Unstained control shown in panel 1. E. Outline of ligand conditions used in each yeast display selection round. Selection rounds started at 1 μM IL-10Rβ with 100 nM non-biotinylated IL-10Rα and finishing with 20 nM IL-10Rβ alone. F. Representative histogram of IL-10Rβ binding (AF647) of yeast displayed wild type IL-10, round 3 selection, round 6 selection and round 8 selection. As the library selection proceeds the IL-10RP staining improves. G. The highest IL-10Rβ concentration is 1 μM with a ⅓ serial fold dilution over 7 concentrations. Non-biotinylated IL-10Rα was added at 100 nM to improve cooperative binding. H. Table for amino acid changes found in high affinity mutants. Wild type sequence is show in yellow. Conserved changes between mutants are shown in blue. Individual mutations are shown in white. I. Panel one depicts the wild type IL-10 structure with helices A and D emphasised in red as the area predicted by (Mendoza et al., 2017) to be the IL-10Rβ binding site. Panel 2 shows the structures for the high affinity variant R5A11 with mutations highlighted in purple J Dose response for IL-10Rβ binding for G3 clone from yeast display library.

FIG. 2. Increased IL-10Rβ binding affinity enhances IL-10 receptor dimerization. (a). Quantifying receptor dimerization in the plasma membrane by dual-colour single molecule SUBSTITUTE SHEET (RULE 26) colocalization and co-tracking. IL-10Rα and IL-10Rβ with N-terminally fused variants of monomeric ECFP and EGFP, respectively, were labelled with nanobodies $EN^{AT643}$ and $MI^{Rho11}$, respectively. (b). Trajectories of IL-10Rα (blue), IL-10Rβ (red) and co-localized IL-10Rα:IL-10Rβ (magenta) in the absence of IL-10 (left column) and in the presence of WTD (middle column) and R5A11D (right column), respectively. (c). Heterodimerization of IL-10Rα and IL-10Rβ (left), and homodimerization of IL-10Rα (center) and IL-10Rb (right) induced by dimeric IL-10 variants quantified by co-locomotion analysis. Each data point represents a cell with the number of cells of each experiments indicated in the box plot. (d). Homo- and heterodimerization of IL-10Rα and IL-10Rβ induced by monomeric IL-10 variants quantified by co-locomotion analysis.

Figure 3:
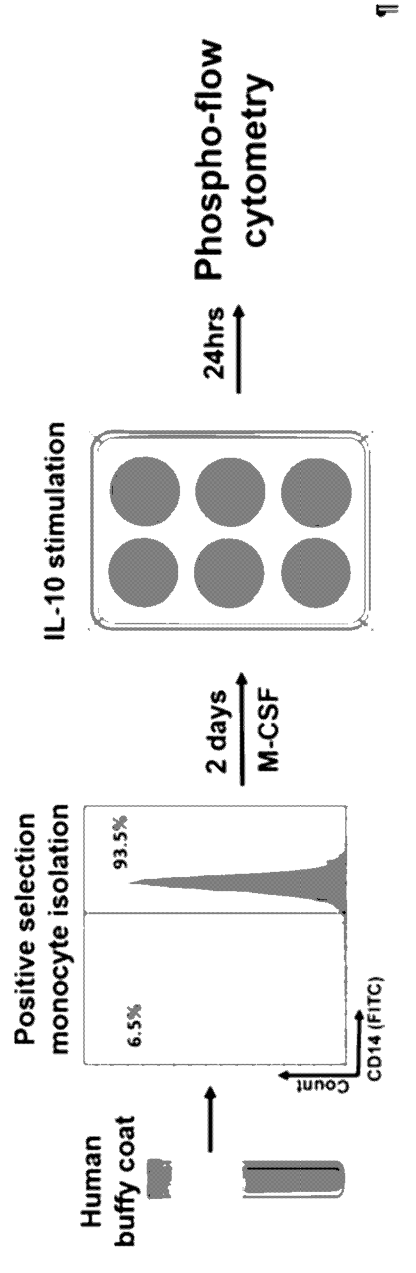
Figure 3:
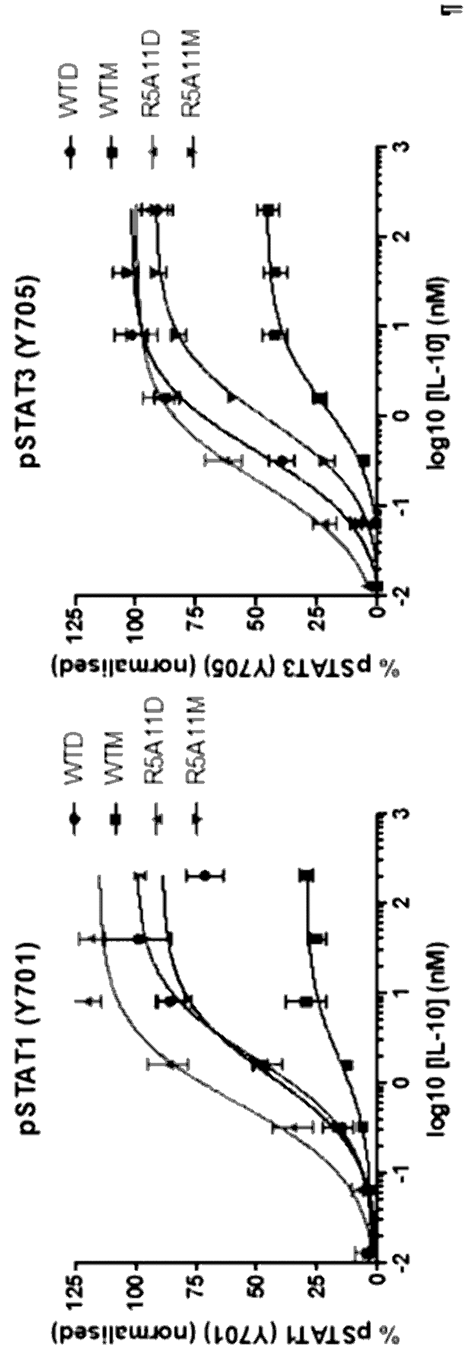
Figure 3:
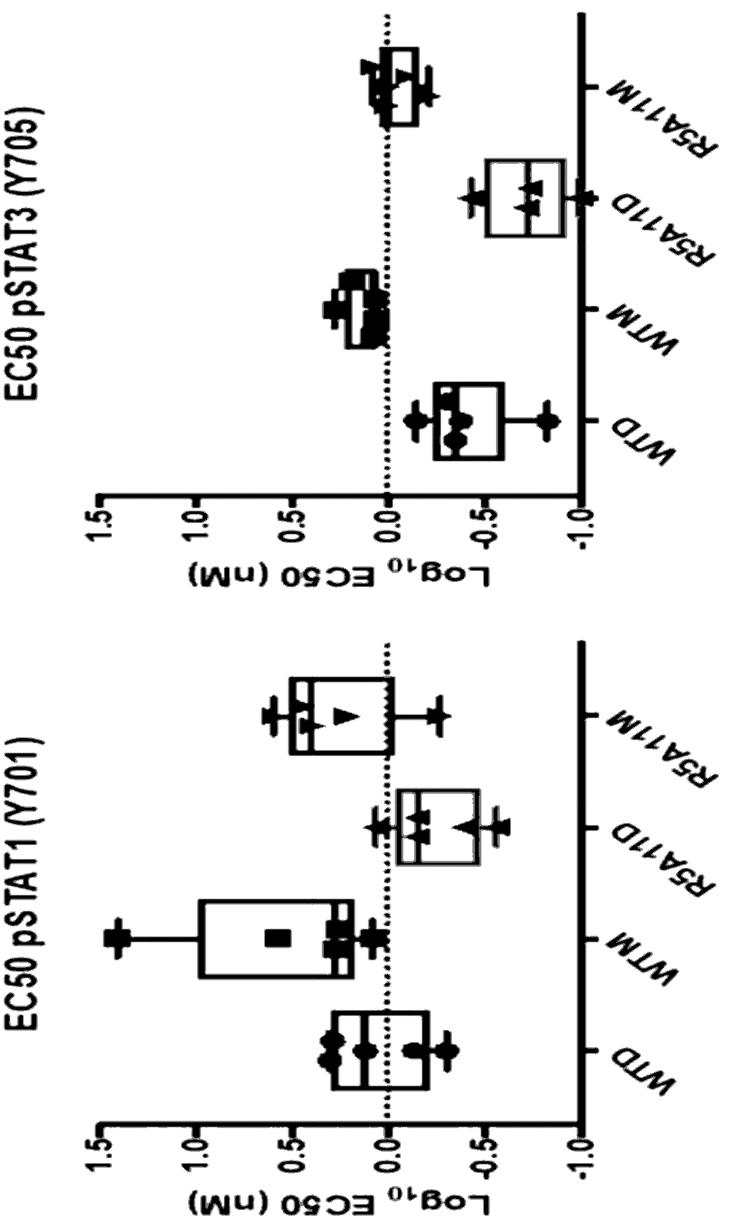

FIG. 3. High affinity variants improve signalling capabilities of IL-10 in monocytes. A. Monocytes were isolated from human buffy coat samples by CD14 positive MACS selection. Cells were rested in M-CSF containing media for 2 days. Cells were then stimulated with IL-10 for 24 hours before analysis. B. Dose response of pSTAT3 and pSTAT1 in IL-10 treated monocytes. Cells were stimulated with IL-10 wild type and high affinity variants for 15 minutes. Activation of STAT3 and STAT1 was analysed by phospho-flow cytometry. Sigmoidal curves were fitted with GraphPad Prism software. Data shown is the mean of five biological replicates with error bars depicting standard error of the mean. Each biological replicate is normalised by assigning the highest MFI value of the top concentration as 100% and the lowest MFI value of an untreated control as 0%. C. $Log_{10}$ EC50 values for pSTAT1 and pSTAT3 from dose response curves in B. Each point represents one biological replicate with line at the mean and error bars show the mix to max of all points. D. Ratio of pSTAT1 to pSTAT3 in IL-10 stimulated monocytes. Ratio was calculated by taking the percentage activation of pSTAT3 and pSTAT1 at 40 nM for five biological replicates and dividing pSTAT1 by pSTAT3 values. Each point represents one biological replicate with line at the mean and error bars show the min to max of all points. E. Kinetics of pSTAT3 and pSTAT1 induced by IL-10. Monocytes were stimulated with IL-10 for the indicated time periods before fixation. Data shown is the mean of four biological replicates with error bars depicting standard error of the mean. Each biological replicate is normalised by assigning the highest MFI value at 15 mins as 100% and the lowest MFI value of an untreated control as 0%. F. Measurement of H LA-DR cell surface expression in monocytes after 24 hours IL-10 treatment. Each point represents one biological replicate (n=4) and error bars indicate the standard deviation. Fold change is calculated for each biological replicate by dividing the MFI of the treated samples by a non-IL-10 treated control (unstimulated). G. Monocytes were stimulated with LPS for 8 hours in the presence of IL-10. Each point represents one biological replicate (n=3) and error bars indicate the standard error of the mean. P value calculated by two-tailed ratio paired t-test.

FIG. 4. Characterisation of transcriptional activity induced by IL-10 and high affinity variants in human monocytes. A. Schematic of monocyte stimulation. CD14 positive cells were isolated from three human buffy coats by MACS and rested in M-CSF containing media for two days before twenty-four hours stimulation with IL-10 wild type and high affinity variants. B. Volcano plot of monocyte genes significantly upregulated by IL-10 wild type dimer ≥0.6 $log_2$ fold change (red) and significantly downregulated ≤−0.6 $log_2$ fold change compared to non-IL-10 stimulated cells. Fold change was calculated by dividing WTD 50 nM by unstimulated values for each donor. The average fold change was calculated and the $log_2$ of this value is plotted. P values ≤0.05 were calculated by two-tailed unpaired t-test of the $log_2$ fold change of WTD 50 nM/unstimulated genes for each donor. Genes which were not significantly changed or were ≤0.6≥−0.6 $log_2$ fold change were excluded. C. Proportion of monocyte genes significantly regulated by WTD 50 nM ≥0.6 or ≤−0.6 $log_2$ fold change compared to unstimulated cells. D. $Log_2$ fold change for the top 20 protein coding genes significantly up (red) and down (blue) regulated by WTD 50 nM in monocytes. E. Percentage activity of low dose WTD compared to high dose WTD. The $log_2$ fold change of WTD 0.1 nM was divided by WTD 50 nM and multiplied by 100. Genes which showed 75% of high dose activity (183 genes) are highlighted in red. Insert shows the percentage of these genes which up or downregulated activity. F. Gene ontology biological processes analysis for the 183 genes which were sensitive to changes in WTD concentration. G.$Log_2$ fold change for inflammatory cytokines and chemokine genes for WTD 50 nM and 0.1 nM. H. Heatmap of genes significantly up or down regulated by WTD 50 nM ≥0.6 or ≤−0.6 $log_2$ fold change and their corresponding $log_2$ fold change by R5A11D 50 nM, WTD 0.1 nM, R5A11D 0.1 nM, R5A11M 50 nM and WTM 50 nM compared to unstimulated control cells. Values are the mean of three donors. Heat map cluster analysis generated in R studio. I. Volcano plot of genes regulated by WTD (blue) and R5A11D (green) at 0.1 nM concentration each. Only genes which had already been showed to be significantly up or down regulated by WTD 50 nM are plotted. J. Heatmap of the top 10 up and down regulated genes by WTD 0.1 nM compared to R5A11D 0.1 nM. K. Heatmap of inflammatory cytokine and chemokine genes regulated by WTD at 50 nM and 0.1 nM and R5A11D 0.1 nM.

FIG. 5. High affinity variants improve signalling capabilities of IL-10 in human CD8 T cells. A. PBMCs were isolated from human buffy coat samples and CD8 cells were purified by CD8 positive MACS selection. PBMCs or purified CD8 cells were activated for three days using soluble anti-CD3 (100 ng/mL) (PBMCs) or anti-CD3/anti-CD28 beads (CD8 cells) with IL-2 (20 ng/mL) in the presence or absence of IL-10. On day 3 activation media was removed and the cell populations were placed in media containing IL-2 plus/minus IL-10 for a further 2-3 days before analysis. B. Dose response of pSTAT3 and pSTAT1 in activated CD8 cells in a PBMC population (activated in the absence of IL-10). Cells were placed in media with no IL-2 overnight before stimulation with IL-10 wild type and mutants for 15 minutes. Data shown is the mean of four biological replicated with error bars depicting standard error of the mean. Each biological replicate is normalised by assigning the highest MFI value of the top concentration as 100% and the lowest MFI value of an untreated control as 0%. C. Log EC50 values for pSTAT3 and pSTAT1 from dose response curves in B. Each point represents one biological replicate with line at the mean and bars represent the mix to max of all points. D. Ratio of pSTAT1 to pSTAT3 in IL-10 stimulated CD8 cells in a PBMC population. Ratio was calculated by taking the percentage activation of pSTAT3 and pSTAT1 at 40 nM for four biological replicates and dividing pSTAT1 by pSTAT3 values. Each point represents one biological replicate with line at the mean and error bars denote mix to max of all points. E. Kinetics of pSTAT3 and pSTAT1 induced by IL-10. Non-activated CD8 cells in a PBMC population were stimulated with IL-10 for the indicated time periods before fixation. Data shown is the mean of three biological replicates with error bars depicting standard error of the mean. Each biological replicate is normalised by assigning the highest MFI value at 15 mins as 100% and the lowest MFI value of an untreated control as 0%. F. Granzyme B protein in activated CD8 T cells in the presence of IL-10. CD8 T cells in a PBMC population were grown and stimulated as shown in A. Cells were then fixed and permeabilised and granzyme B protein was quantified by flow cytometry. Fold change was calculated by normalised to a non-IL-10 treated control for each donor. Each point represents one biological replicate (n=8) and error bars indicate the standard deviation.

FIG. 6. Characterisation of transcriptional activity induced by IL-10 and high affinity variants in human CD8 T cells. A. Schematic of CD8 T cell stimulation. CD8 T cells were isolated by MACS and activated with anti-CD3/CD28 beads and IL-2 in the presence or absence of IL-10 wt and variants for three days. On day three the media was changed to IL-2 in the presence or absence of IL-10 wt and variants and cells were expanded for a further three days. B. Volcano plot of CD8 T cell genes significantly upregulated by IL-10 wild type dimer ≥0.6 $\log_2$ fold change (red) and significantly downregulated ≤−0.6 $\log_2$ fold change compared to non-IL-10 stimulated cells. Fold change was calculated by dividing WTD 50 nM by unstimulated values for each donor. The average fold change was calculated and the $\log_2$ of this value is plotted. P values ≤0.05 were calculated by two-tailed unpaired t test of the $\log_2$ fold change of WTD 50 nM/unstimulated genes for each donor. Genes which were not significantly changed or were ≤0.6≥−0.6 $\log_2$ fold change were excluded. C. Proportion of CD8 T cell genes significantly regulated by WTD 50 nM ≤0.6 or ≤−0.6 $\log_2$ fold change compared to unstimulated cells. D. $\text{Log}_2$ fold change for the top 20 protein coding genes significantly up (red) and down (blue) regulated by WTD 50 nM in CD8 T cells. E. Heatmap of genes previously reported to be present in exhausted T cells. A list of exhaustion specific genes from (Bengsch et al., 2018) was used as a comparison for genes significantly up or down regulated by WTD 50 nM. Previously reported genes were given a nominal value of 1 for upregulated genes and −1 for downregulated genes. $\text{Log}_2$ fold change for WTD 50 nM was plotted. Cluster 1 (C1) represents genes upregulated in exhausted cells and upregulated by WTD 50 nM. C2 represents genes upregulated in exhausted cells and downregulated by WTD 50 nM. C3 represents genes downregulated in exhausted cells and upregulated by WTD 50 nM. C4 represents genes downregulated in exhausted cells and downregulated by WTD 50 nM. F. The $\log_2$ fold change induced by WTD 50 nM for a sample of genes from each cluster is shown. G. The RKPM of unstimulated and WTD 50 nM conditions for the IL2RA gene in each donor. H. Heatmap showing the $\log_2$ fold change induced by WTD 50 nM for genes previously reported to be regulated by IL-2 (Rollings et al., 2018). I. Percentage activity of low dose WTD compared to high dose WTD. The $\log_2$ fold change of WTD 0.1 nM was divided by WTD 50 nM and multiplied by 100. Genes which showed ≤75% of high dose activity (781 genes) are highlighted in red. Insert shows the percentage of these genes which up or downregulated activity. J. $\text{Log}_2$ fold change for genes associated with exhaustion or IL-2 stimulation and their regulation of WTD at 50 nM or 0.1 nM concentration. K. Heatmap of genes significantly up or down regulated by WTD 50 nM ≥0.6 or ≤−0.6 $\log_2$ fold change and their corresponding $\log_2$ fold change by R5A11D 50 nM, WTD 0.1 nM, R5A11D 0.1 nM, R5A11M 50 nM and WTM 50 nM compared to unstimulated control cells. Values are the mean of three donors. L. Volcano plot of genes regulated by WTD (blue) and R5A11D (green) at 0.1 nM concentration each in CD8 T cells. Only genes which had already been showed to be significantly up or down regulated by WTD 50 nM are plotted. J. Comparison of regulation of CD8 T cell genes by R5A11D 0.1 nM and WTD 0.1 nM. The $\log_2$ fold change of R5A11D 0.1 nM/unstimulated was divided by the $\log_2$ fold change of WTD 0.1 nM/unstimulated. Proportion of genes which show enhanced regulation by R5A11D are shown in red, proportion of genes which show diminished regulation by R5A11D are shown in blue and genes which do not change between R5A11D and WTD are shown in grey. M. Heatmap of the top 10 up and down regulated CD8 T cell genes by WTD 0.1 nM compared to R5A11D 0.1 nM. N. Heatmap of exhaustion or IL-2 associated genes regulated by WTD at 50 nM and 0.1 nM and R5A11D 0.1 nM.

FIG. 7. Comparison of common gene regulation by IL-10 in monocytes and CD8 T cells. A. Venn diagram comparing genes significantly up or down regulated by wild type IL-10 (50 nM) in monocytes and CD8 T cells. Venn diagram generated using "Venny" (Oliveros, 2007-2015). B. Comparison of the 181 genes regulated by IL-10 in both cell subsets. The $\log_2$ fold change for each gene of WTD (50 nM)/unstimulated in both CD8 T cells and monocytes are plotted. Genes which are upregulated by IL-10 in both cell types are denoted as cluster 1 (C1). Genes upregulated by IL-10 in CD8 T cells but downregulated by IL-10 in monocytes are grouped in cluster 2 (C2). Genes which are upregulated by IL-10 in monocytes but downregulated by IL-10 in CD8 T cells are grouped in cluster 3 (C3). Genes downregulated by IL-10 in both monocytes and CD8 T cells are denoted by cluster 4 (C4). C. Examples of genes from each cluster. The $\log_2$ fold change of WTD (50 nM)/unstimulated in both CD8 T cells and monocytes are plotted. Each point represents one biological replicate and error bars represent the standard deviation.

FIG. 8. Recombinant expression of wild type and high affinity IL-10 monomeric and dimeric variants. A. FPLC chromatogram for wild type and mutant monomer and dimer. Proteins were run on an S200 gel filtration column and separation by size exclusion. B. Coomassie gel of FPLC purified proteins run on 10% gel.

FIG. 9. Biophysical characterisation of high affinity IL-10 variants A. For biacore measurement IL-10Rβ is immobilised on the chip surface via biotin-streptavidin interaction and IL-10 variants are flowed across the chip in solution. B and G. Kinetic charts for IL-10Rβ binding for wild type and high affinity IL-10 with inserts for affinity curves. Concentrations used are shown on curves. C. $K_D$ values for IL-10Rβ binding for wild type and high affinity variants. D. IL-10Rβ is immobilised on the chip surface and IL-10 variants pre-bound to IL-10Rα are flowed across the chip surface in solution. Concentrations used are shown on curves. E and G. Kinetics for IL-10Rβ binding in the presence of IL-10Rα. F $K_D$ values for IL-10Rβ binding when IL-10 proteins are pre-bound to IL-10Rα.

FIG. 10. Single molecule imaging of IL-10 receptors by TIRF microscopy: A. Cell surface receptor density of ectopically expressed IL-10Rα (blue) and IL-10Rβ (red). n=20 cells. B. Diffusion coefficients of IL-10Rα (blue), IL-10Rβ (red) and co-locomoting receptors (magenta) in absence or presence of dimeric and monomeric IL-10 variants. WTD: n=20 cells; R5A11D: n=16 cells, WTM: n=19 cells, R5A11M: n=18 cells, unstimulated: n=10 cells.

Figure 11:
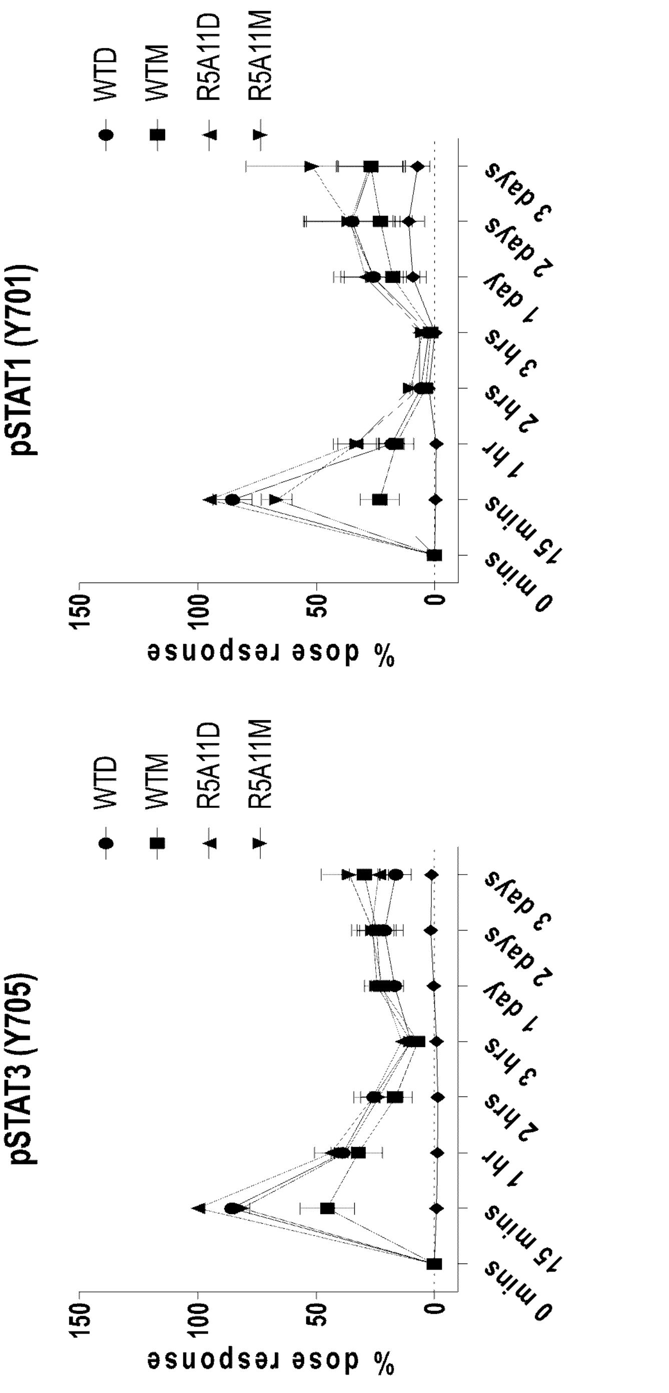

FIG. 11. Extended kinetics of IL-10 and variants in human monocytes. 3-day monocyte pSTAT3/1 kinetics. Monocytes were stimulated with IL-10 for the indicated time periods before fixation. Data shown is the mean of four biological replicates with error bars depicting standard error of the mean. Each biological replicate is normalised by assigning the highest MFI value at 15 mins as 100% and the lowest MFI value of an untreated control as 0%.

FIG. 12. Analysis of gene expression profiles induced by IL-10 wild type and high affinity variants in human monocytes. A. KEGG and GO pathway analysis for genes significantly up or down regulated by WTD 50 nM ≥0.6 or ≤−0.6 $\log_2$ fold change in human monocytes. Pathway analysis done using DAVID Bioinformatics Resource functional annotation tool (Huang da et al., 2009a, Huang da et al., 2009b). B. Heatmap showing $\log_2$ fold change expression by WTD (50 nM) stimulation for a selection of metabolic pathways, cytokine & chemokine, CD and interferon related genes. C. Comparison of $\log_2$ fold change in expression for genes by WTD, WTM and R5A11M at 50 nM and WTD and R5A11D at 0.1 nM concentration. D. Comparison of regulation of monocyte genes by R5A11M 50 nM and WTD 50 nM. The $\log_2$ fold change of R5A11M 50 nM/unstimulated was divided by the $\log_2$ fold change of WTD 50 nM/unstimulated. Proportion of genes which show enhanced regulation by R5A11M are shown in red, proportion of genes which show diminished regulation by R5A11M are shown in blue and genes which do not change between R5A11M and WTD are shown in grey. E. Comparison of regulation of genes by R5A11D 0.1 nM and WTD 0.1 nM. The $\log_2$ fold change of R5A11D 0.1 nM/unstimulated was divided by the $\log_2$ fold change of WTD 0.1 nM/unstimulated. Proportion of genes which show enhanced regulation by R5A11D are shown in red, proportion of genes which show diminished regulation by R5A11D are shown in blue and genes which do not change between R5A11D and WTD are shown in grey.

FIG. 13. Characterisation of the IL-10 treated CD8 T cell phenotype. A. CD8 cells within a PBMC population and purified CD8 cells were stained for CD69 after 24 hours activation and for CD71 after 6 days activation and expansion. Exhaustion markers PD-1 and LAG3 were analysed after 6 days activation and expansion. Fold change was calculated by dividing IL-10 stimulated MFI values by non-IL-10 stimulated controls for each donor. Each point represents one donor. B. Proliferation of CD4 and CD8 T cells in a PBMC population were analysed after 6 days of activation/expansion. Cell counts for CD4+ and CD8+ cells were taken and fold change was calculated by dividing IL-10 treated cells by a non-IL-10 treated control population from the same donor. Each point represents one biological replicate and p values were calculated using a two tailed paired t test. C. CD8 T cells in a purified population were stained for granzyme B. Fold change of granzyme B was calculated by normalising within each biological replicate to a non-IL-10 treated control (TCR stimulated) for both CD8 cells in a PBMC population and purified CD8 cells. mRNA was isolated from a purified CD8 cell population and gzmb mRNA was quantified by RT qPCR. Fold change was calculated by dividing by a non-IL-10 treated control. Each point represents a biological replicate and p values were calculated using two tailed paired t test.

FIG. 14. Analysis of gene expression profiles induced by IL-10 wild type and high affinity variants in human CD8 T cells. A. KEGG and GO pathway analysis for genes significantly up or down regulated by WTD 50 nM ≥0.6 or ≤−0.6 $\log_2$ fold change in human CD8 T cells. Pathway analysis done using DAVID Bioinformatics Resource functional annotation tool (Huang da et al., 2009a, Huang da et al., 2009b). B. Heatmap comparison of regulation of cytokines & chemokines, CD markers, IL-2 related and MAPK signalling genes by WTD, WTM and R5A11M at 50 nM and WTD and R5A11D at 0.1 nM. C. The $\log_2$ fold change of R5A11M 50 nM/unstimulated was divided by the $\log_2$ fold change of WTD 50 nM/unstimulated. Proportion of genes which show enhanced regulation by R5A11M are shown in red, proportion of genes which show diminished regulation by R5A11M are shown in blue and genes which do not change between R5A11M and WTD are shown in grey. D. Comparison of regulation of genes by R5A11D 0.1 nM and WTD 0.1 nM. The $\log_2$ fold change of R5A11D 0.1 nM/unstimulated was divided by the $\log_2$ fold change of WTD 0.1 nM/unstimulated. Proportion of genes which show enhanced regulation by R5A11D are shown in red, proportion of genes which show diminished regulation by R5A11D are shown in blue and genes which do not change between R5A11D and WTD are shown in grey.

Figure 15A:
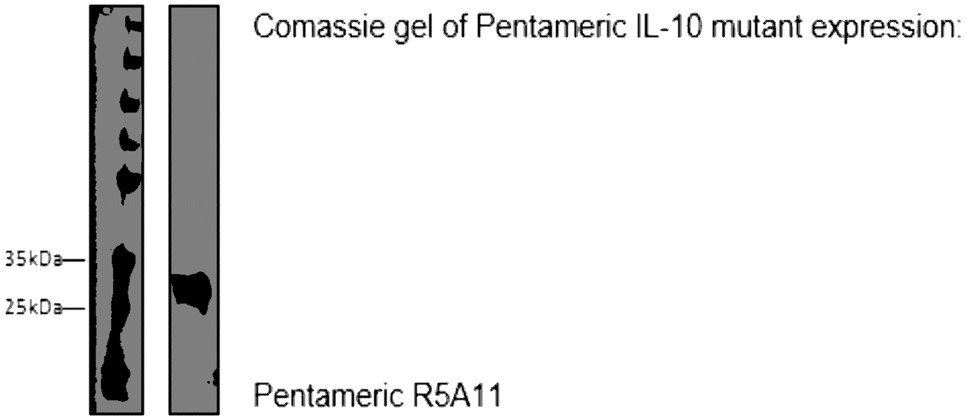
Figure 15B:
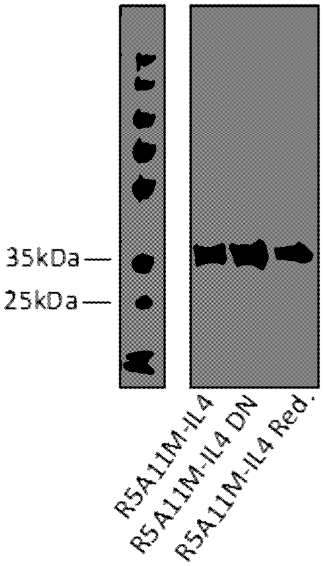

FIG. 15 Generation of pentameric IL-10 and fusion versions of IL-10 with IL-4 wt and mutant forms. A. A gel showing the generation of the pentameric form of IL-10 mutein. B. A gel showing the generation of various IL-10 mutein/IL-4 fusions.

Figure 16A:
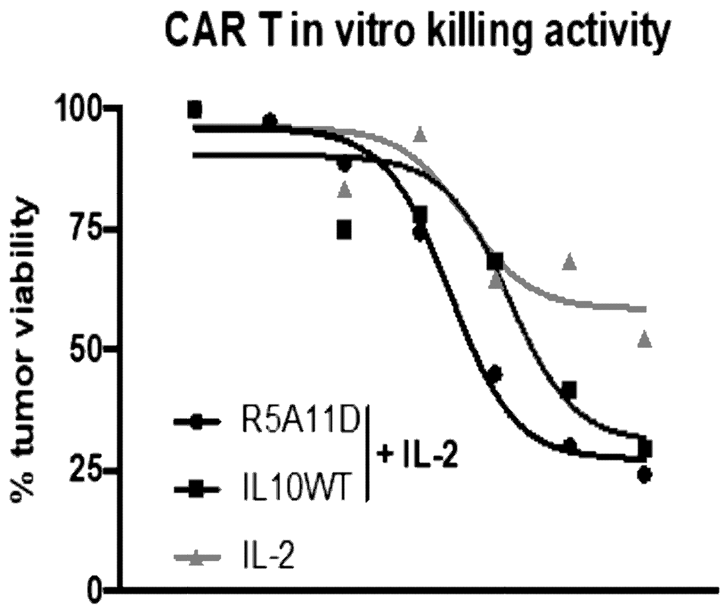

FIG. 16 CAR T experiments using WT and IL-10 muteins. A. A graph showing the effect increasing concentrations of wt IL-10 and IL-10 mutein has on CAR Tin vitro tumour viability, as compared to IL-2. B. A graph showing interferon gamma production by CAR T cells following addition of wt and mutant forms of IL-10.

MATERIAL AND METHODS

Protein Expression and Purification

Monomeric wild type IL-10 (Josephson et al., 2000), monomeric high affinity variants and IL-10Ra ectodomain (amino acids 22-235) were cloned and expressed as described in (Martinez-Fabregas et al., 2019). Briefly, protein sequences were cloned into the pAcGP67-A vector (CD Biosciences) in frame with an N-terminal gp67 signal sequence, driving protein secretion, and a C-terminal hexahistidine tag. The baculovirus expression system was used for protein production as outlined in (LaPorte et al., 2008). *Spodoptera frugiperda* (SF9) cells, grown in SF90011 media (Invitrogen), were transfected to produce Po baculovirus stocks that were then expanded in SF9 cells to produce Pi virus stock. Protein expression was performed using *Trichoplusiani ni* (High Five) with cells grown in InsectXpress media (Lonza).

Purification was performed using the method described in Sprangler et al (2019). Briefly, the cells were pelleted with centrifugation at 2000 rpm, prior to a precipitation step through addition of Tris pH 8.0, $CaCl_2$ and NiCl to final concentrations of 200 mM, 50 mM and 1 mM. The precipitate formed was then removed through centrifugation at 6000 rpm. Nickel-NTA agarose beads (Qiagen) were added and the target proteins purified through batch binding followed by column elution in HBS, 200 mM imidazole, pH 7.2. Target proteins were concentrated and further purified by size exclusion chromatography on an ENrich SEC 650 300 column (Biorad), equilibrated in 10 mM HEPES (pH 7.2), 150 mM NaCl. IL-10Rα was biotinylated using EZ=Link NHS biotinylation kit (Thermo) according to the manufacturer's protocols.

For expression of biotinylated IL-10Rβ the ectodomain (amino acids 20-220) was cloned into the pAcGP67-A vector carrying a C-terminal biotin acceptor peptide (BAP)-LNDIFEAQKIEWHW followed by a hexahistidine tag. The purified protein was biotinylated with BirA ligase.

For expression of dimeric wild type IL-10 and dimeric high affinity variants, synthesised gene blocks (IDT) were cloned into the pET21 vector in frame with an N-terminal hexahistidine tag and a lac promotor, and transformed into *E. Coli* BL21 cells. Protein production was induced using 1 mM final concentration of IPTG (Formedium) followed by incubation at 37° C. for 3 to 5 hours. Cells were harvested by centrifugation at 6000×g for 15 minutes. The cell pellets were resuspended in 50 mM Tris-HCl (pH 8.0), 25% (w/v) sucrose, 1 mM Na EDTA, 10 mM DTT, 0.2 mM PMSF per litre of original culture and frozen at −80° C. overnight.

The recombinant protein was expressed as inclusion bodies, purification of which was performed as follows. Cells were lysed in 100 mM Tris-HCl (pH 8.0), 2% (v/v) TritonX-100, 200 mM NaCl, 2500 units Benzonase, 10 mM DTT, 5 mM MgCl2, 0.2 mM PMSF and incubated for 20 minutes with stirring at room temperature. 10 mM EDTA final concentration was then added to the suspension and the cells were sonicated (8-10 cycles of 15 seconds on/off, 15 microns, Soniprep 150) in an ice bath. The solution was centrifuged at 7000×g for 15 mins (4° C.) and resuspended in 50 mM Tris-HCl pH 8.0, 0.5% Triton X-100, 100 mM NaCl, 1 mM Na EDTA, 1 mM DTT, 0.2 mM PMSF. This step was repeated for a total of at least three washes until the preparation appeared white. The final pellet was then washed once in detergent free buffer (50 mM Tris-HCl pH 8.0, 1 mM Na EDTA, 1 mM DTT, 0.2 mM PMSF).

The purified inclusion bodies were solubilised in 10 mls of 6M GuHCl per litre of original culture, for 30 minutes at room temperature. The solution was clarified by a centrifugation at 7000 rcf for 15 minutes and the solubilised protein carefully decanted. Refolding was performed through dropwise addition of the solubilised protein solution into refolding buffer (50 mM Tris-HCl, pH 8.0, 50 mM NaCl, 5 mM EDTA, 2 mM reduced glutathione (GSH) and 0.2 mM oxidized glutathione (GSSG)) at a ratio of 1:20 solution: buffer at 4° C. followed by incubation with gentle stirring overnight at 4° C.

The solution was then filtered to remove any precipitant and dialysis performed against 10 mM HEPES (pH 7.2), 150 mM NaCl, using dialysis membrane with a 14 kDa Mwt cut off.

After dialysis protein was then further purified using Ni-NTA beads and by size exclusion on a Superdex75 increase 10/300 column (GE Healthcare). Endotoxin removal was then performed. 1 mL of Ni-NTA agarose was added to a polyprep column and equilibrated with 10 mls of HBS before addition of the protein. The column was washed with 50 column volumes of ice-cold HBS, 150 mM NaCl, 20 mM imidazole, 0.1% Triton-X114 (pH X) to remove endotoxin. The column was then washed with a further 20 column volumes of HBS, 20 mM imidazole (pH X). The now endotoxin-free protein was eluted using 4 column volumes of HBS, 200 mM imidazole (pH X). The protein was buffer exchanged into 10 mM HEPES, 150 mM NaCl (pH 7.2), using PD-10 columns (GE Healthcare). Endotoxin levels were measured using Pierce LAL Chromogenic Endotoxin Quantitation Kit (Thermo) following the manufacturer's protocol. For all proteins endotoxin levels were below detection levels of the kit.

Surface Plasmon Resonance

Surface plasmon resonance was used to determine the binding affinity of the recombinantly produced monomeric IL-10 wild type and variants to IL-10Rβ in the presence or absence of IL-10Rα. Biotinylated IL-10Rβ was immobilised onto the chip surface via streptavidin. Series S Sensor SA (GE Healthcare) chips were primed in 10 mM HEPES, 150 mM NaCl, 0.02% TWEEN-20, prior to immobilisation of the biotinylated receptor. Analysis runs were then performed in 10 mM HEPES, 150 mM NaCl, 0.05% TWEEN-20 and 0.5% BSA. A Biacore T100 (T200 Sensitivity Enhanced) was used for measurement with Biacore T200 Evaluation Software 3.0 used for data analysis.

Cell Culture

Human buffy coats were obtained from the Scottish Blood Transfusion Service and peripheral blood mononuclear cells (PBMCs) were isolated by density gradient centrifugation (Lymphoprep, StemCell Technologies). PBMCs were grown in RPMI-1640, 10% v/v FBS, 100 U/mL penicillin-streptomycin (Gibco) and cytokines for proliferation and activation. For three days media was supplemented with 100 ng/mL anti-CD3 (human UltraLEAF, Biolegend) and 20 ng/mL IL-2 (Proleukin, Novartis) in the absence or presence of IL-10 variants. After three days activation cells were centrifuged and resuspended in media supplemented with 20 ng/mL of IL-2 plus or minus IL-10 variants. Cell populations were allowed to expand for 2-3 days.

Monocytes were isolated from PBMC populations using CD14 positive selection. Anti-$CD14^{FITc}$ antibody (Biolegend #367116) was used to stain cells and isolation was done by magnetic separation following manufacturer's protocol (MACS Miltenyi). Monocytes were then cultured in complete RPMI (as above) supplemented with M-CSF (20 ng/mL, Biolegend). Cells were then stimulated with IL-10 variants for twenty-four hours before analysis.

CD8 T cells were isolated from PBMCs by magnetic separation (MACS Miltenyi) after staining with anti-$CD8a^{FITC}$ antibody (Biolegend #30906). For activation of purified CD8 T cells ImmunoCult Human CD3/CD28 T cell Activator (Stem Cell) was used following manufacturer's protocol as well as the addition of 20 ng/mL IL-2 and IL-10 variants. Cells were activated for 3 days and then the media was replaced with complete RPMI supplemented with 20 ng/mL IL-2 as well as IL-10 variants for 2-3 days.

Flow Cytometry Staining and Antibodies

For live cell surface staining of $HLA\text{-}DR^{PE}$ (Biolegend #307605) non-adherent monocytes were removed from culture by centrifugation and resuspension in cold PBS. Adherent monocytes were detached using Acutase (StemCell Technologies) at room temperature for 5 to 10 minutes. Cells were kept at 4° C. or on ice during live cell surface marker staining and staining was done in 96-well v-bottom plates (Griener) unless otherwise stated. Non-adherent and detached cells were combined and resuspended in FcR blocking reagent (Miltenyi) for 10 minutes at 4° C. in a volume of 50 μL per condition. Cells were washed in PBS/0.5% BSA and resuspend in 50 μL of antibody mixture diluted 1/100 in FcR blocking reagent. Antibody incubation was done for 30 to 60 minutes at 4° C. in the dark. Cells were washed twice before resuspension in 100 μL per well for analysis on the CytoFlex flow cytometer (Beckman Coulter). Mean fluorescence intensity (MFI) was quantified for all populations. Data was normalised within each donor by dividing MFI of IL-10 treated cells by a non-IL-10 treated control from the same donor to calculate fold change.

For granzyme B intracellular staining either PBMCs or CD8 cells on day 6 of activation were fixed with 2% paraformaldehyde for 10 minutes at room temperature before washing in PBS. Cells were permeabilised in 0.1% Triton-X100/PBS for 10 minutes and washed in PBS/0.5% BSA. Cells were stained with anti-CD8a$^{AlexaFluor700}$ (Biolegend #300920), anti-CD4$^{PE}$ (Biolegend #357404), anti-CD3$^{BrilliantViolet510}$ (Biolegend #300448) and anti-granzyme B$^{FITC}$ (Biolegend #515403) at 1/100 dilution for one hour before washing. MFI was quantified for all populations and normalisation was done as described above.

For phospho-flow analysis of STAT1 and STAT3 cells were plated at 50 μL of cell suspension per well at a density of 2×10$^4$ cells per well in 96-well V bottom plates. For does response studies cells were simulated with 7-fold serially diluted IL-10 variants and an unstimulated control (50 μL per well) for 15 minutes at 37° C. before fixation with 2% paraformaldehyde for 10 minutes at room temperature. For kinetic studies, cells were stimulated with a saturating concentration of IL-10 variants (50 nM) at defined time points before fixation simultaneously with 2% paraformaldehyde. Cells were washed in PBS and permeabilised in ice-cold 100% methanol and incubated on ice for a minimum of 30 minutes. Cells were fluorescently barcoded as described in (Krutzik and Nolan, 2006; Martinez-Fabregas et al., 2019). Briefly, a panel of 16 combinations of two NHS-dyes (Pacific Blue and DyLight800, Thermo) were used to stain individual wells on ice for 35 minutes before stopping the reaction by washing in PBS/0.5% BSA. Once barcoded the 16 populations were be pooled together for antibody staining. PBMCs, CD8 cells and monocytes were stained with the cell surface markers described above as well as anti-pSTAT3$^{Alexa488}$ (Biolegend #651006) and anti-pSTAT1$^{Alexa647}$ (Cell Signalling Technologies #8009). During acquisition individual populations were identified according to the barcoding pattern and pSTAT3$^{Alexa488}$ and pSTAT1$^{Alexa647}$ MFI was quantified for all populations. MFI was plotted and sigmoidal dose response curves were fitted using Prism software (Version 7, GraphPad). Data was normalised by assigning the highest MFI of the top concentration of all stimuli as 100% and the lowest MFI as 0% within each donor group.

Yeast Display Library

Yeast surface display protocol was adapted from previous protocols (Boder and Wittrup, 1997; Martinez-Fabregas et al., 2019). To create an IL-10 yeast display library the monomeric IL-10 gene (Josephson et al., 2000) was subject to error-prone PCR as described in (Mendoza et al., 2017). This product was then amplified and transformed along with a linearized pCT302 vector into the *Saccharomyces cerevisiae* stain EBY100 and grown in selective dextrose casamino acids (SDCAA) media at 30° C. for two days. Yeast cells were then place in selective galactose casamino acids (SGCAA) at 20° C. for two days to induce cell surface expression of IL-10 variants as described in (Chao et al., 2006). Magnetic activated cell sorting (MACS, Miltenyi) was used to select for IL-10 variants with increased binding affinity for IL-10Rβ as described previously for other systems (Moraga et al., 2015b). Briefly, the first round of selection was performed using high concentrations of streptavidin beads to remove any yeast which displayed variants capable of binding streptavain. The second round of selection selected for yeast which display variants with the c-myc tag at their C-terminus, ensuring that displayed proteins were properly folded. The subsequent rounds of selection were carried out by incubating induced yeast with decreasing concentrations of recombinantly produced biotinylated IL-10Rβ for 2 hours followed by a 15 minute incubation with fluorescently labelled streptavidin (AlexaFluor647). Magnetic activated cell sorting (MACS, Miltenyi) selected for yeast which displayed IL-10 variants capable of binding IL-10Rβ. Once the concentration of IL-10Rβ needed for binding was decreased sufficiently compared to wild type monomeric IL-10, the yeast were plated on SDCAA agar and single colonies were isolated for dose response studies to determine the EC50 values of the mutants.

Yeast colonies displaying promising IL-10 variants were subject to Zymoprep (ZymoResearch) to isolate the plasmid which was then heat shocked into competent DH5a *E. coli* and plasmids were sequenced to observe where mutations had occurred in the monomeric IL-10 gene. These genes were then cloned into the baculovirus expression vector pACgp67BN and recombinantly expressed as described above.

Measurement of IL-6 Secretion

Monocytes were stimulated with LPS (100 ng/mL) (*E. coli* 026:B6, Sigma) plus IL-10 variants at various concentration for 8 hours. Supernatant was then removed and used for enzyme linked immunosorbent assay (ELISA) for IL-6 detection (Biolegend, #430501). Manufacturer's protocol was followed. 96-well half-area plates (Sigma) were coated in capture antibody and incubated overnight at 4° C. Plates were washed in PBS/0.05% Tween-20 and blocked for 1 hour in assay diluent and washed. Supernatant was diluted 1 to 10 in assay buffer before addition to the plate. The plates were incubated at room temperature for two hours with shaking. Plates were washed again and incubated for 1 hour with detection antibody. After washing, avidin-HRP was added and incubated for 30 minutes followed by incubation with TMB substrate solution for 15 minutes. The reaction was stopped by addition of $H_2SO_4$ and absorbance was measured at 450 nm and 570 nm with absorbance at 570 nm being subtracted from 450 nm.

RNA Transcriptome Sequencing

Human primary monocytes and CD8 T cells from three donors each (StemCell Technologies) were stimulated as described in above. Cells were washed in Hank's balanced salt solution (H BSS, Gibco) and snap frozen for storage. RNA was isolated using the RNeasy Kit (Quiagen) according to manufacturer's protocol. All RNA 260/280 ratios were above 1.9. 1 μg of RNA was used per sample. Transcriptomic analysis was done by Novogene as follows. Sequencing libraries were generated using NEBNext® Ultra™ RNALibrary Prep Kit for Illumina® (NEB, USA) following manufacturer's recommendations and index codes were added to attribute sequences to each sample. Briefly, mRNA was purified from total RNA using poly-T oligo-attached magnetic beads. Fragmentation was carried out using divalent cations under elevated temperature in NEB- Next First StrandSynthesis Reaction Buffer (5×). First strand cDNA was synthesized using random hexamer primer and M-MuLV Reverse Transcriptase (RNase H−). Second strand cDNA synthesis was subsequently performed using DNA Polymerase I and RNase H. Remaining overhangs were converted into blunt ends via exonuclease/polymerase activities. After adenylation of 3' ends of DNA fragments, NEBNext Adaptor with hairpin loop structure were ligated to prepare for hybridization. In order to select cDNA fragments of preferentially 150-200 bp in length, the library fragments were purified with AMPure XP system (Beckman Coulter, Beverly, USA). Then 3 μl USER Enzyme (NEB, USA) was used with size-selected, adaptor-ligated cDNA at 37° C. for 15 min followed by 5 min at 95° C. before PCR. Then PCR was performed with Phusion High-Fidelity DNA polymerase, Universal PCR primers and Index (X) Primer. At last, PCR products were purified (AMPure XP system) and library quality was assessed on the Agilent Bioanalyzer 2100 system.

RNA Sequencing Data Analysis

Primary data analysis for quality control, mapping to reference genome and quantification was conducted by Novogene as outlined below.

Quality control: Raw data (raw reads) of FASTQ format were firstly processed through in-house scripts. In this step, clean data (clean reads) were obtained by removing reads containing adapter and poly-N sequences and reads with low quality from raw data. At the same time, Q20, Q30 and GC content of the clean data were calculated. All the downstream analyses were based on the clean data with high quality.

Mapping to reference genome: Reference genome and gene model annotation files were downloaded from genome website browser (NCBI/UCSC/Ensembl) directly. Paired-end clean reads were mapped to the reference genome using HISAT2 software. HISAT2 uses a large set of small GFM indexes that collectively cover the whole genome. These small indexes (called local indexes), combined with several alignment strategies, enable rapid and accurate alignment of sequencing reads.

Quantification: HTSeq was used to count the read numbers mapped of each gene, including known and novel genes. And then RPKM of each gene was calculated based on the length of the gene and reads count mapped to this gene. RPKM, (Reads Per Kilobase of exon model per Million mapped reads), considers the effect of sequencing depth and gene length for the reads count at the same time and is currently the most commonly used method for estimating gene expression levels.

Statistical analysis was done by the authors in Excel. The fold change was calculated by dividing the IL-10 stimulated expression levels by the unstimulated control within each donor. The average fold change was calculated for each stimulation across the three donors and the $\log_2$ of this average was then calculated. For calculation of significantly changed genes, the $\log_2$ of the fold change between IL-10 stimulated and unstimulated expression levels of each donor was calculated, separately and an unpaired, two tailed t test was used to generate the p value. The logo of this p value was then plotted against the previously calculated $\log_2$ average fold change. Genes which were significantly ($p \leq 0.05$) changed greater than 0.6 or less than −0.6 $\log_2$ fold change in the wild type IL-10 dimer (WTD) 50 nM condition were taken as a set list of genes against which all other IL-10 stimulations were compared. Upregulated genes were denoted as genes ≥0.6 $\log_2$ fold change and downregulated genes were denoted as genes ≤−0.6 $\log_2$ fold change. For comparison of WTD to other IL-10 variant stimulations the average $\log_2$ fold changes of the variant was divided by the average $\log_2$ fold change of WTD. Genes with an RPKM of less than 1 in two or more donors were excluded from analysis so as to remove genes with abundance near detection limit.

Functional annotation of genes (KEGG pathways, GO terms) was done using DAVID Bioinformatics Resource functional annotation tool (Huang da et al., 2009a, b). Clustered heatmap was generated using R Studio Pheatmap package.

Live-Cell Dual Colour Single Molecule Imaging Studies

Receptor homo- and heterodimerization was quantified by two-colour single-molecule co-tracking as described previously (Moraga et al., 2015c, Wilmes et al., 2015, Wlmes et al., 2020). Receptor dimerization experiments were performed in HeLa cells transiently expressing IL-10Rα and IL-10Rβ with N-terminally fused variants of monomeric ECFP and EGFP, respectively. Cell surface Labelling was achieved using anti-GFP nanobodies Minimizer (MI) and Enhancer (EN), respectively, site-specifically conjugated with photostable fluorophores via an engineered cysteine residue. For quantification of receptor heterodimerization, IL-10Rα and IL-10Rβ were labelled with $MI^{Rho11}$ (ATTO Rho11, ATTO-TEC GmbH) and $EN^{AT643}$ (ATTO 643, ATTO-TEC GmbH), respectively. For quantification of homodimerization, either IL-10Rα was labelled with $MI^{Rho11}$ and $MI^{AT643}$, or IL-10Rβ was labelled with $EN^{Rho11}$ and $EN^{AT643}$. Over-expression of the corresponding other receptor subunit was ensured by labelling with $EN^{AT488}$ or $MI^{AT488}$ (ATTO 488, ATTO-TEC GmbH), respectively. Time-lapse dual-color imaging of individual IL-10Rα and IL-10Rβ in the plasma membrane was carried out by total internal reflection fluorescence microscopy with excitation at 561 nm and 640 nm and detection with a single EMCCD camera (Andor iXon Ultra 897, Andor) using an image splitter (QuadView QV2, Photometrics). Molecules were localized using the multiple-target tracing (MTT) algorithm (Serge et al., 2008). Receptor dimers were identified as molecules that co-localized within a distance threshold of 150 nm for at least 10 consecutive frames as described in detail previously (Moraga et al., 2015c, Wilmes et al., 2015, Wilmes et al., 2020).

Results:

Engineering IL-10 Variants with Enhanced Affinity Towards IL-10Rβ

IL-10 engages its tetrameric receptor complex in a two-step binding process. In a first step one molecule of IL-10 binds two copies of IL-10Rα with high affinity and in a second step, two copies of IL-10Rβ are recruited to the tetrameric IL-10/IL-10Rα complex to initiate signalling (FIG. 1A, top panel). A striking feature of IL-10 is its very poor binding affinity for IL-10Rβ (~mM range), which we hypothesised acts as a rate-limiting step in IL-10's biological activities. Thus, we asked whether an IL-10Rβ affinity-enhanced IL-10 variant would overcome this in vivo rate-limiting-step by inducing robust responses at a wide range of ligand concentrations. To address this question, we have used yeast surface display to increase the binding affinity of IL-10 for IL-10Rβ and study the signalling and activity profiles induced by these new affinity-enhanced IL-10 variants. A caveat to engineering IL-10 is its dimeric nature, which makes the correct display of this cytokine on the yeast surface challenging. We have used the monomeric IL-10 variant previously described by the Walter group (Josephson et al., 2000) as an engineering scaffold to overcome this limitation. The monomeric IL-10 was generated by the Walter group by extending the connecting linker between helices D and E in IL-10 by 6 peptides, consequently allowing helices E and F to fold into its own hydrophobic core to form an IL-10 monomer (FIG. 1B and FIG. 8). Monomeric IL-10 recruits one molecule each of IL-10Rα and IL-10Rβ to form an active signalling trimeric complex (FIG. 1A, bottom panel). Although monomeric IL-10 can trigger IL-10-mediated responses, it does so with a significantly lower potency than its dimeric counterpart (Josephson et al., 2000, Logsdon et al., 2002).

Figure 1G:
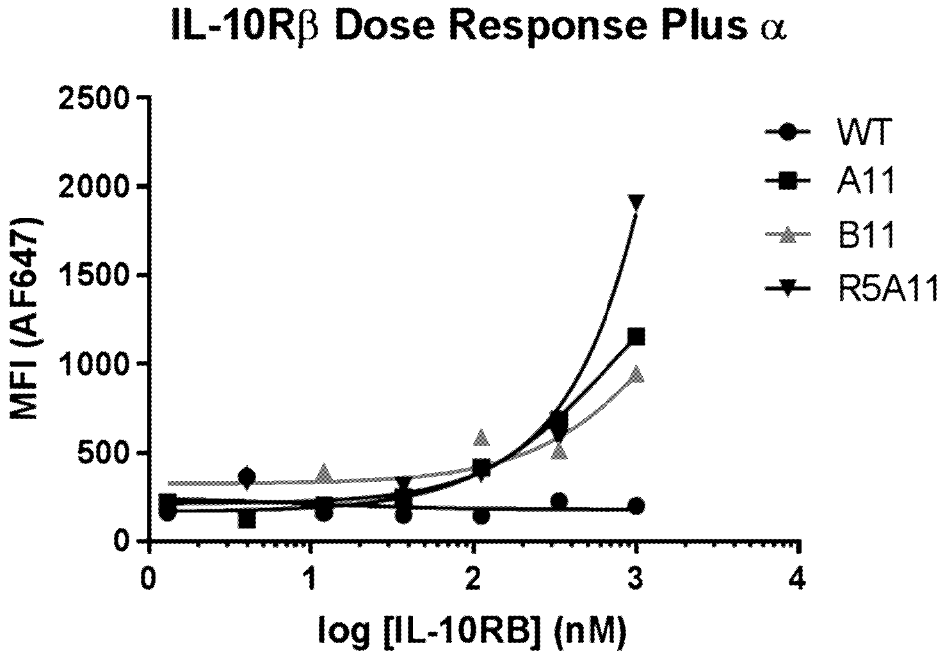
Figures 1, 1I:
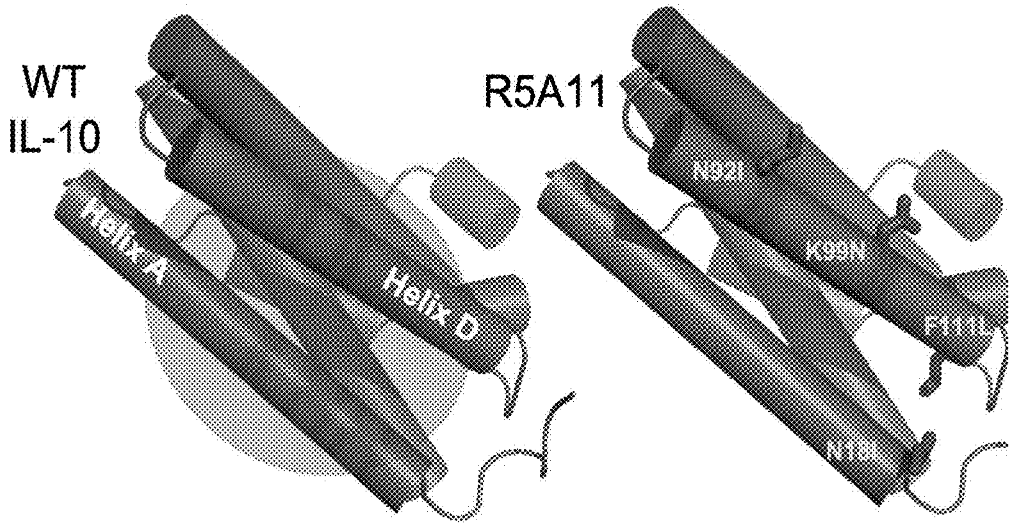
Figure 1J:
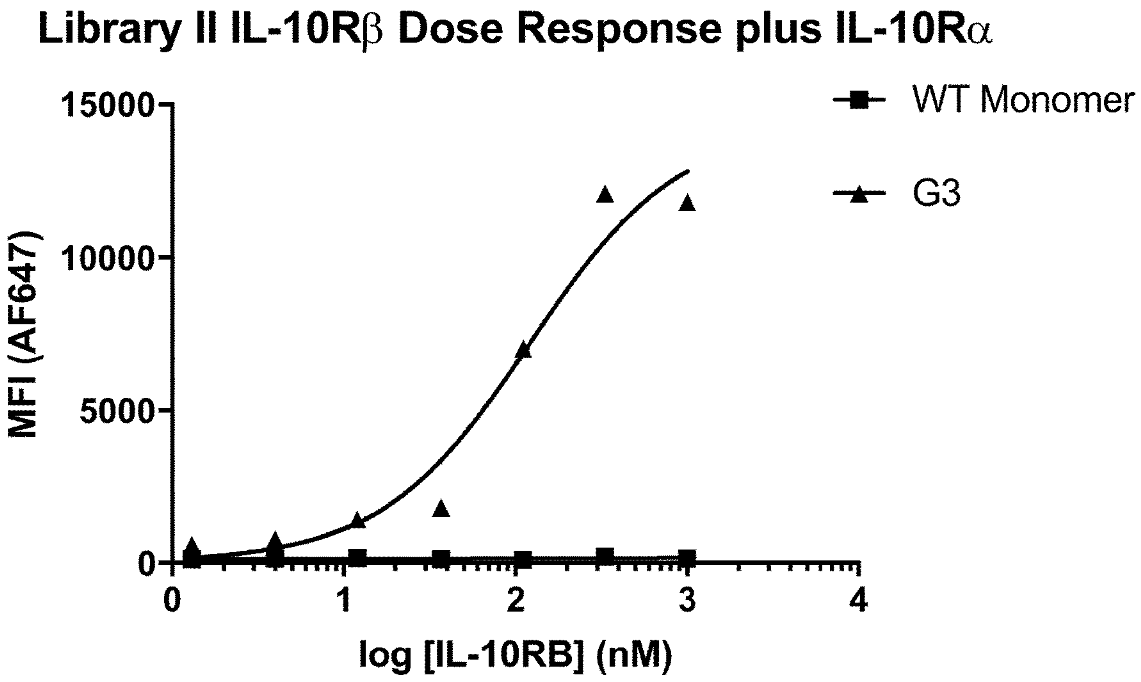

First, we transfected yeast with the monomeric IL-10 construct to test whether binding to IL-10Rα and IL-10Rβ receptor subunits was preserved in the context of the yeast surface. We used biotinylated IL-10Rα and IL-10Rβ receptors in combination with Alexa-647 fluorescently labelled streptavidin to measure receptor binding by flow cytometry (FIG. 1C). As shown in FIG. 1D monomeric IL-10 retained binding to IL-10Rα confirming that it was correctly displayed on the surface of the yeast. We could not detect binding of monomeric IL-10 to IL-10Rβ in the presence or absence of IL-10Rα confirming its weak binding to this receptor subunit (FIG. 1D). Without a crystal structure of IL-10 bound to IL-10Rβ to guide us in the design of a site-directed mutant library, we undertook an unbiased error-prone approach to generate IL-10 mutants with enhanced affinity for IL-10Rβ. The monomeric IL-10 variant was subject to error-prone PCR and the amplified PCR product was electroporated into the *S. cerevisiae* strain EBY100 following previously described protocols (Chao et al., 2006, Mendoza et al., 2017). Eight rounds of selection were performed where the concentration of IL-10Rβ was gradually decreased to isolate variants of IL-10 that bind IL-10Rβ with enhanced affinity (FIG. 1E). Initial rounds of selection were done with high concentrations of biotinylated IL-10Rβ in the presence of non-biotinylated IL-10Rα to stabilize the surface complex and recover low affinity binders. After round 6 the library was comprised of variants that could bind IL-10Rβ in the absence of IL-10Rα and by round 8 the library could bind concentrations of IL-10Rβ in the low nanomolar range (FIGS. 1E and 1F). At this point we picked individual yeast colonies and isolated several clones (A11, B11, R5A11) that bound IL-10Rβ with enhanced affinity when compared to IL-10 wild-type (FIGS. 1F and 1G). When the mutations found in these variants were placed in the context of the IL-10 structure, importantly they localized in a region along helices A and D previously predicted to bind IL-10Rβ (Mendoza et al., 2017) validating our selection process (FIGS. 1H and 1I).

Biophysical Characterisation of Isolated IL-10 Variants

Figure 8A:
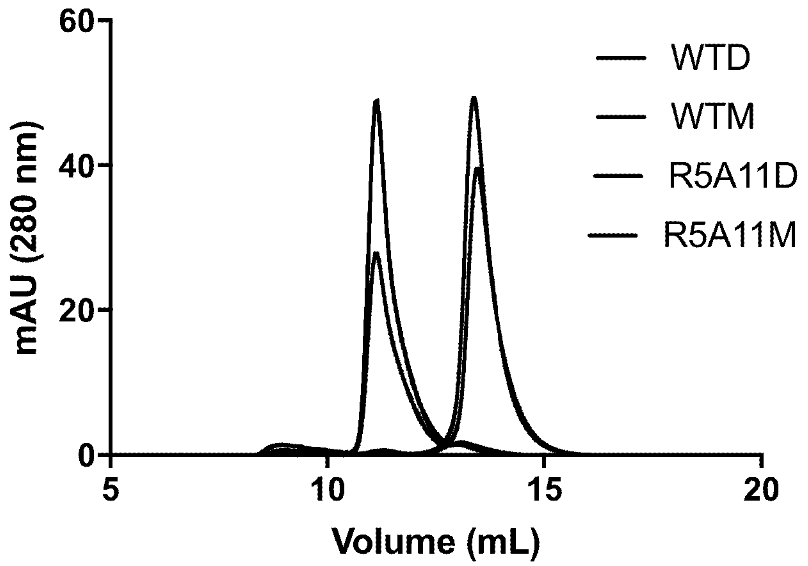
Figure 8B:
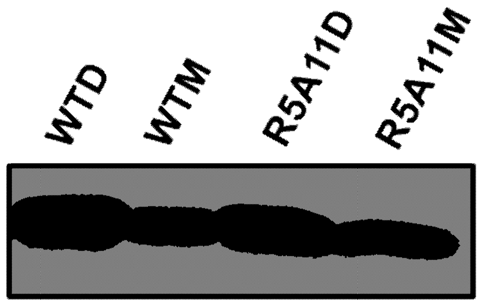
Figure 9A:
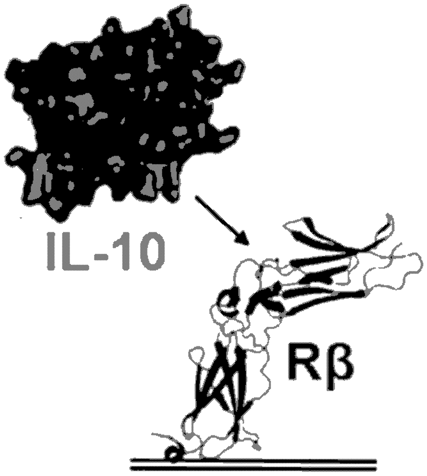
Figure 9A:
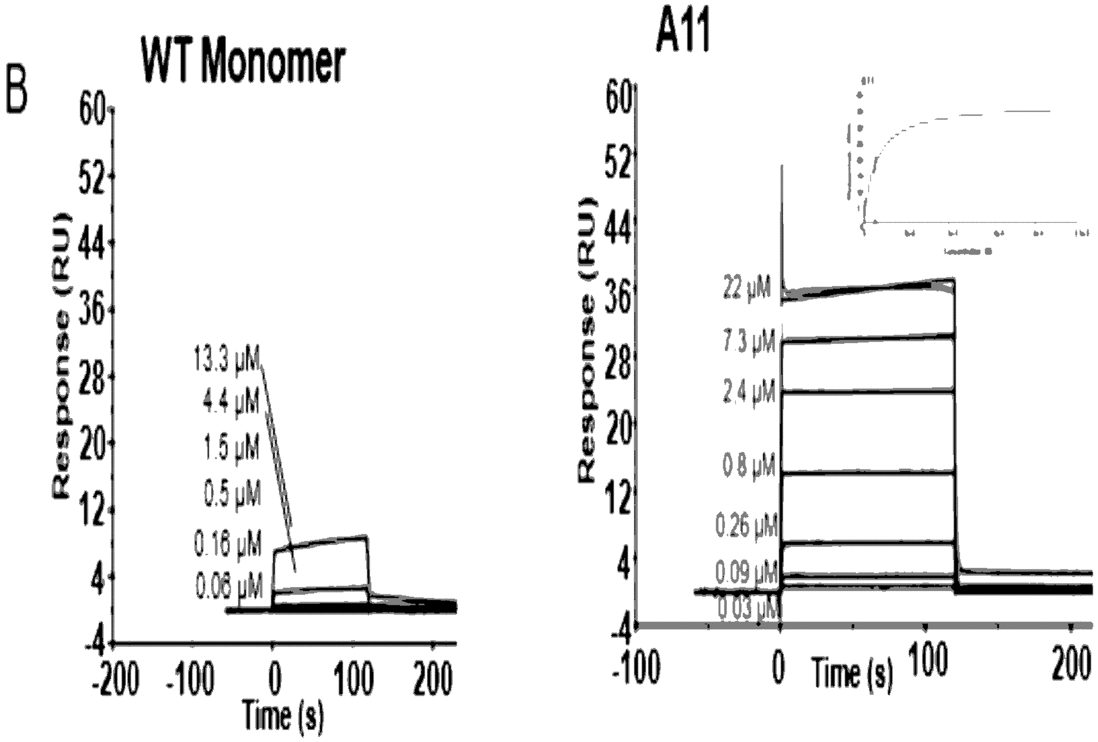
Figure 9B:
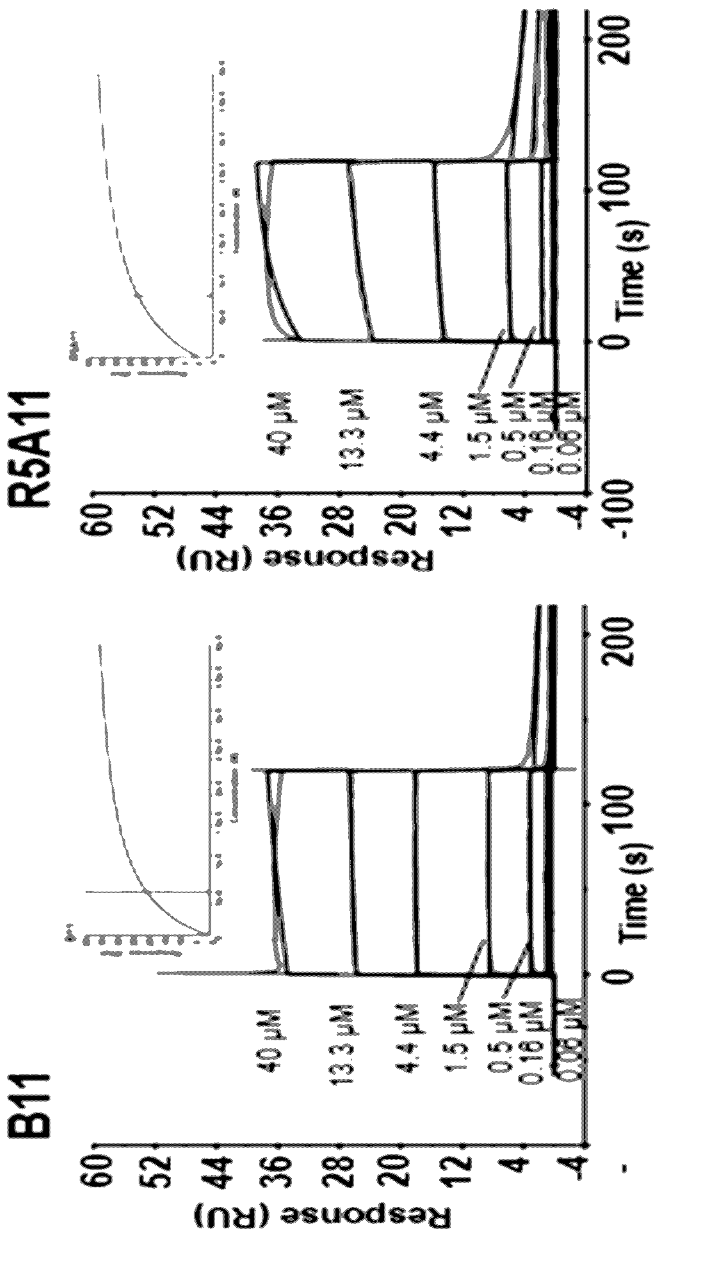

Next we recombinantly expressed the isolated IL-10 variants and characterized their biophysical properties. Importantly, the IL-10 variants behave as monomers when run in a gel filtration column confirming their monomeric nature (FIGS. 8A and 8B). We carried out surface plasmon resonance (SPR) studies to validate the apparent binding affinities seen in the on-yeast binding titration experiments in FIG. 1G. Biotinylated IL-10Rβ was immobilised onto the chip surface and the IL-10 variants A11, B11 and R5A11 were flowed across (FIG. 9A). We could not detect binding of the wild type monomeric IL-10 (WTM) at the range of doses used in this study (micromolar range), confirming the low binding affinity exhibited by IL-10 wt for IL-10Rβ (FIGS. 9B, panel one and 9C). The affinity matured IL-10 variants were all capable of binding IL-10Rβ with $K_D$ values in the low micromolar range (FIGS. 9B and 9C) confirming their improved binding affinities.

Figures 9C, 9D:
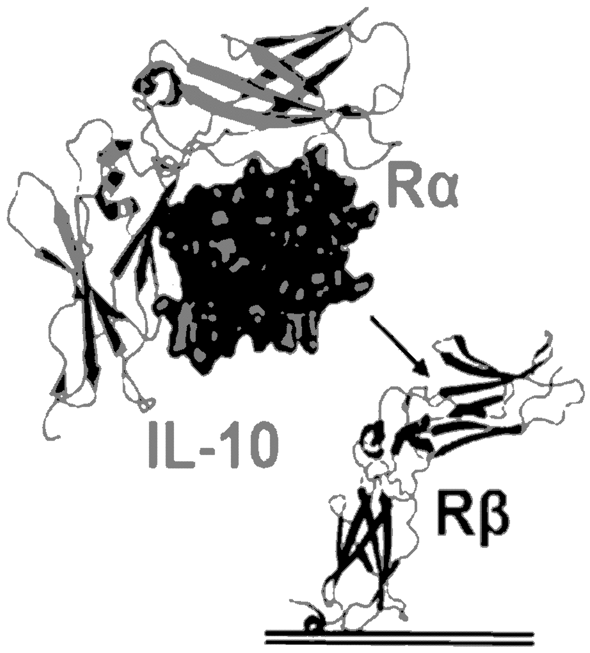
Figure 9E:
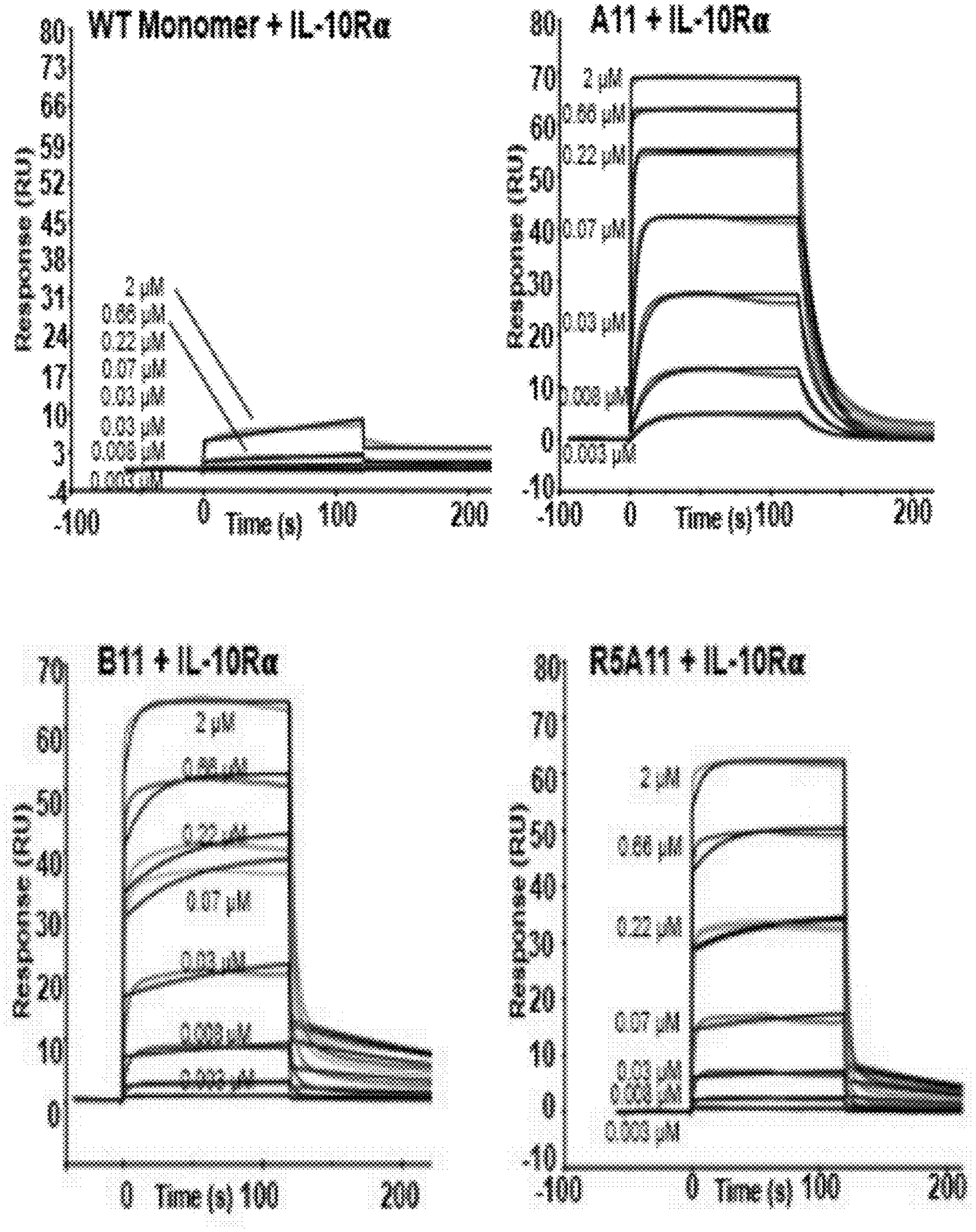
Figures 9F, 9G:
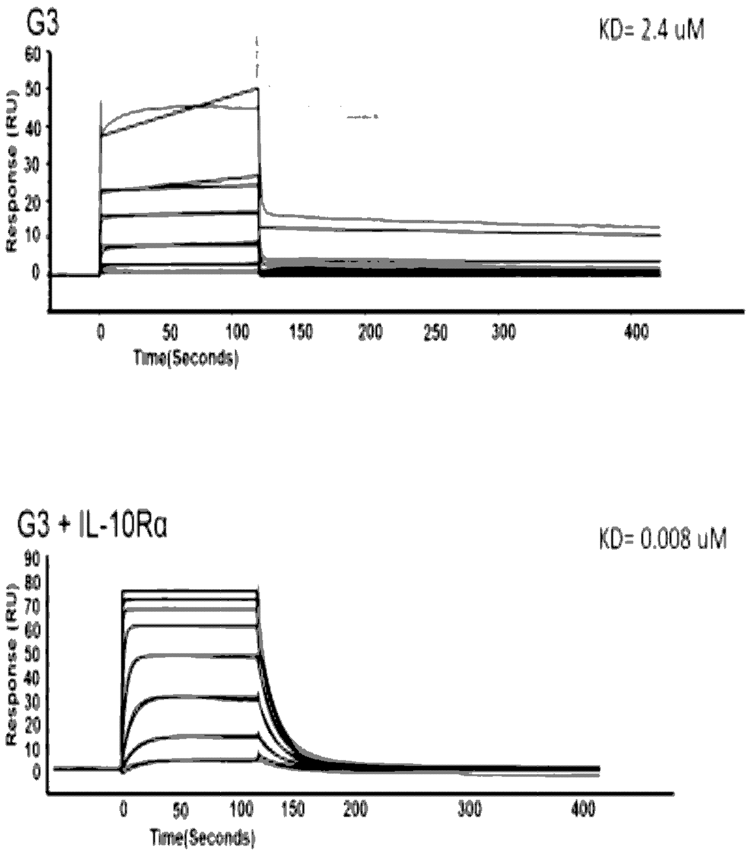

IL-10 displays cooperative binding kinetics whereby its affinity for IL-10Rβ is enhanced once pre-bound to IL-10Rα (Walter, 2014). Thus, we investigated whether our mutants preserved this property. For that, we performed new SPR measurements using the high affinity IL-10 variants pre-bound to soluble IL-10Rα (FIG. 9D). We could not detect significant binding of the WTM/IL-10Rα complex to IL-10Rβ, highlighting again its very poor binding affinity towards IL-10Rβ (FIGS. 9E, panel one and 9F). All IL-10 variants exhibited enhanced binding to IL-10Rβ when complexed to IL-10Rα (in the nM range), confirming their cooperative binding and suggesting that the canonical IL-10 receptor complex binding topology has not been perturbed by the mutations introduced in our new variants (FIGS. 9E and 9F). Our SPR data confirms the isolation of new IL-10 variants, which engage IL-10Rβ with 1000-fold better binding affinity than their wt counterpart.

Enhanced IL-10Rβ Binding Affinity Improves Receptor Complex Assembly.

Thus far we had carried out the biophysical characterisation of our high affinity IL-10 variants in the monomeric conformation of the cytokine as this was necessary for the protein engineering methodologies used. In order to recapitulate the native IL-10/IL-10 receptor complex stoichiometry we recombinantly expressed our high affinity IL-10 mutant, R5A11, in the dimeric form (R5A11D) in addition to the monomeric form (R5A11M) (FIGS. 8A and 8B). Comparisons between this and the wild type IL-10 dimer (WTD) and wild type IL-10 monomer (WTM) allowed us to examine the contributory effects of increased binding affinity as well as stoichiometry on IL-10's molecular and cellular activities.

Figure 2A:
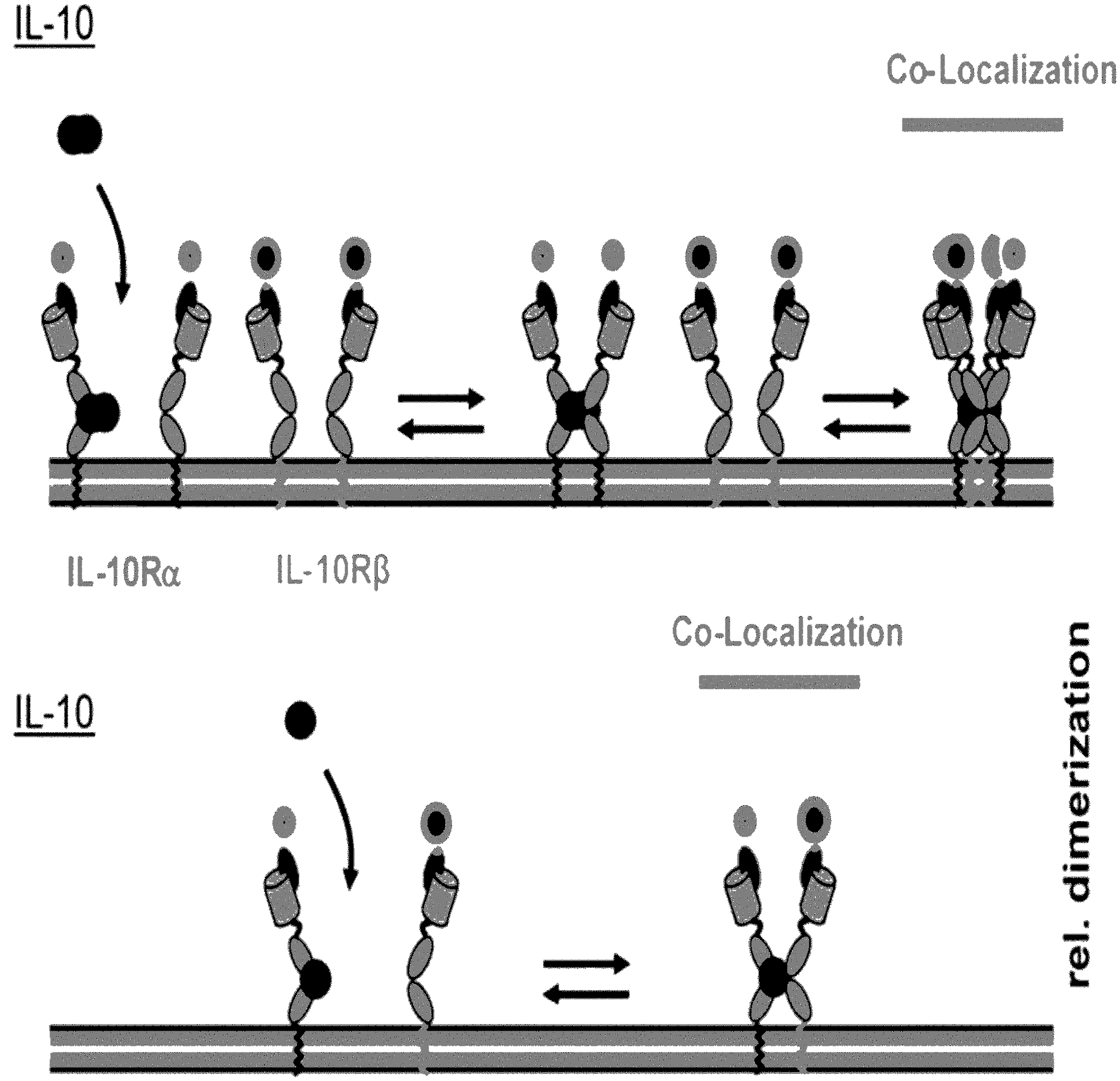
Figure 10A:
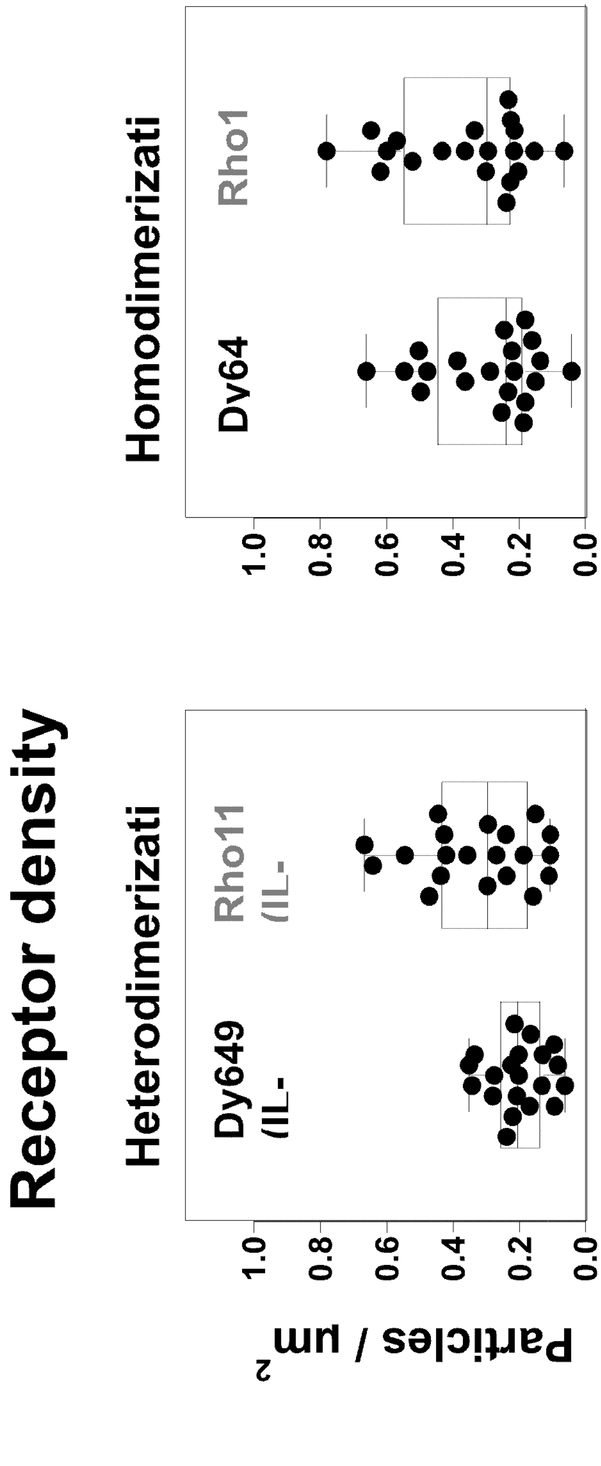

In order to test how increasing the binding affinity to IL-10Rβ altered the dynamics of receptor assembly at the plasma membrane of live cells, we probed diffusion and interaction of both receptor chains by dual colour total internal reflection fluorescence (TIRF) microscopy. To this end, we expressed in HeLa cells IL-10Rα and IL-10Rβ tagged with engineered variants of non-fluorescent (Y67F) mEGFP. The tags were designed to specifically recognise either one of two different anti-GFP nanobodies ((Kirchhofer et al., 2010) pdb: 3K1K and 3G9A). These nanobodies (NBs) were conjugated to photostable organic fluorophores RHO11 and Dy649 suitable for simultaneous dual-colour single molecule tracking of IL-10Rα$^{DY649}$ and IL-10Rβ$^{RHO11}$ on the surface of live cells as shown previously in other cytokine receptor systems (Martinez-Fabregas et al., 2019, Wilmes et al., 2020, Moraga et al., 2015a) (FIG. 2A and FIG. 10A).

Figure 2B:
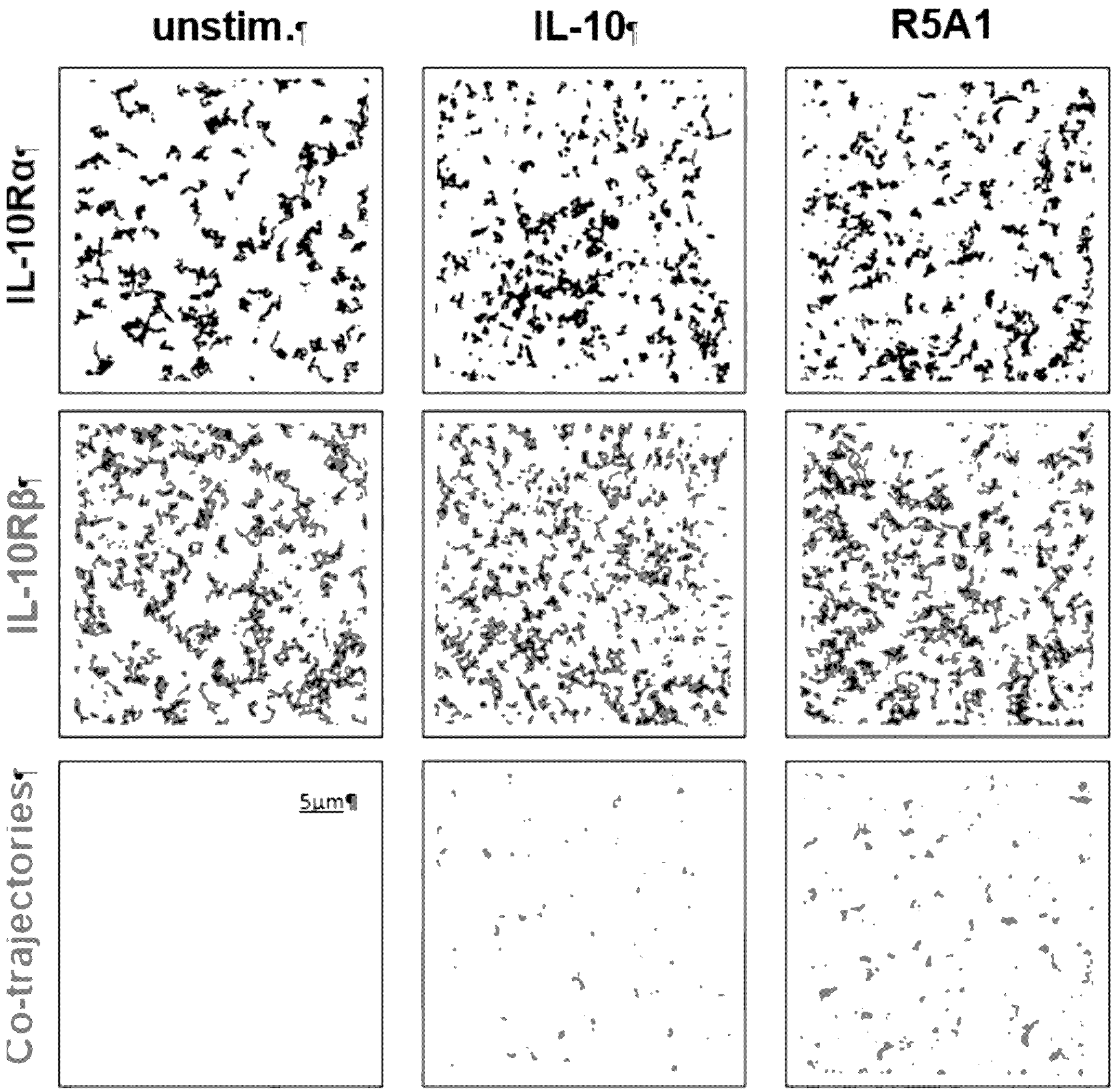
Figure 2C:
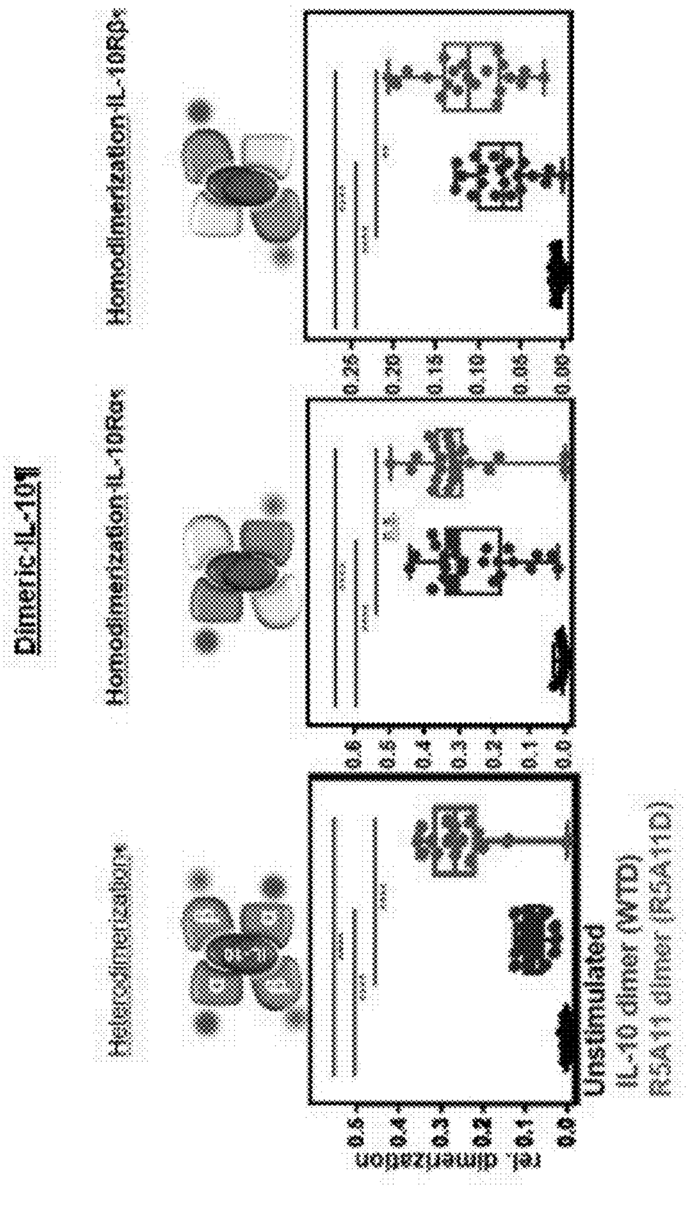
Figure 2D:
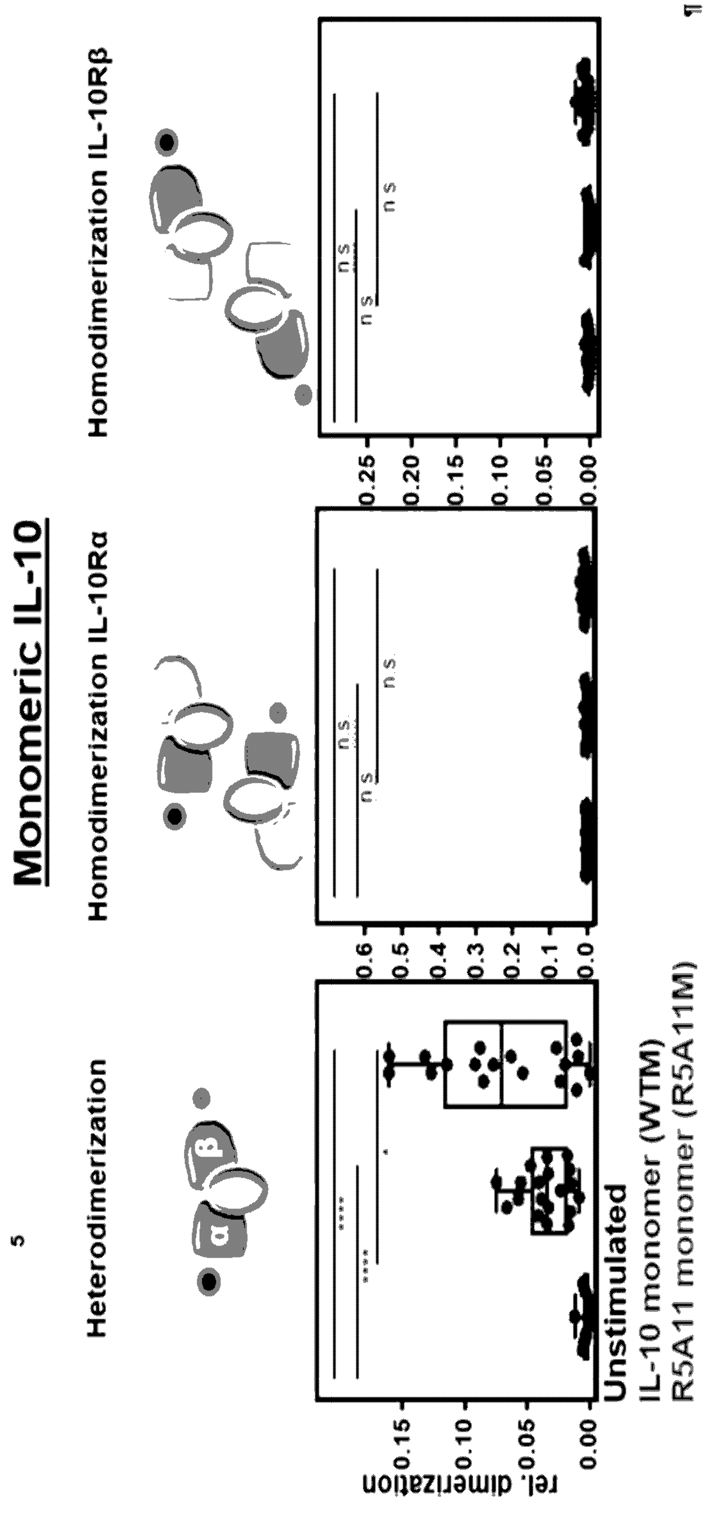
Figure 3D:
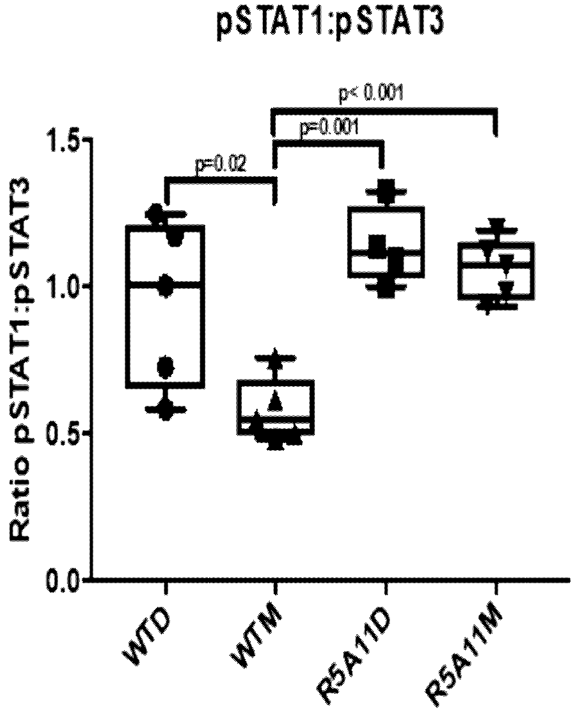
Figure 10B:
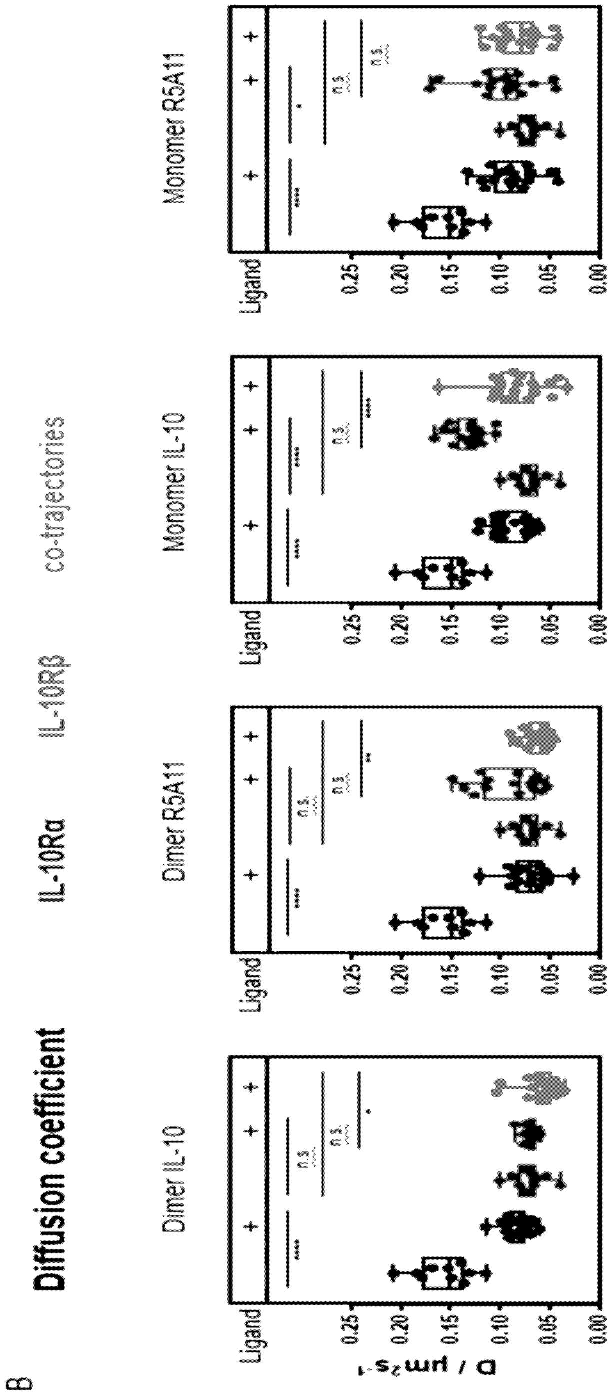

After cell surface labelling we found both receptor subunits freely diffusing in the plasma membrane. Receptors were considered as dimerized if two individual particles were persistently found in both spectral channels for ≥10 consecutive steps (~320 ms) in a proximity of 100 nm. These co-localization/co-tracking thresholds allowed the elimination of density-dependent random encounter co-localizations. In the absence of IL-10, we did not observe heterodimerization of IL-10Rα and IL-10Rβ above background (FIGS. 2B and 2C). Stimulation with saturating concentrations of WTD substantially dimerized IL-10Rα and IL-10Rβ. Strikingly, R5A11D induced a significantly higher level of receptor complex assembly (FIG. 2C). This finding was also confirmed for the monomeric versions of both wild type and high affinity IL-10 variants although at lower levels than seen for the dimeric versions (FIG. 3D). Ligand stimulation led to a significant decrease of diffusion mobility, particularly for IL-10Rα, which is in line with previous reports (FIG. 10B). (Moraga et al., 2015c, Wilmes et al., 2015). We also probed homodimerization of IL-10Rα and IL-10Rβ. To this end, we stochastically labelled either of the receptor chains with both dyes (FIG. 10A), taking into account that only half of the dimers would be labelled with different dyes and thus would be picked up by co-tracking analysis. Stimulation with the dimeric IL-10 induced strong homodimerization of IL-10Rα with no difference between both cytokine variants, as the IL-10Rα binding interface was unaltered in R5A11 (FIG. 2C). Instead, homodimerization of IL-10Rβ was significantly increased for the engineered variant R5A11D. For the monomeric IL-10 variants, all homodimerization experiments failed to induce receptor homodimers, in agreement with the monomeric nature of the ligands (FIG. 2D) (Josephson et al., 2000). Taken together, increased receptor assembly was observed for R5A11 under all conditions in which the affinity-matured interface to IL-10Rβ was involved.

Figure 3E:
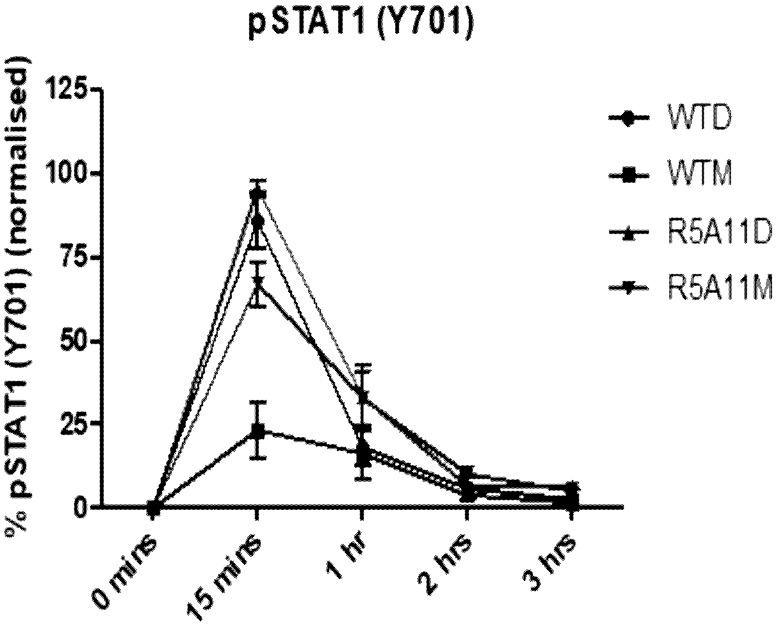

IL-10 Variants Exhibit Enhanced Signalling Activities in Human Primary Monocytes IL-10 inhibits inflammatory processes by modulating the activities of different innate cells including monocytes. We next performed a battery of signalling and activity assays in human monocytes to investigate the anti-inflammatory potential of our engineered variants. Monocytes (CD14+ cells) were isolated from human buffy coats and rested for two days before stimulation with IL-10 wt and high affinity monomer and dimers (FIG. 3A). Levels of STAT1 and STAT3 phosphorylation upon ligand stimulation were measured by flow cytometry as these two transcription factors represent the major signalling pathway engaged by IL-10 (Wehinger et al., 1996, Finbloom and Winestock, 1995). At saturating concentrations R5A11D and WTD activated comparable STAT1 and STAT3 levels (FIG. 3B). However, R5A11D showed enhanced phosphorylation of both STAT3 and STAT1 at sub-saturating concentration, which translated into a decrease in $EC_{50}$ values compared to WTD (FIGS. 3B and 3C). WTM showed a poor activation of STAT3 and STAT1 with amplitudes of activation less than fifty percentage of those elicited by the WTD (FIG. 3B). Interestingly, WTM triggered a biased signalling response. While WTD, R5A11D and R5A11M showed a 1:1 pSTAT1 to pSTAT3 ratio, WTM showed a clear bias towards pSTAT3 (FIG. 3D), agreeing with previous observations from our laboratory describing biased signalling by short-lived cytokine-receptor complexes (Martinez-Fabregas et al., 2019). R5A11M induced activation of both STAT3 and STAT1 to levels comparable to those induced by the dimeric cytokines at saturating doses, suggesting that the defective signalling elicited by WTM results from its weak receptor binding affinity (FIGS. 3B and 3C). Signalling kinetics studies showed that the signalling profiles obtained in our dose response studies were not confounded by differences in signalling kinetics elicited by the different IL-10 variants. The four IL-10 ligands triggered comparable signalling kinetics in human monocytes (FIG. 3E and FIG. 11), confirming that their different signalling profiles result from their different binding affinities to IL-10Rβ.

Figure 3F:
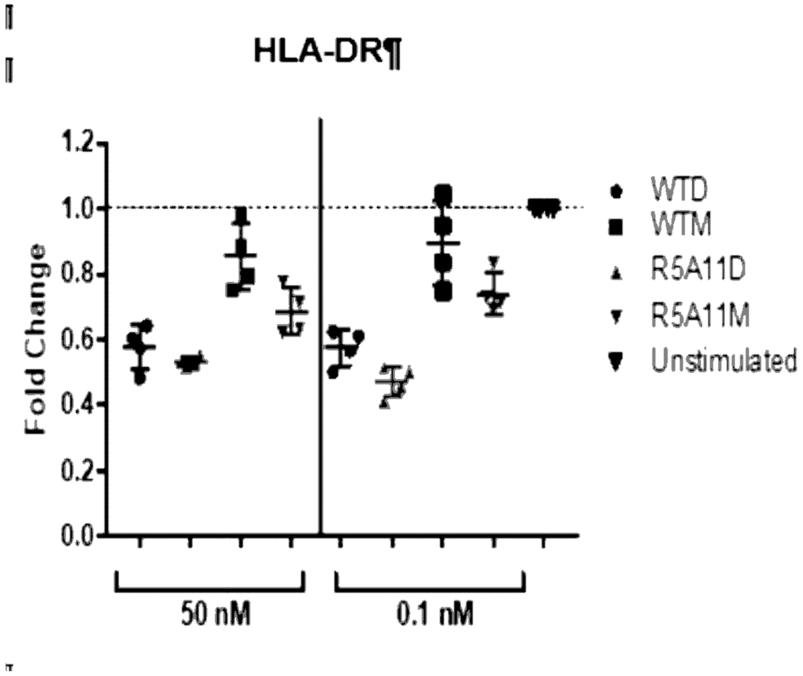
Figure 3G:
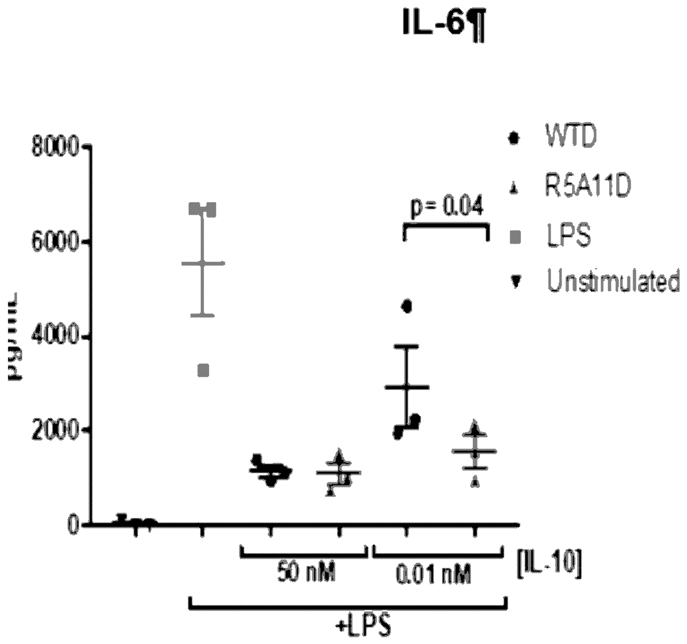

IL-10 exerts its anti-inflammatory properties by inhibiting antigen presentation in innate cells such as monocytes and dendritic cells (Mittal and Roche, 2015). Thus, we next studied whether IL-10 binding affinity to IL-10Rβ influences its ability to decrease HLA-DR expression in human primary monocytes. WTD and R5A11D reduced the HLA-DR surface levels to similar extent (50%) at saturating doses, in agreement with their comparable signalling profiles (FIG. 3F). At sub-saturating doses however, R5A11D showed an advantage over WTD, inducing a stronger downregulation of HLA-DR expression (FIG. 3F). WTM induced a mild reduction of HLA-DR surface levels (20%) paralleling its poor signalling potency (FIG. 3F). Interestingly, R5A11M induced only a 30% reduction of the surface HLA-DR levels, despite activating STAT1/STAT3 to a very similar extent to the dimeric ligands (FIG. 3F), suggesting an additional mechanism by which IL-10 regulates H LA-DR expression. We next investigated how IL-10Rβ binding affinity correlates with IL-10's ability to inhibit pro-inflammatory cytokine production by monocytes. For this, we measured levels of IL-6 secreted by monocytes upon LPS stimulation in the presence of the indicated doses of WTD and R5A11D (FIG. 3G). At saturating concentrations WTD and R5A11D effectively inhibited IL-6 secretion to a similar extent (FIG. 3G). However, at sub-saturating doses R5A11D again showed a marked improvement over WTD (FIG. 3G). Together our data highlights that IL-10 variants exhibiting enhanced binding towards IL-10Rβ gain a functional advantage at sub-saturating doses, such as those found during therapeutic interventions.

Figure 4A:
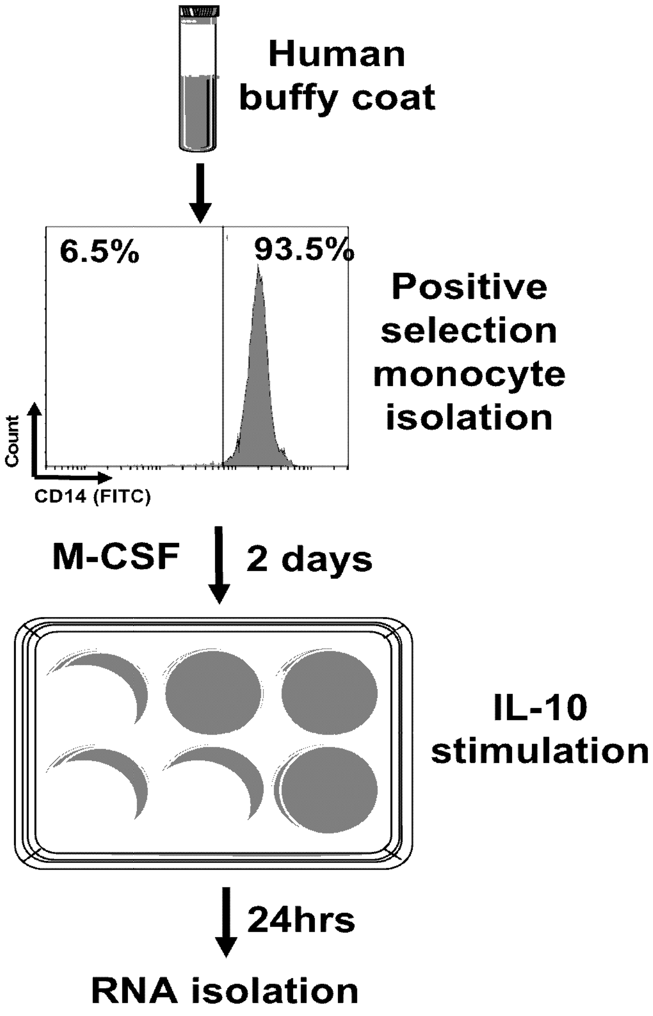
Figure 4B:
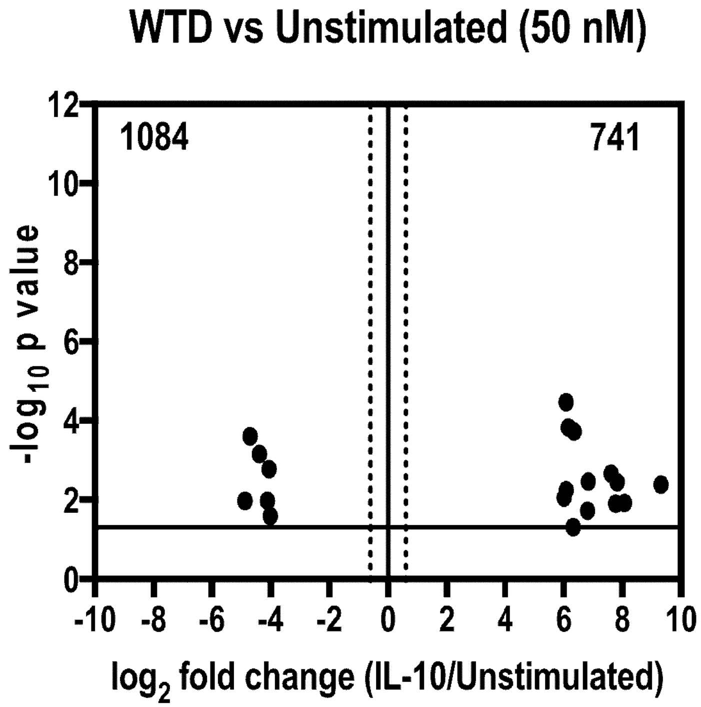
Figure 4C:
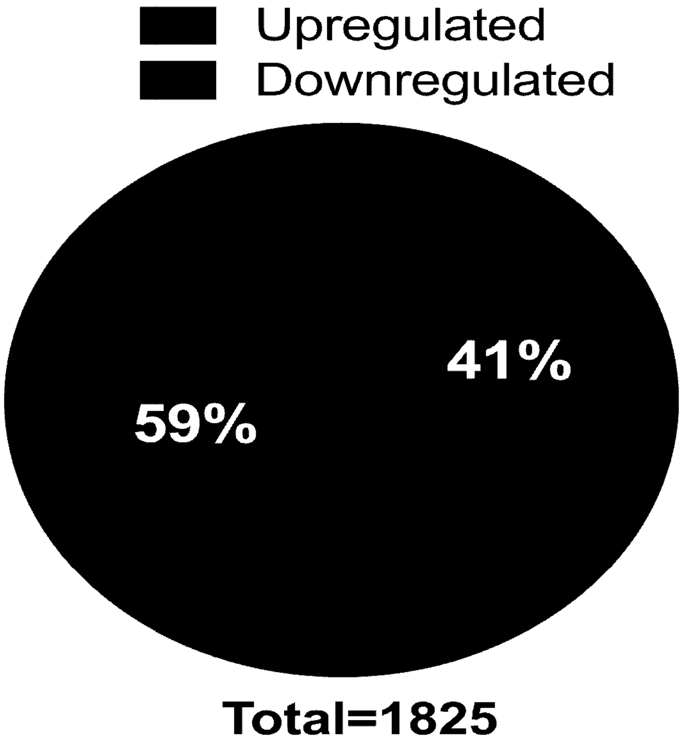
Figure 4D:
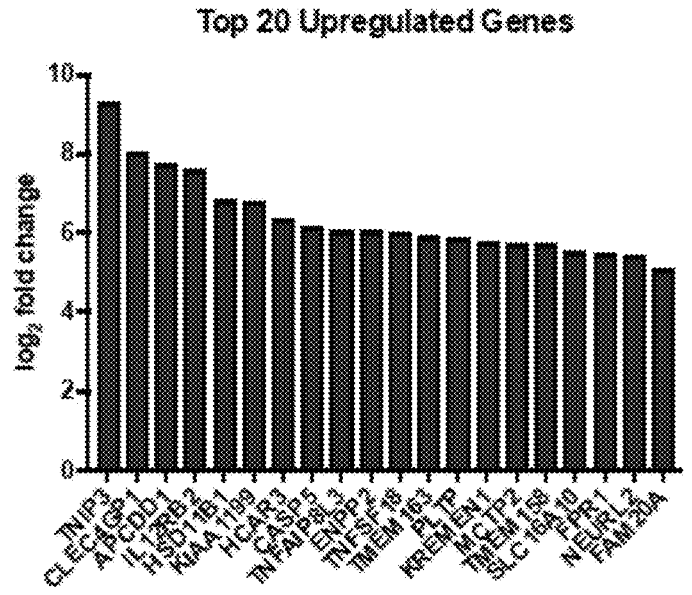
Figure 4E:
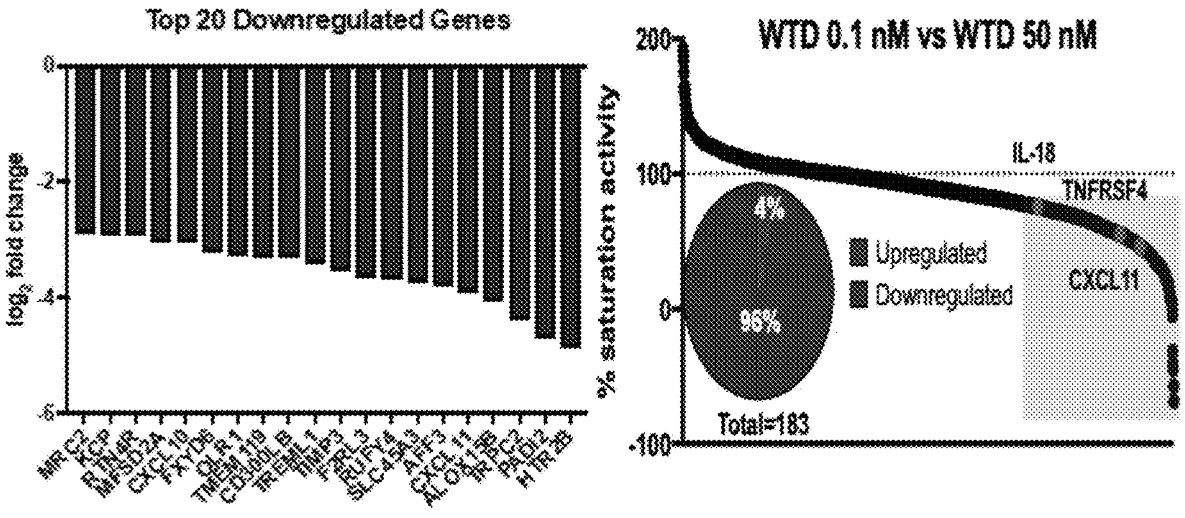
Figure 4G:
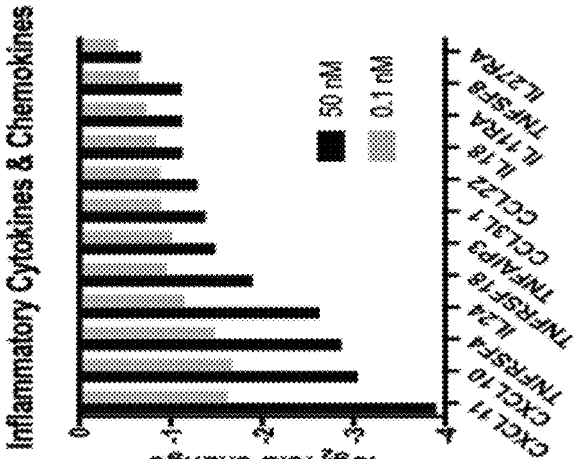
Figure 4F:
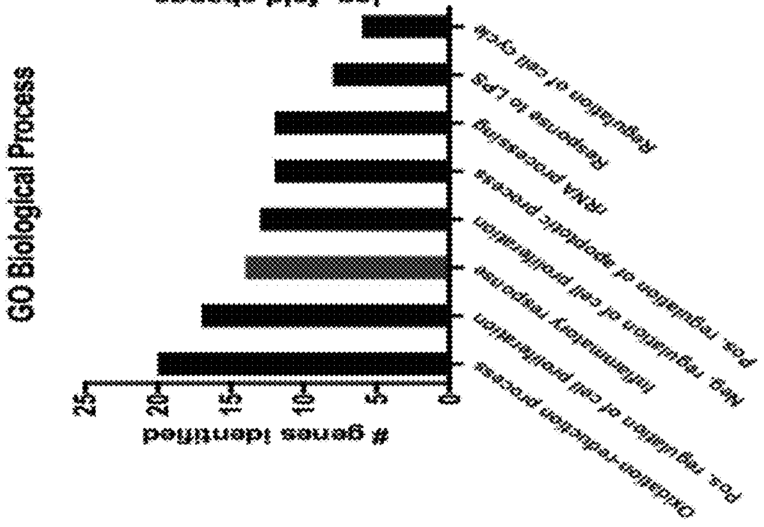
Figure 5A:
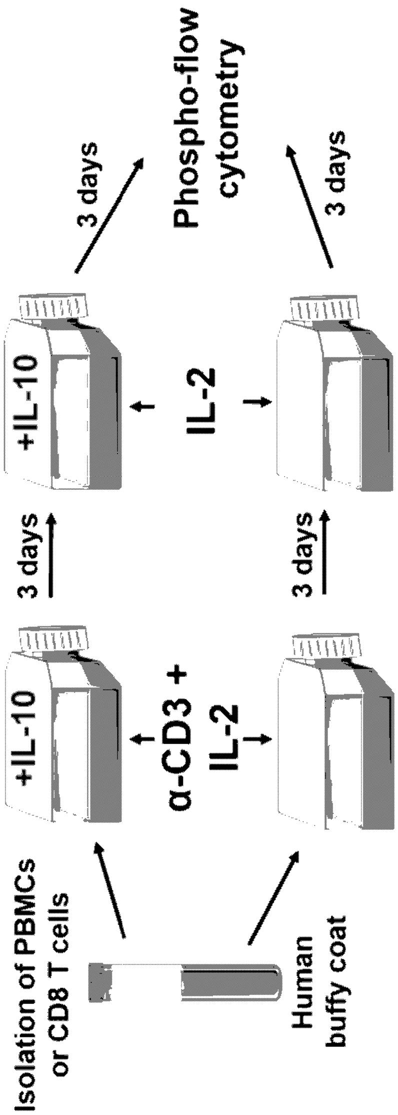
Figure 5B:
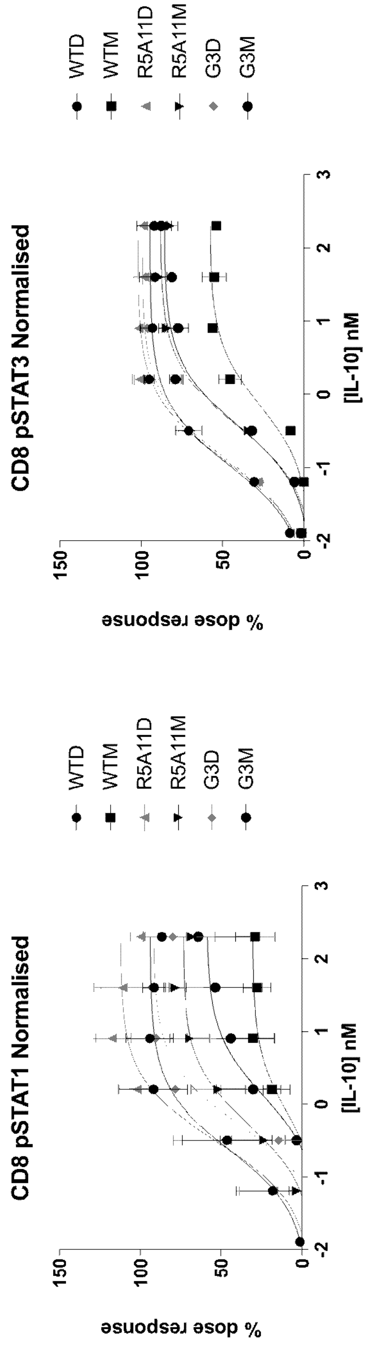
Figure 5C:
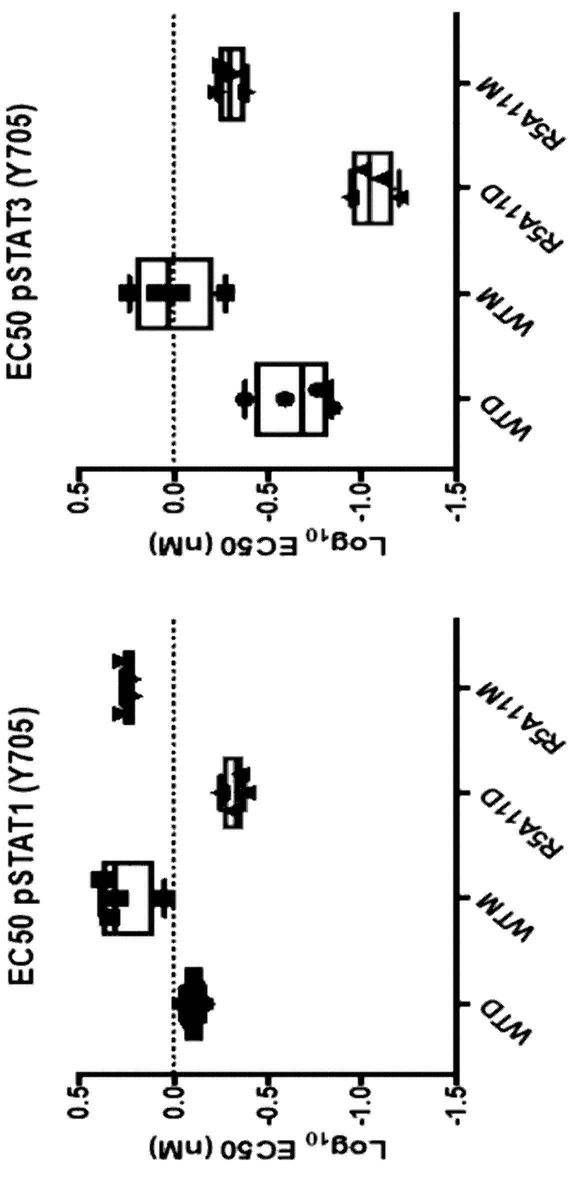
Figure 5D:
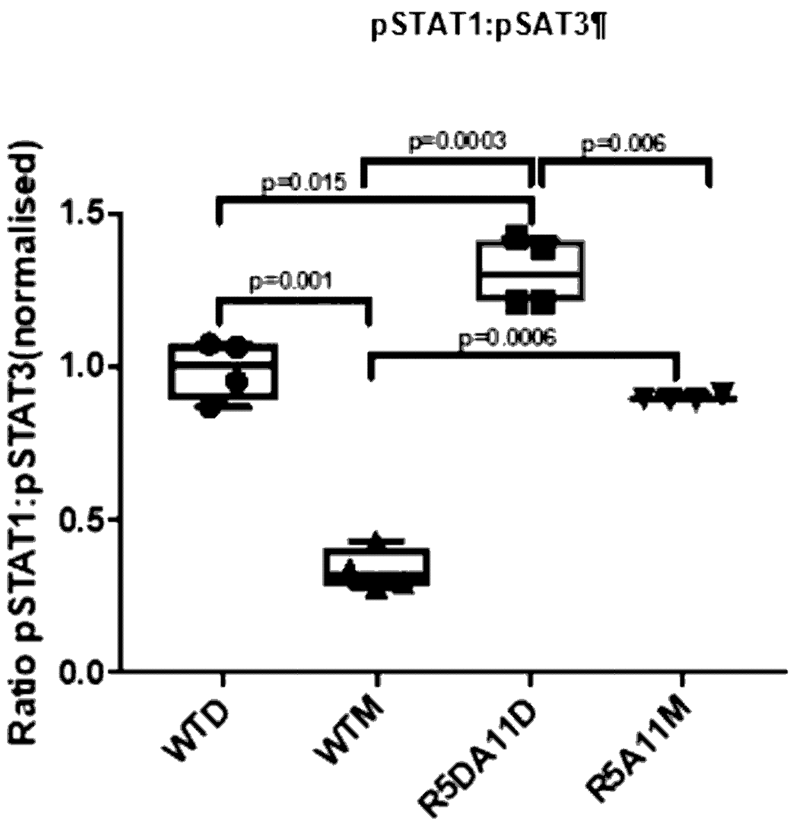
Figure 12A:
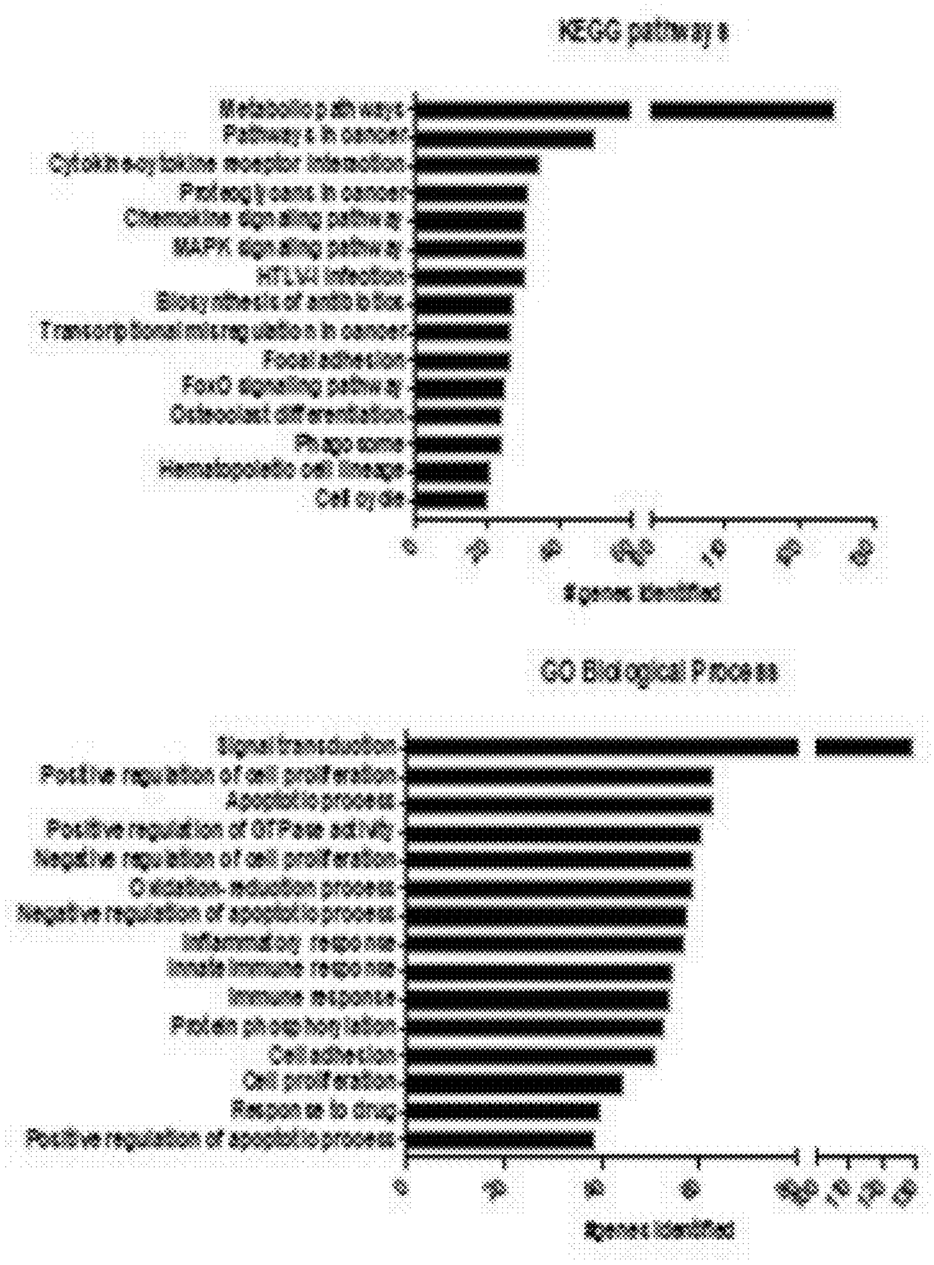
Figure 12A:
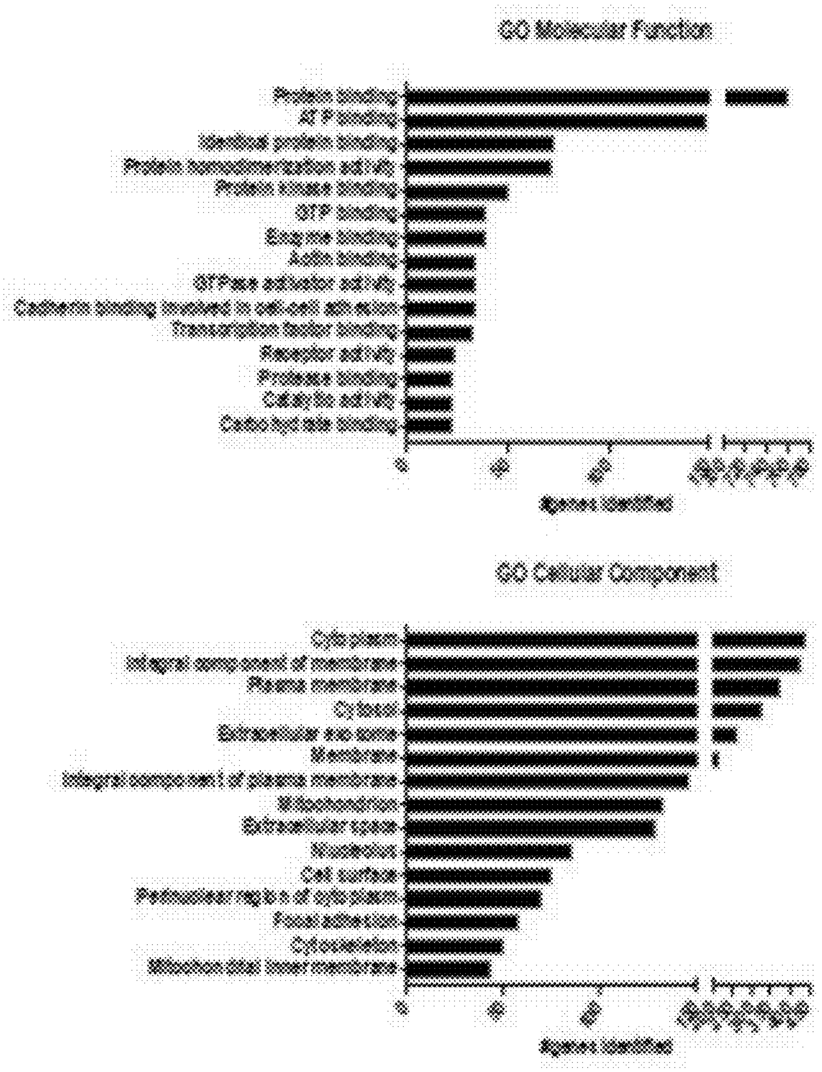
Figure 12B:
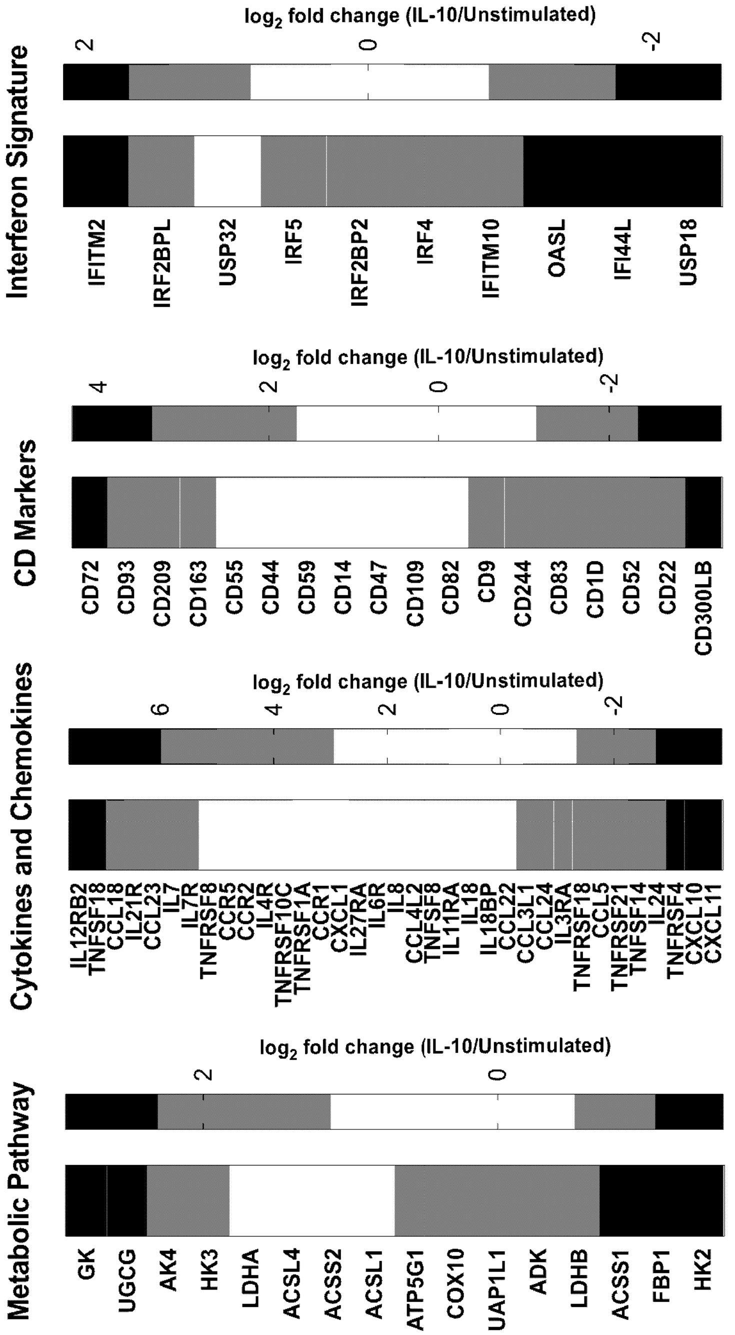

Increased Receptor Affinity Enhances Transcriptional Activity of IL-10 in Monocytes Our initial studies in monocytes were focused on two classical markers regulated by IL-10, i.e. HLA-DR levels and IL-6 expression. To gain a broader understanding of how our variants regulate human monocytes activities, we performed detailed transcriptional analysis of human monocytes stimulated with the different IL-10 ligands for 24 hrs. Monocytes were isolated and treated as in FIG. 4A. WTD treatment elicited a strong transcriptional regulation in human monocytes inducing the upregulation of 741 genes and downregulation of 1084 genes (FIGS. 4B and 4C). Highly upregulated and downregulated genes are shown in FIG. 5D. KEGG pathway analysis showed a large number of genes regulated by IL-10 treatment involved in metabolic pathways (FIG. 12A), a selection of which are shown in FIG. 12B. WTD treatment regulated expression of hexokinase-2 and hexokinase-3, key enzymes in glycolysis. Genes associated with acyl-CoA synthesis, ACSS2, ACSL4, ACSL1, were also significantly upregulated highlighting a potential regulation of lipid biosynthesis by IL-10 (FIG. 12B). In addition to metabolic-related genes, WTD treatment regulated expression of cytokines, chemokines and their receptors (FIG. 12B). For instance, cytokines receptors such as IL-12Rβ2, IL-21Rα and IL-4Rα were upregulated while cytokines such as IL-8, IL-18 and IL-24 were downregulated (FIG. 12B). Expression of CXCL1, CCL22, CCL24, CCL18, CXCL10 and CXCL11 chemokines was also modulated by IL-10 treatment contributing to an anti-inflammatory environment. We also observed the regulation of a miscellaneous collection of CD markers by WTD treatment, including CD93—a receptor critical for monocyte phagocytosis and CD44 and CD9—markers involved in cell surface adhesion (FIG. 12B); and an inhibition of type I IFN gene signature, in agreement with previous studies (Ito et al., 1999, Dallagi et al., 2015) (FIG. 12B). Overall, our transcriptional studies revealed a broad regulation of monocyte biology by IL-10, englobing the fine-tuning of their energy homeostasis, migration and trafficking. Remarkably, 90% of genes regulated by WTD at saturating doses were induced to the same extent when sub-saturating doses of WTD were used, highlighting the robustness of the IL-10 responses (FIG. 4E). However, interestingly of the 10% of genes differentially regulated by WTD at the two doses, 96% of those correspond to genes downregulated by IL-10 treatment and include critical pro-inflammatory chemokines and cytokines (FIGS. 4E and 4F). A list of differentially expressed genes is provided in FIG. 5G. Our data shows that low doses of IL-10 treatment specifically disrupt the ability of IL-10 to block expression of key cytokines and chemokines that critically contribute to enhance the inflammatory response.

Figure 4H:
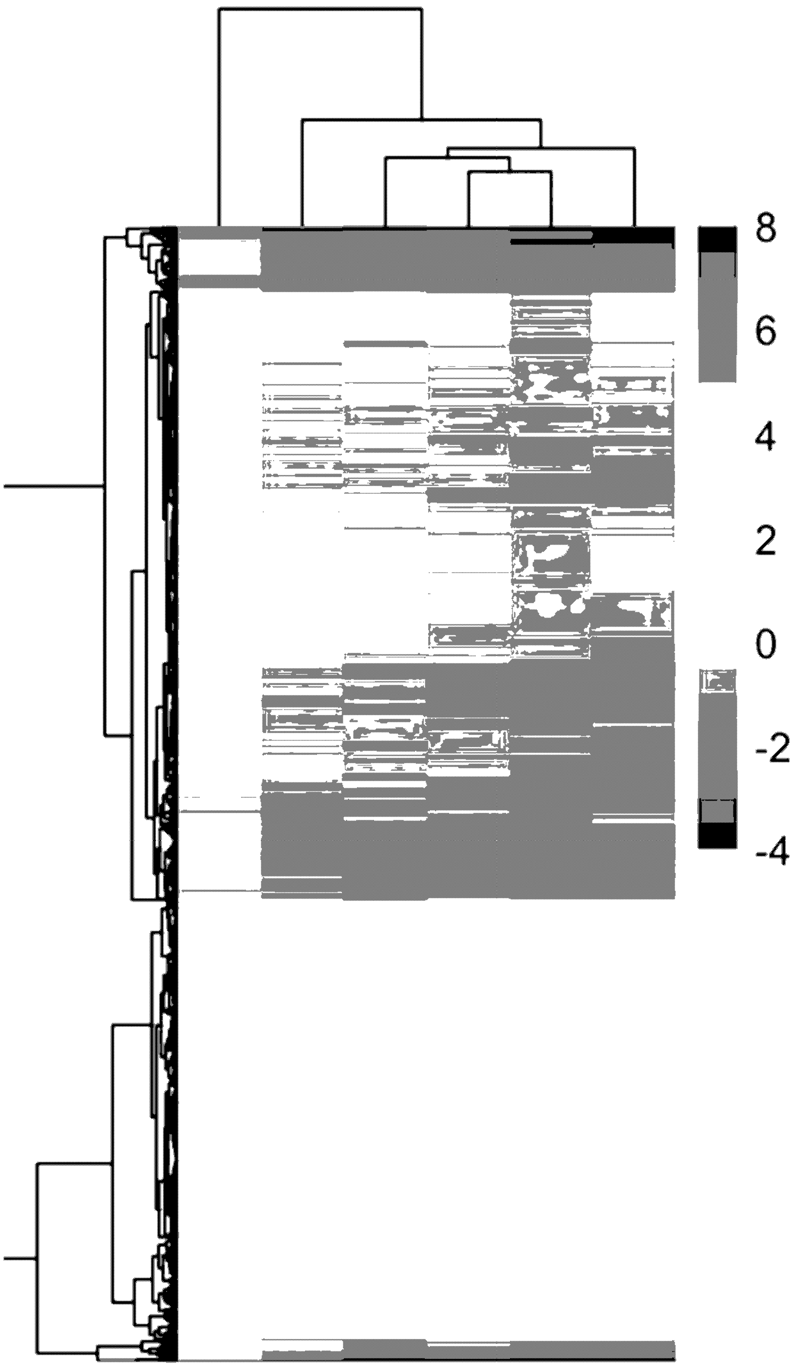
Figure 4I:
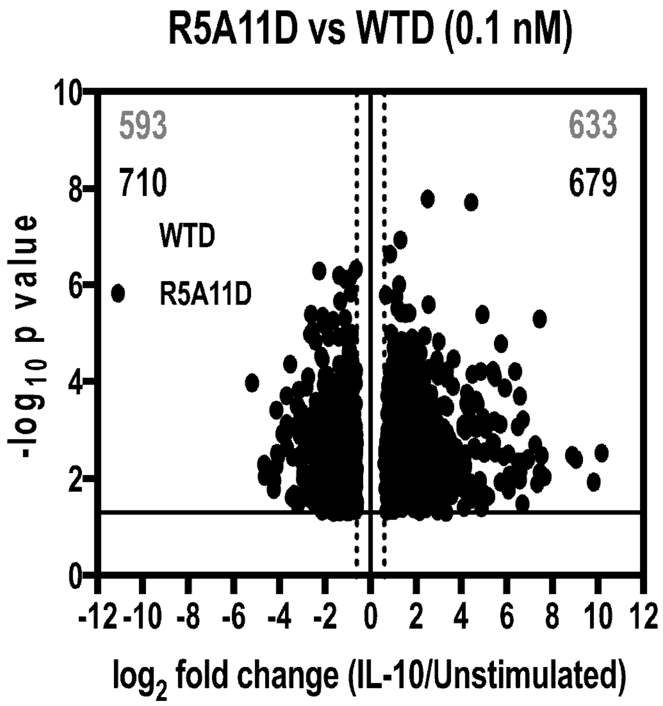
Figure 4J:
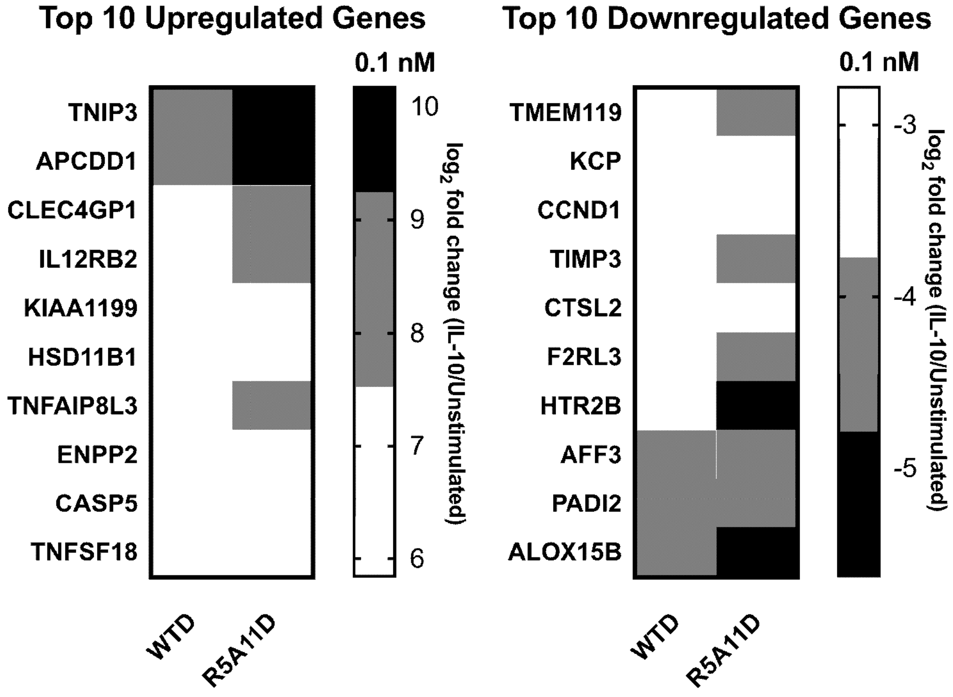
Figure 4K:
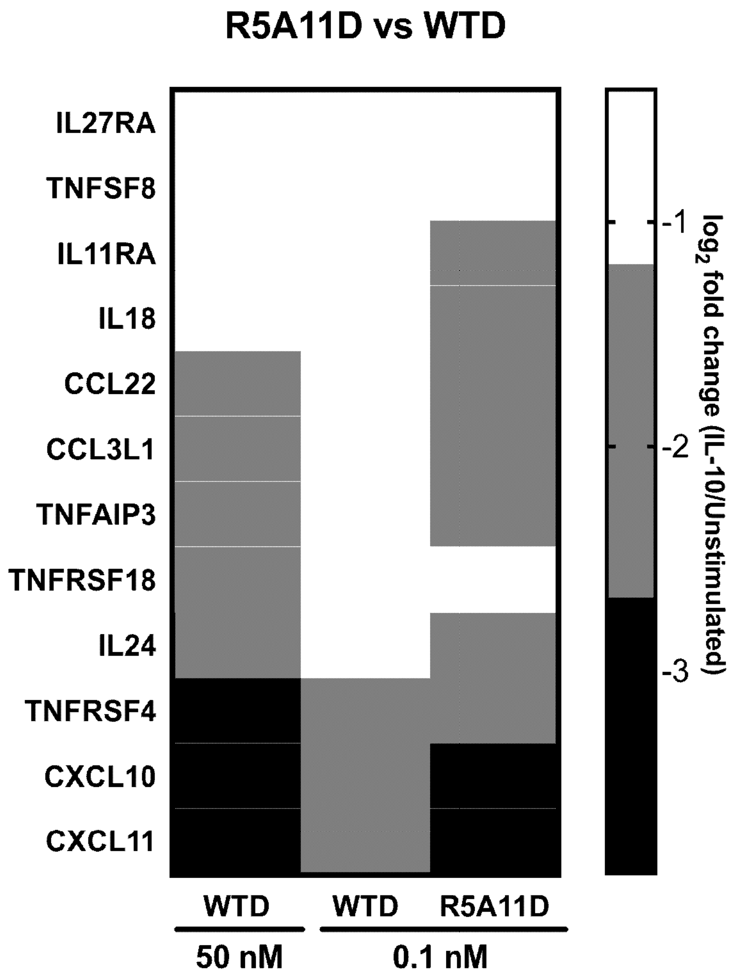
Figure 12C:
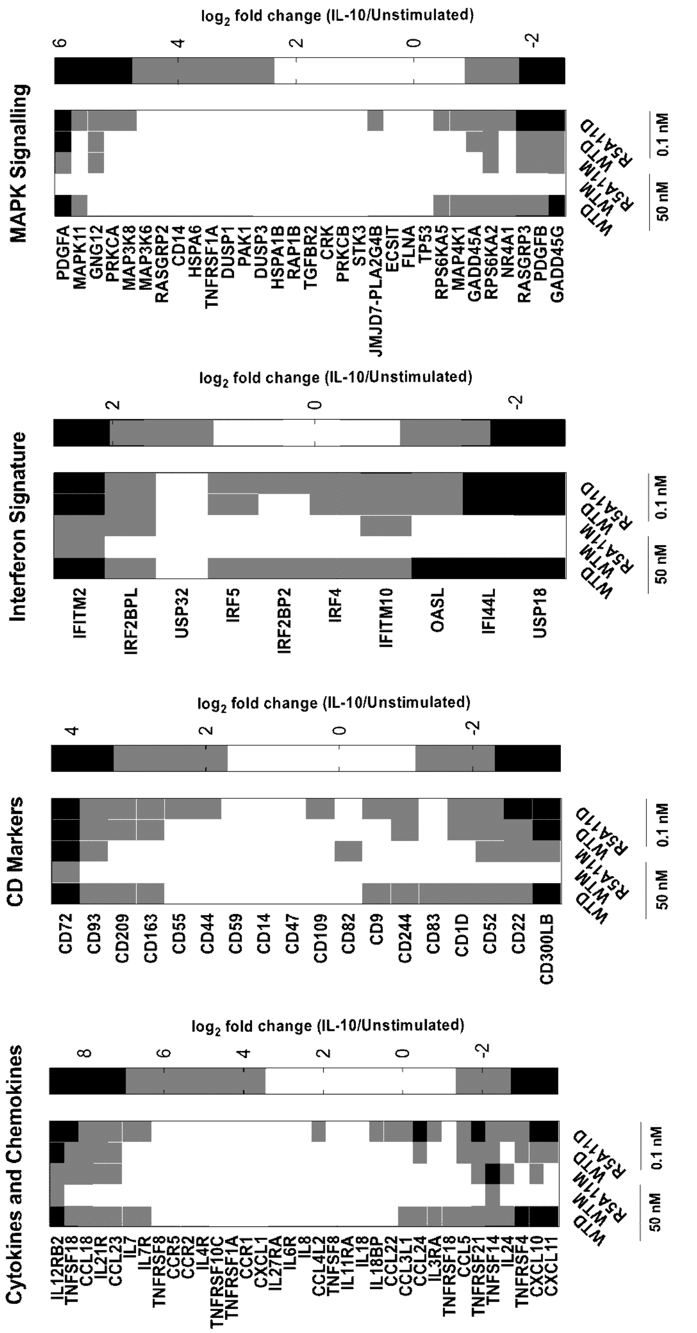
Figure 12D:
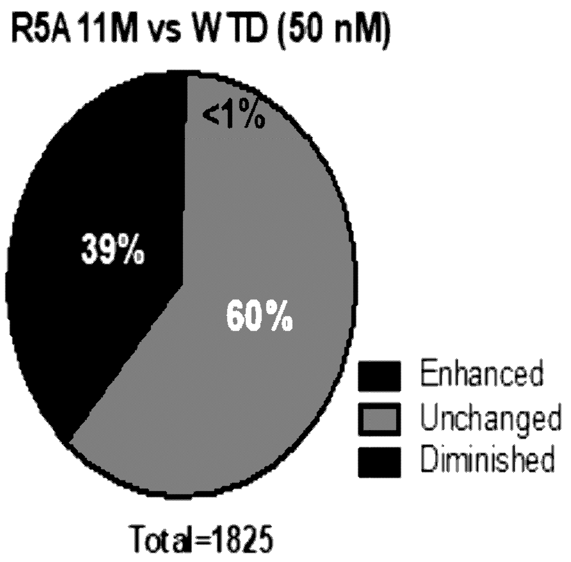
Figure 12E:
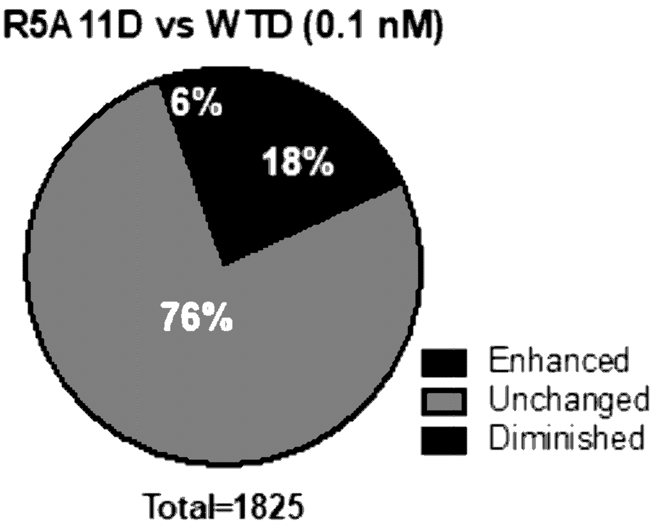

Next we studied how the engineered IL-10 variants regulated gene expression programs in monocytes. WTM induced a very poor transcriptional response, in line with its weak signal activation profile (FIG. 4H and FIG. 12C). Interestingly R5A11M triggered a more potent transcriptional response when compared to WTM but failed to reach the same potency induced by the dimeric ligands (FIG. 4H and FIG. 12C). A direct comparison between WTD and R5A11M showed that the latter monomeric ligand exhibited a diminished effect in 39% of genes regulated by IL-10 (FIG. 12D). This is in contrast to its ability to activate STAT1 and STAT3 to levels comparable to those induced by the dimeric ligands, suggesting that STAT activation does not directly correlate with transcriptional activity in the IL-10 system. In agreement with our signalling studies, R5A11D induced a more robust gene expression profile at sub-saturating doses when compared to WTD (FIG. 4H). R5A11D enhanced the expression of 18% of genes regulated by WTD at 0.1 nM, with only 6% of genes showing favourable activity by WTD over R5A11D (FIGS. 4H and 4I, FIG. 12E). FIG. 4J shows that of the top 10 IL-10 regulated genes, the majority of them displayed enhanced activity by R5A11D. This pattern holds true when genes are group by families, i.e. cytokines & chemokines, CD markers and MAPK signalling (FIG. 12C). Importantly, key pro-inflammatory cytokines, which were not regulated by WTD at low doses, are still regulated by R5A11D (FIG. 4K). Overall, our transcriptional data shows that IL-10 regulates monocyte biology at different levels and that R5A11D, by exhibiting enhanced affinity towards IL-10Rβ, elicits more robust responses at a broader range of ligand concentrations, holding the potential to rescue IL-10 based therapies targeting inflammatory disorders.

Figure 5E:
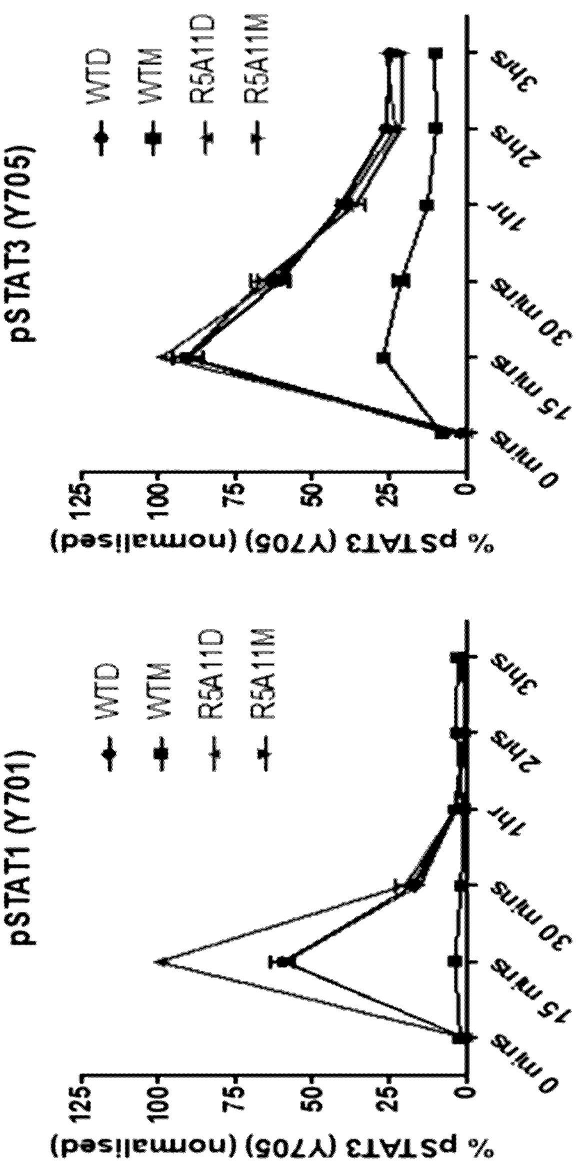

IL-10 Variants Exhibit Enhanced Signalling Activities in Human Primary CD8 T Cells In addition to its potent anti-inflammatory effects IL-10 stimulates cytotoxic CD8 T cells under certain circumstances, enhancing production of effector molecules and increasing their cytotoxic activity (Oft, 2014). We next investigated whether the enhanced activities exhibited by our affinity-matured variants in monocytes would translate into CD8 T cells. Human primary CD8 T cells were grown and activated as shown in FIG. 5A and STAT1/STAT3 activation levels in response to the indicated concentrations of IL-10 variants were measured by flow cytometry (FIG. 5B). WTD and R5A11D induced very similar STAT phosphorylation levels at saturating doses, but R5A11D showed a decreased $EC_{50}$ value and stronger signalling at sub-saturating doses (FIG. 5B-D), agreeing with our results in monocytes. Interestingly R5A11D showed a more potent activation of STAT1 over STAT3 which we did not observed in monocytes, suggesting that long-lived IL-10 receptor complexes gain an advantage activating STAT1 in CD8 T cells. WTM exhibited weak activation of STAT1 and STAT3, inducing less than 25% of the activation amplitudes elicited by the dimeric molecules and exhibited a biased STAT3 activation (FIG. 5B-D). In contrast to what we observed in monocytes, R5A11M also elicited a STAT3 biased response activating STAT3 to 80% of the levels induced by the dimeric molecules and STAT1 to 60% of the levels induced by the dimeric molecules (FIG. 5B-D), suggesting that fundamental differences between monocytes and CD8 T cells impact signalling downstream of the IL-10 receptor complex. As with monocytes, signalling kinetic studies revealed that the observed differences in signalling output by the different IL-10 ligands did not result from altered signalling activation kinetics (FIG. 5E).

Figure 5F:
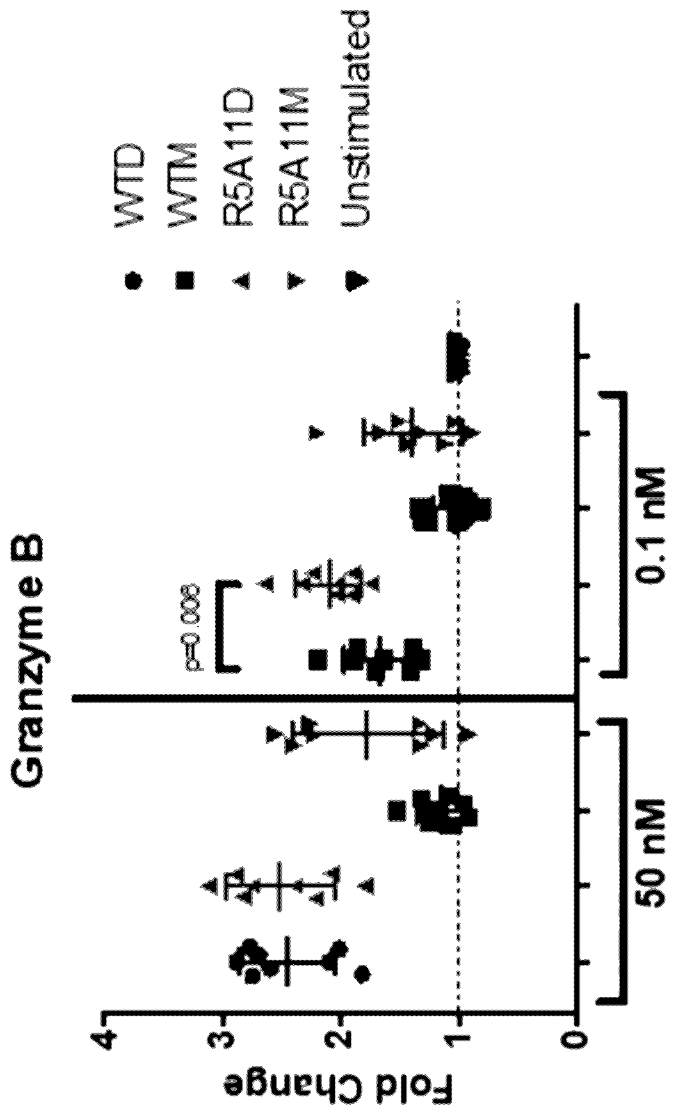
Figure 13A:
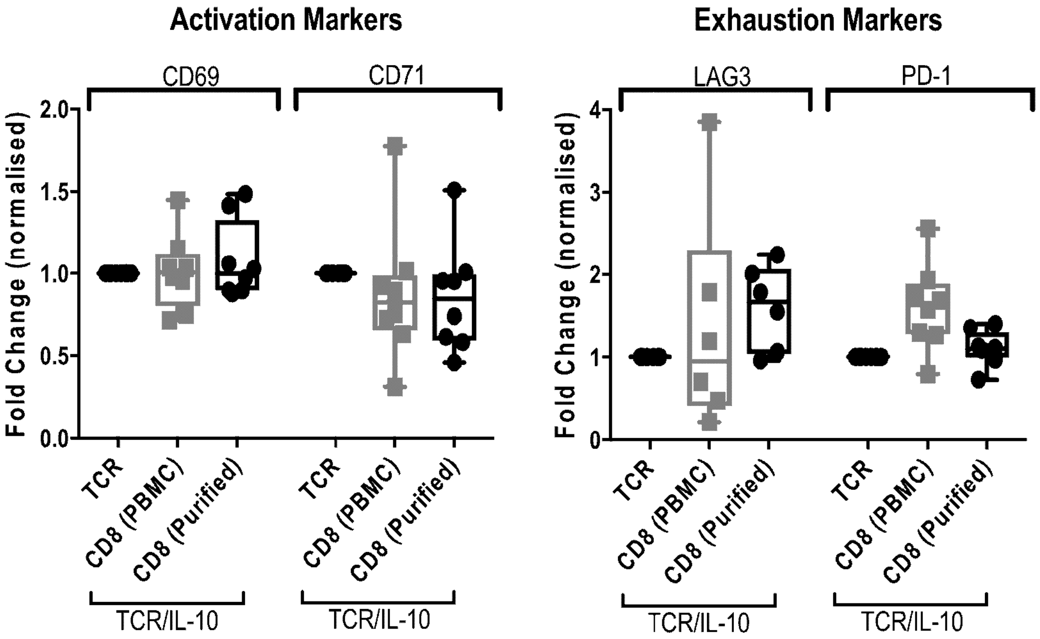
Figure 13B:
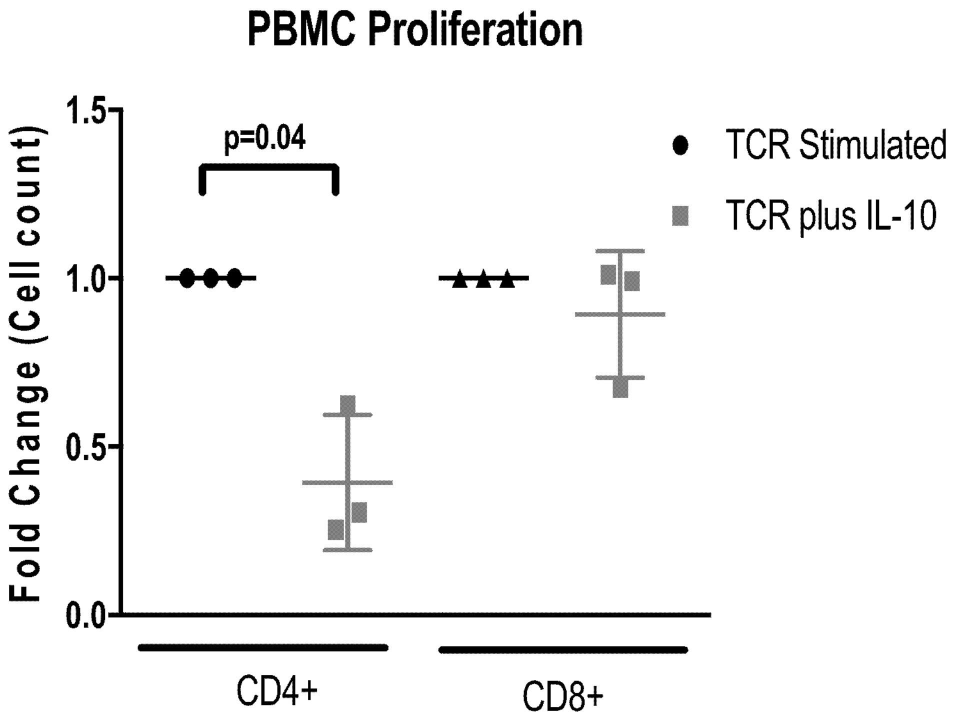
Figure 13C:
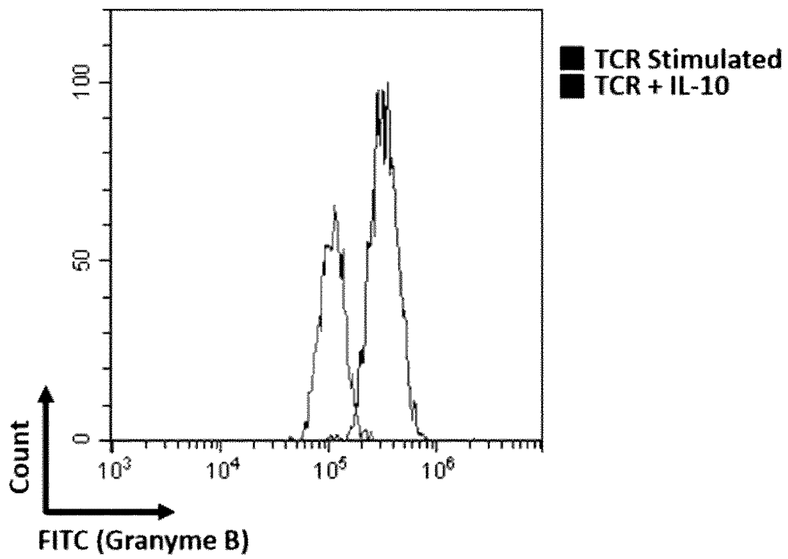
Figure 13C:
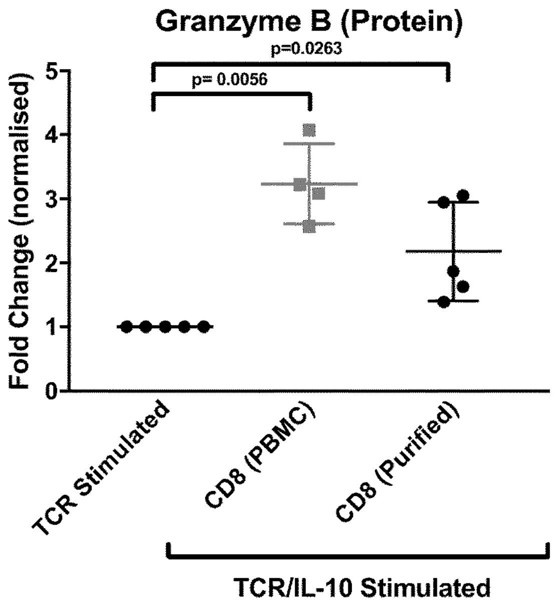
Figure 13C:
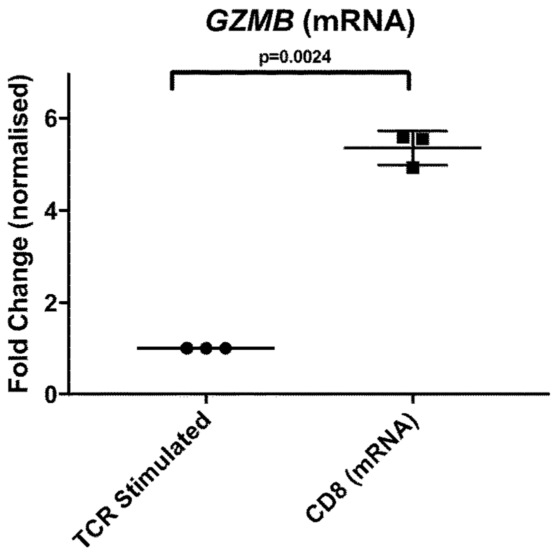

Granzyme B is a potent cytotoxic effector molecule which has been shown to be increased in CD8 T cells upon IL-10 stimulation (Naing et al., 2018). Next, we studied how granzyme B production by CD8 T cells was regulated by the different IL-10 ligands. For that, PBMCs or isolated CD8 T cells were activated following the workflow illustrated in FIG. 6A and granzyme B levels were measured by flow cytometry or qPCR. As previously reported IL-10 stimulation did not affect classical early and late activation markers, i.e. CD69 and CD71 respectively, nor induced a significantly higher upregulation of inhibitory receptors, i.e. LAG-3 and PD-1 or affect CD8 cell proliferation (FIGS. 13A and 13B). On the other hand, IL-10 stimulation led to a strong upregulation of granzyme B levels in monocytes both at the mRNA and protein levels, independently of whether CD8 T cells were activated in the context of a PBMC population or a purified CD8 T cell population (FIG. 13C). When we compared our IL-10 ligands, at saturating concentrations WTD and R5A11D upregulated granzyme B production to a similar extent, 2.5-fold higher than granzyme B levels induced by TCR stimulation alone (FIG. 5F). WTM showed very poor granzyme B production in agreement with its weak STAT activation. At a sub-saturation concentration, we again observed a stronger upregulation of granzyme B levels induced by R5A11D. Interestingly, R5A11M stimulation resulted in two major populations, with half of the donors upregulating granzyme B to levels similar to those induced by WTM and the other half upregulating granzyme B to levels comparable to those induced by the dimeric molecules. Overall, our results show that enhanced affinity for IL-10Rβ bestows IL-10 with robust activities over a wide range of ligand doses and immune cell subsets.

Figure 6A:
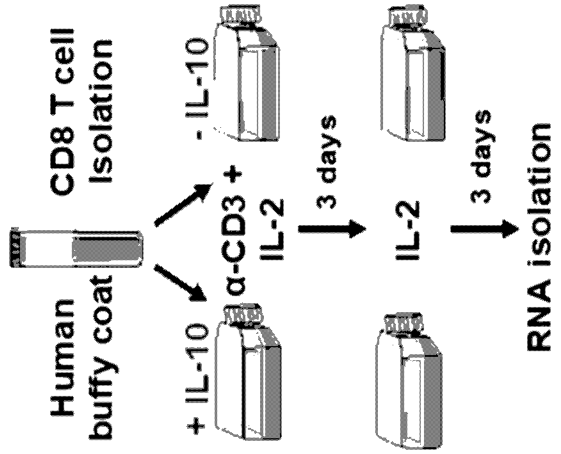
Figure 6B:
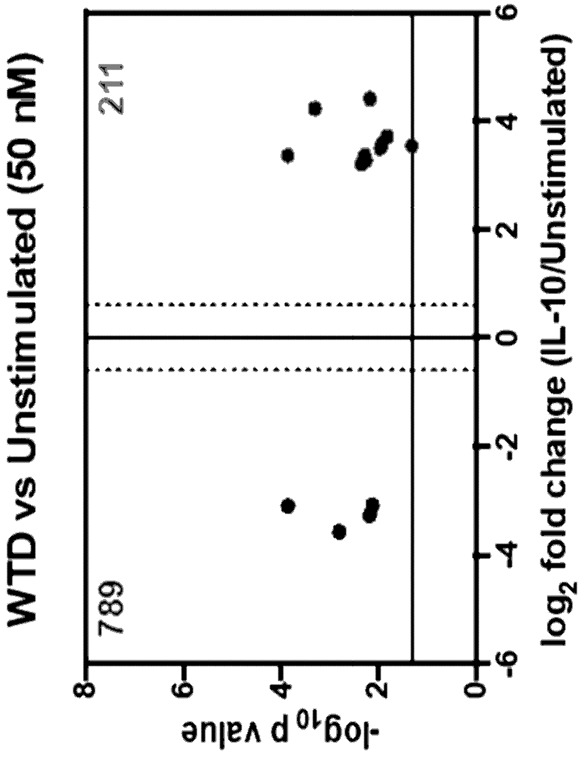
Figure 6C:
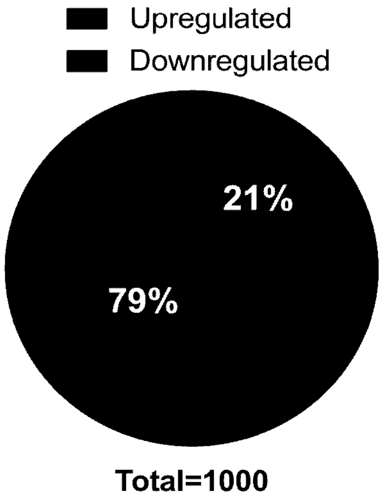
Figure 6D:
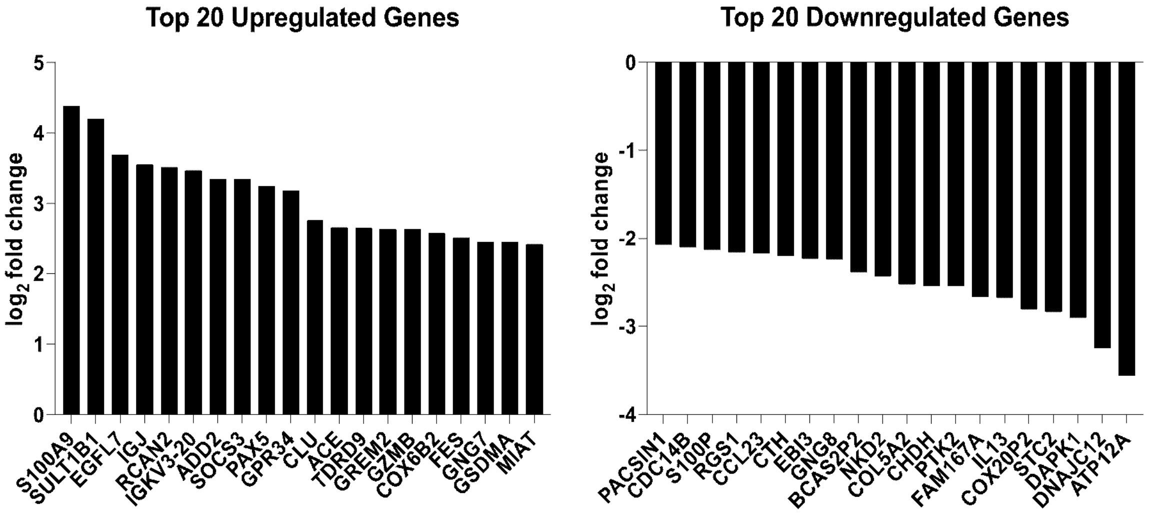
Figure 6E:
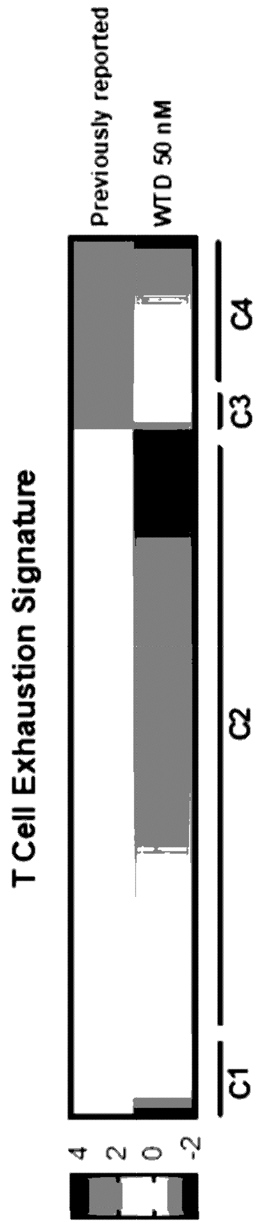
Figure 6F:
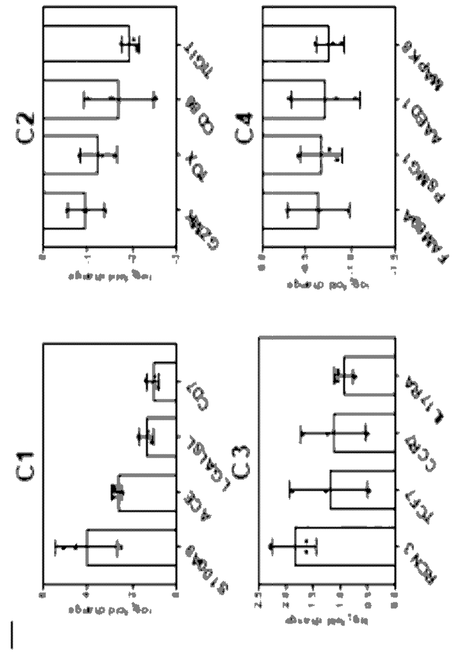
Figure 6G:
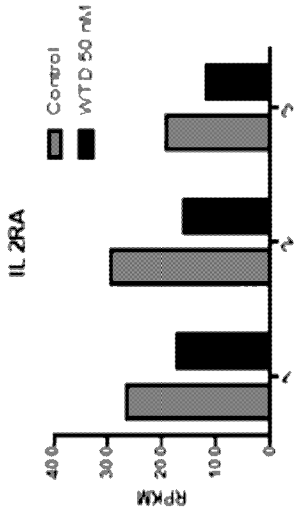
Figure 6I:
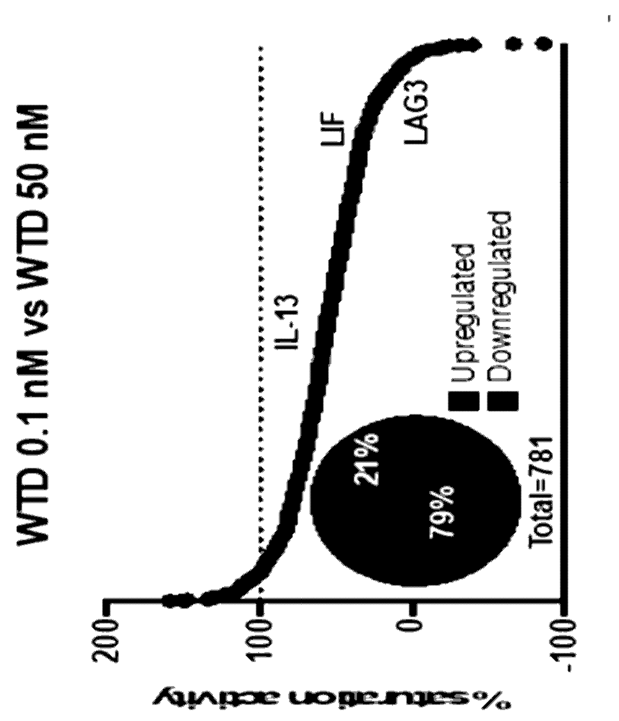
Figure 6H:
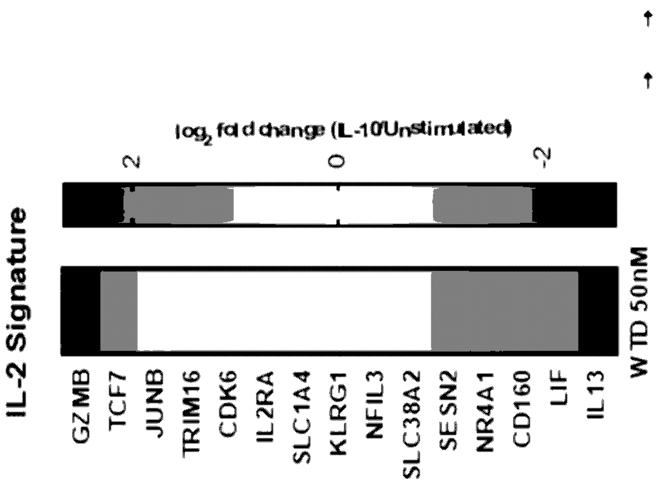
Figure 6J:
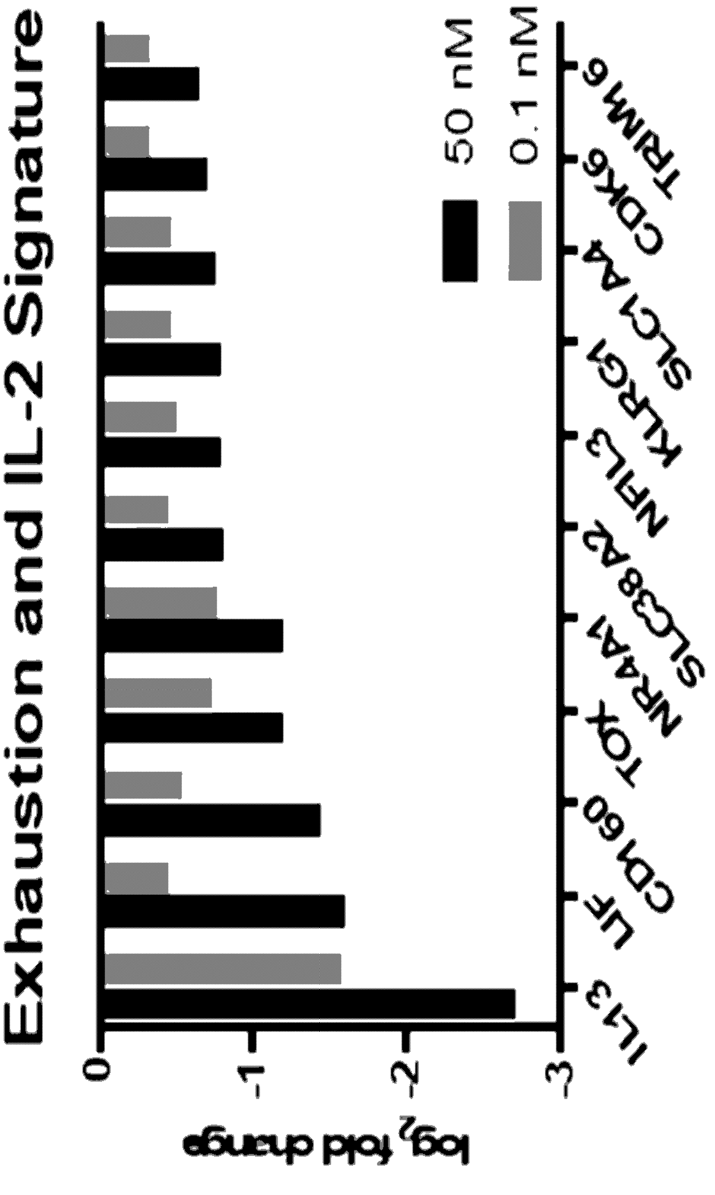
Figure 14A:
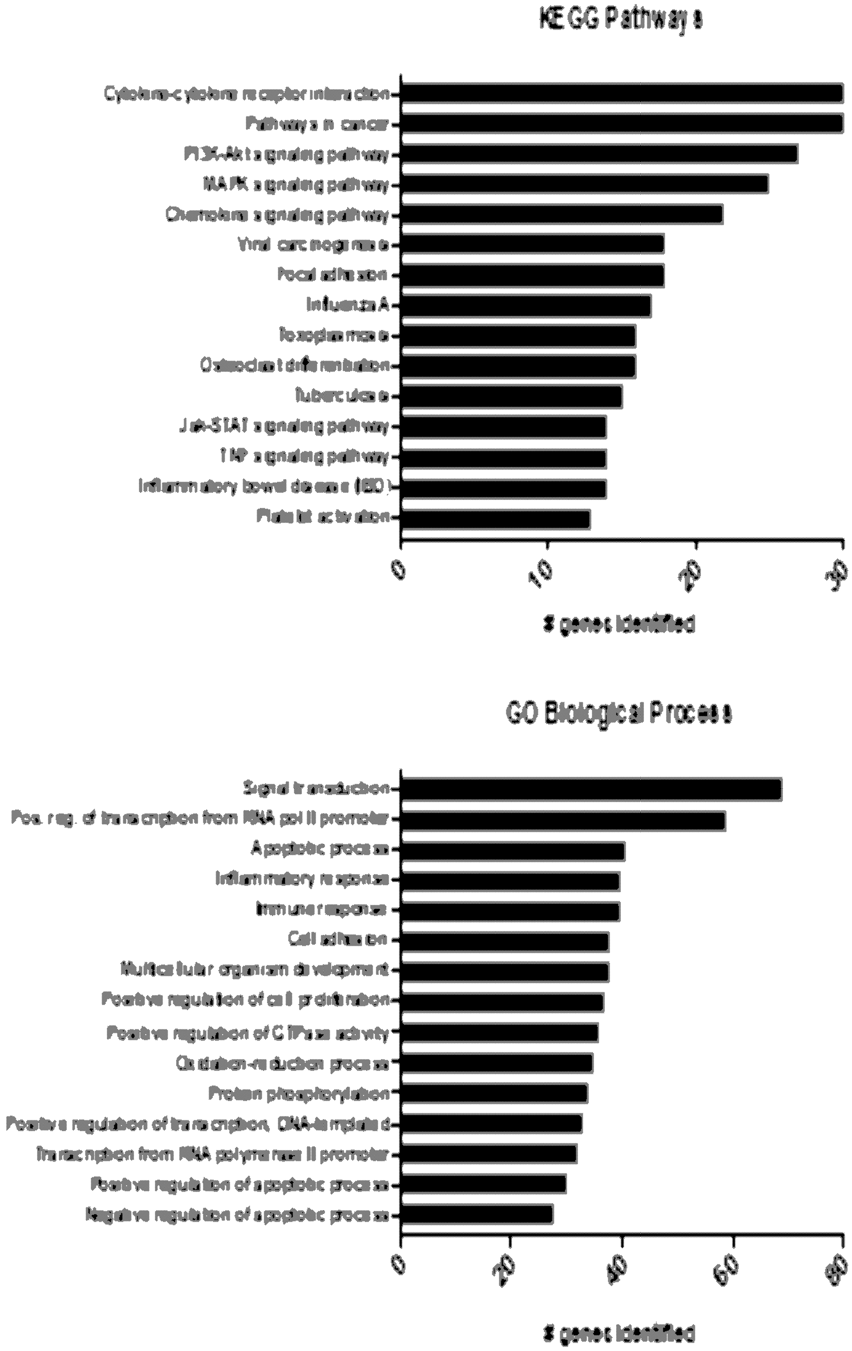
Figure 14A:
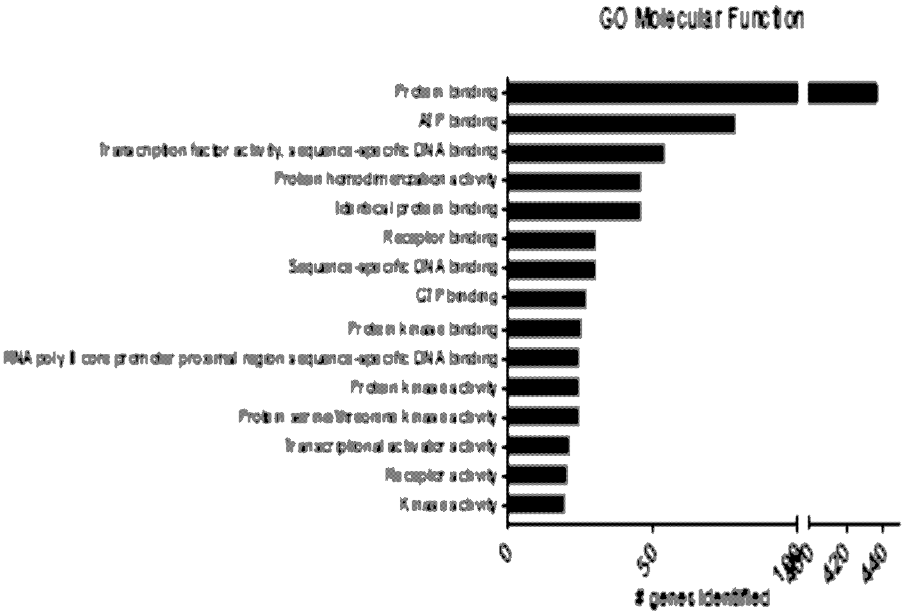
Figure 14A:
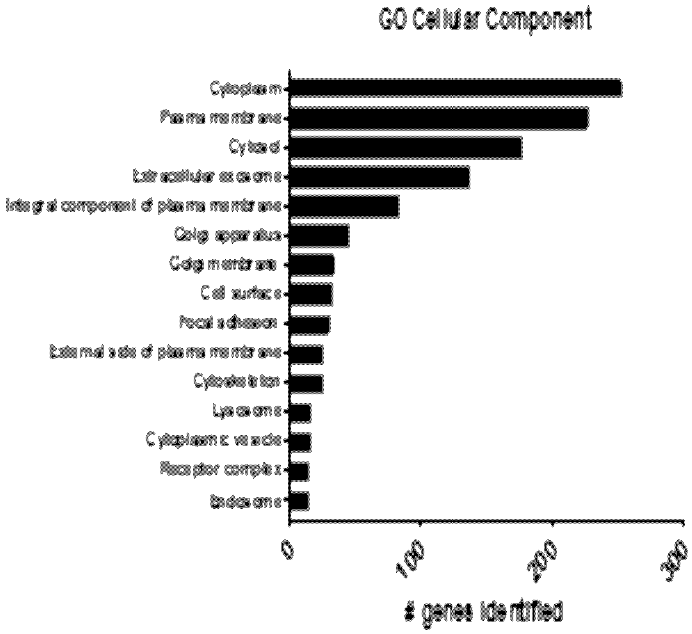

Increased Receptor Affinity Enhances Transcriptional Activity of IL-10 in CD8 T Cells To obtain a more complete understanding of how IL-10 regulates CD8 T cells responses, we next performed transcriptional studies on CD8 T cell treated with the different IL-10 ligands. Human CD8 T cells were purified by positive selection and activated in the presence of IL-10 wt and variants over 6 days as shown in FIG. 6A. The transcriptional changes induced by WTD in CD8 T cells were less dramatic than those induced by this cytokine in monocytes. Only 1000 genes were significantly regulated, with 79% of those genes being down-regulated (FIGS. 6B and 6C). The more highly regulated genes are shown in FIG. 7D. KEGG pathway analysis showed that IL-10 regulated genes are involved in cytokine-cytokine receptor interaction (FIG. 14A). Strikingly, we noticed that IL-10 induced the downregulation of genes classically associated with CD8 T cell exhaustion (FIG. 6E). We compared IL-10-regulated genes to a previously published list of exhaustion-specific CD8 T cell genes (Bengsch et al., 2018). We could identify four clusters of exhaustion genes regulated by IL-10. Cluster 1 comprises genes upregulated in both exhausted T cells and in T cells treated with IL-10. Cluster 2, the largest cluster, shows genes which were upregulated in exhausted T cells but downregulated by IL-10 treatment. Cluster 3 represent genes downregulated in exhausted T cells but upregulated by IL-10 treatment and cluster 4 is comprised of genes downregulated in both exhausted T cells and IL-10 treated T cells. A representative sample of regulated genes in each cluster is shown in FIG. 6F. These results suggest that IL-10 may enhance CD8 T cell activities by preventing their exhaustion. Interestingly, we also observed a significant downregulation of IL-2Ra by IL-10 treatment, which was associated with a reduction on expression of classical IL-2 dependent genes, such as IL-13, LIF, SLC1A4, NFIL3, etc (FIGS. 6G and 6H) (Rollings et al., 2018). Our results suggest that IL-10 regulates CD8 cytotoxic activities by limiting their sensitivity to IL-2, which may delay their exhaustion. As with monocytes, sub-saturating doses of WTD differentially affected a subset of genes regulated by IL-10, with the majority of those genes being downregulated by IL-10 treatment (FIG. 6I). Interestingly, at sub-saturating doses WTD failed to regulate classical IL-2 dependent genes like IL-13 and LIF, suggesting that regulation of IL-2 activities by IL-10 requires high IL-10 doses (FIG. 6J).

Figure 6K:
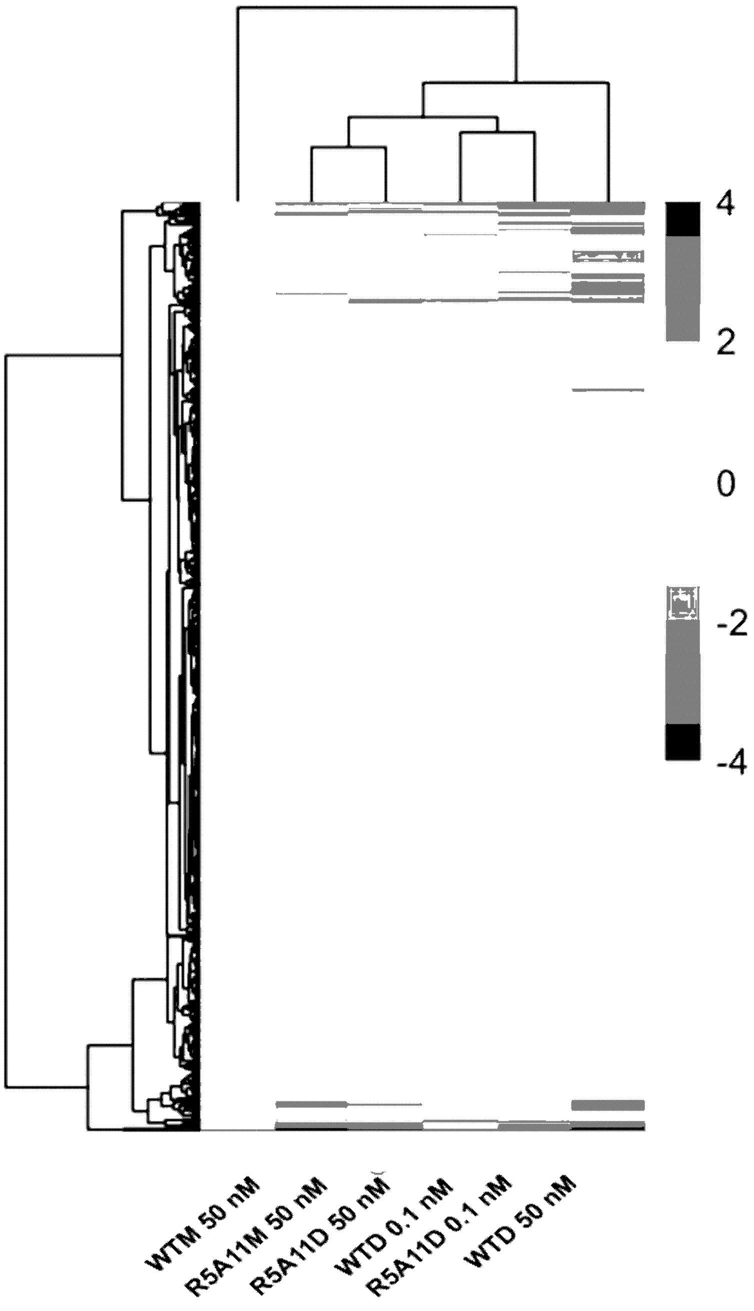
Figure 6L:
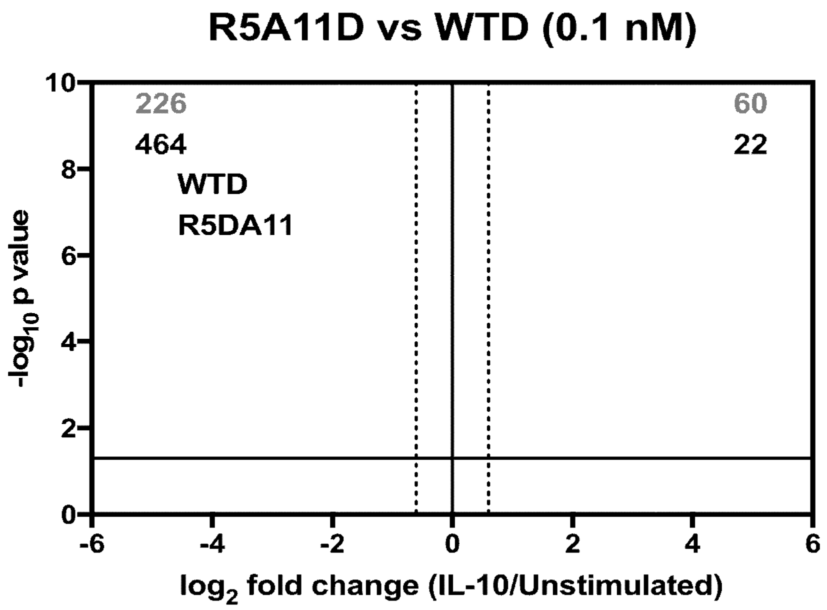
Figure 6M:
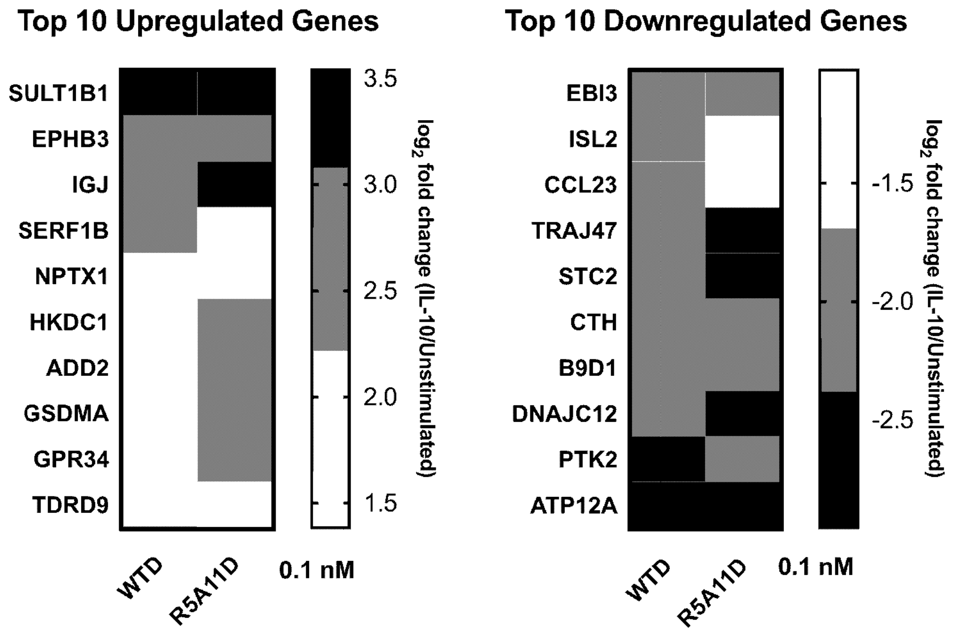
Figure 6N:
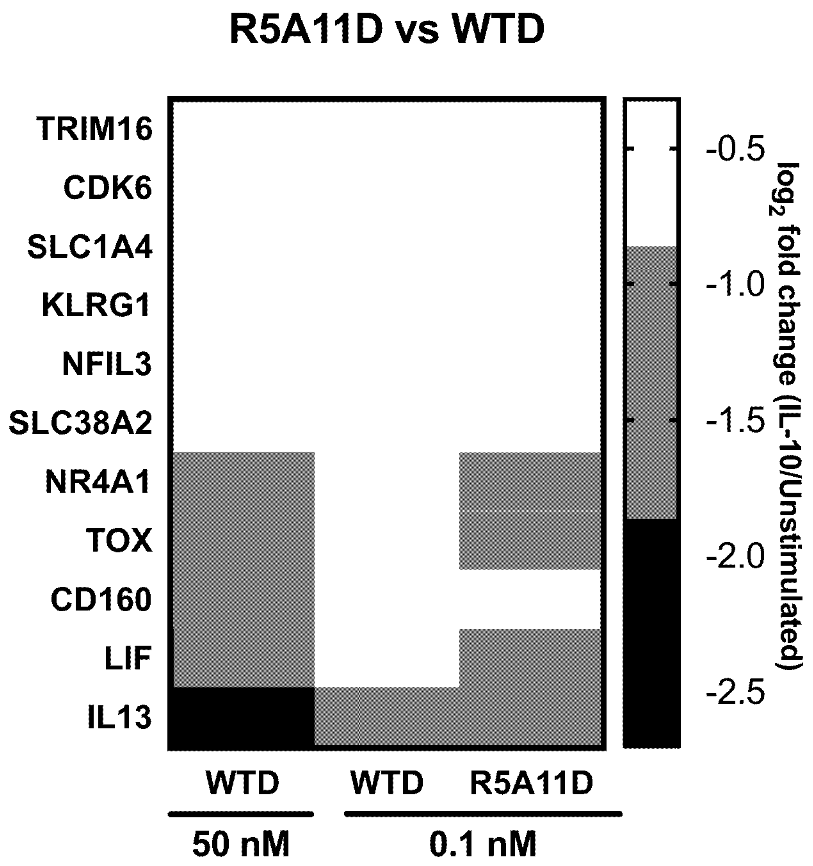
Figure 14B:
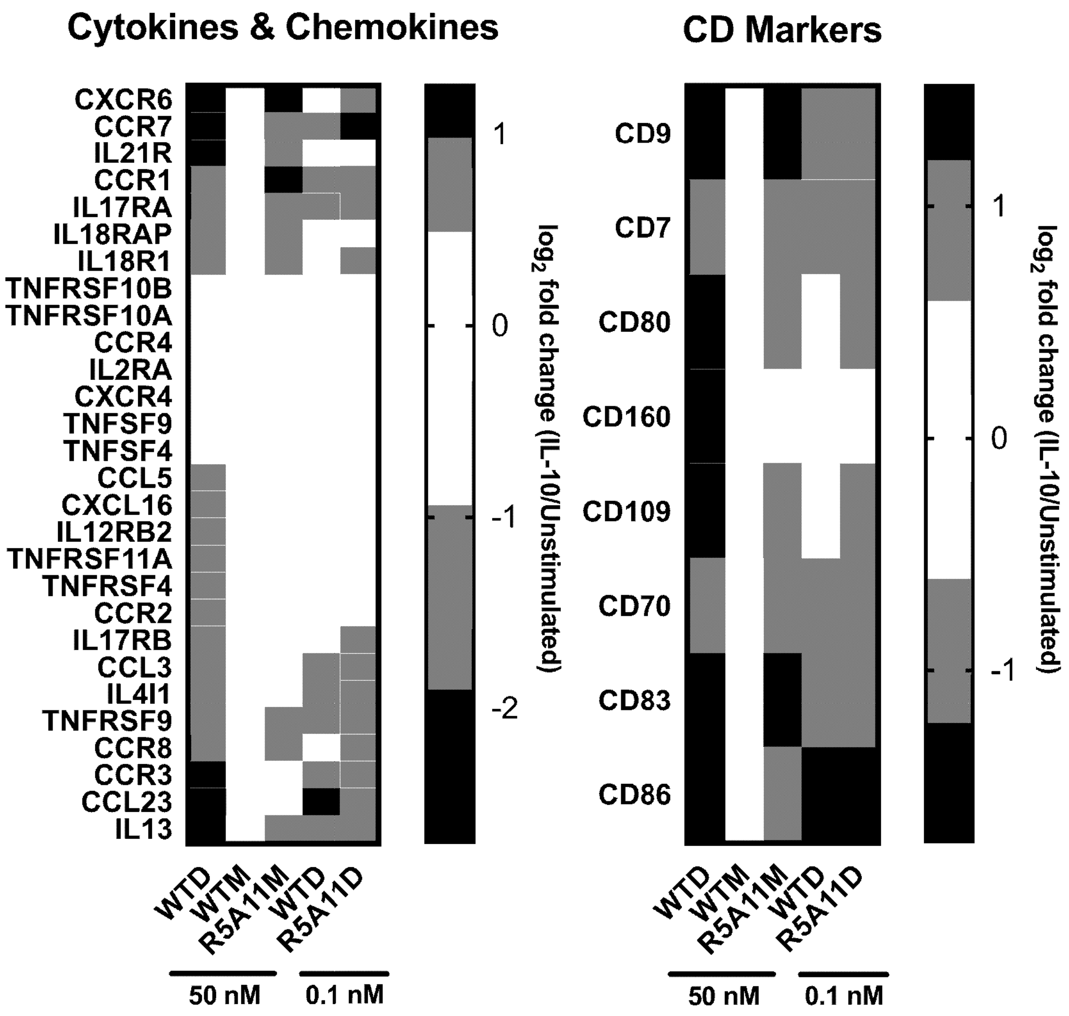
Figure 14B:
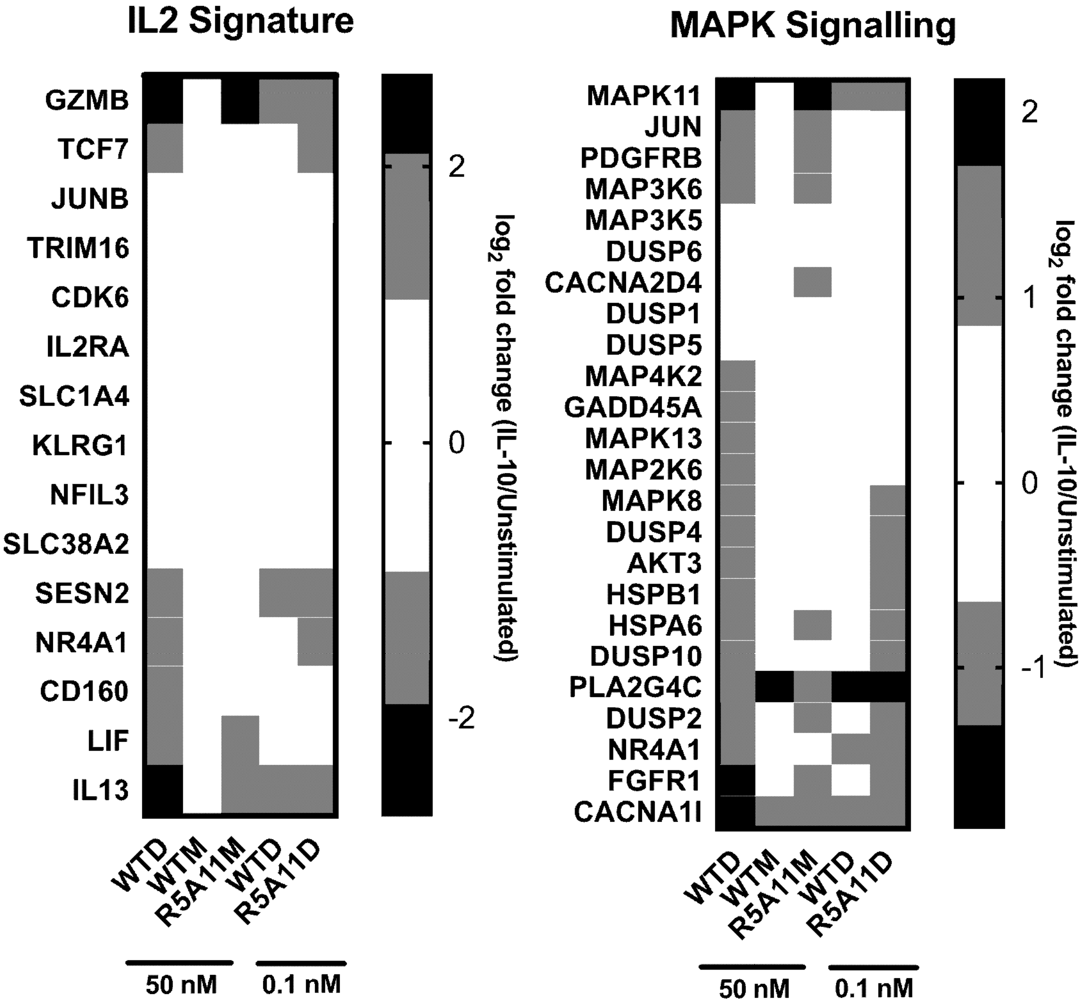
Figure 14C:
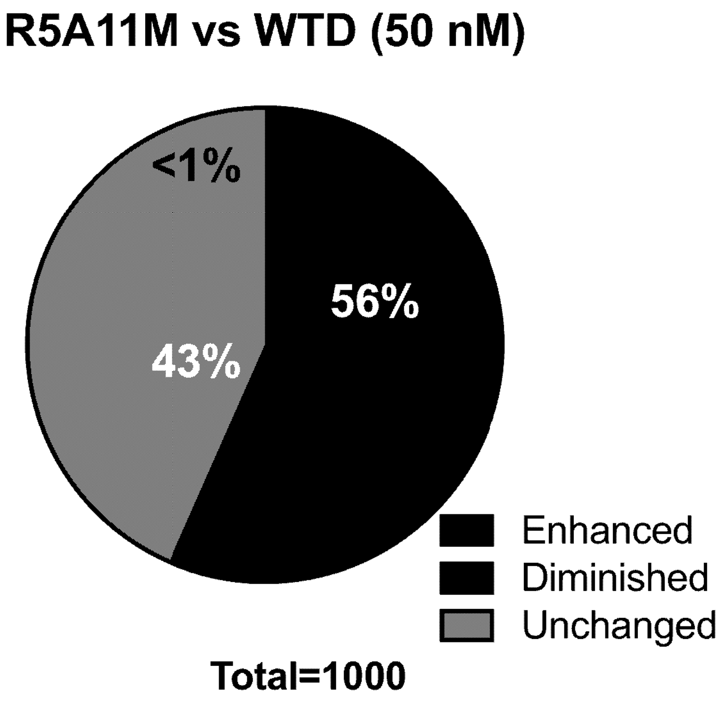
Figure 14D:
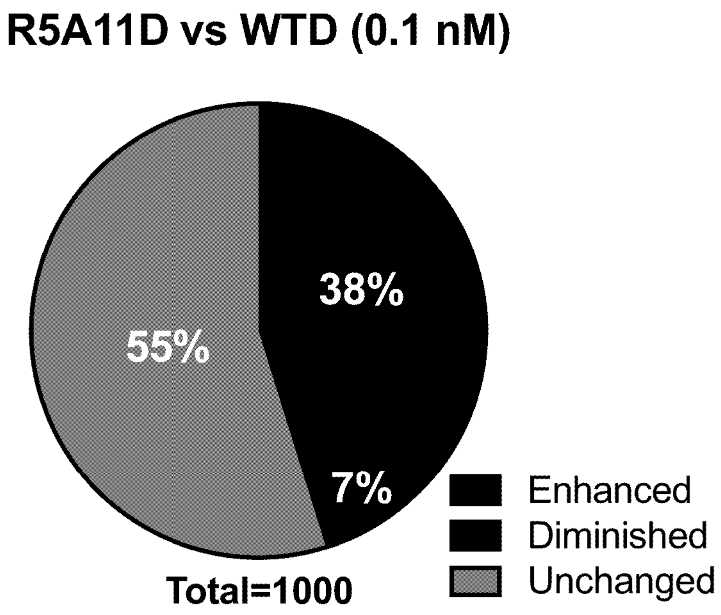

As seen for monocytes, WTM showed very poor induction of gene expression (FIG. 6K and FIG. 14B), in line with its sub optimal STAT activation. R5A11M again enhance the transcriptional response when compared to WTM but failed to reach expression levels induced by the dimeric ligands despite activating very similar signalling profiles (FIG. 6K and FIG. 14B). Indeed, when directly comparing expression levels induced by WTD and R5A11M, the high affinity monomer showed diminished activity of 56% of IL-10 regulated genes (FIG. 14C). Similar to the results obtained with monocytes, R5A11D at 0.1 nM clustered with WTD 50 nM, supporting its ability to act effectively at low concentrations (FIG. 6K). When the expression levels induced by WTD and R5A11D at the sub-saturation concentration were compared, we identified 38% of IL-10 regulated genes being enhanced by R5A11D, with only 7% showing favourable expression by WTD at low dose (FIG. 6L and FIG. 14D). This was clearly reflected when the expression of the top 10 up and downregulated genes by WTD and R5A11D at 0.1 nM was compared (FIG. 6M). Importantly, classical IL-2 dependent genes, which were not regulated by WTD at low doses, were still regulated by R5A11D (FIG. 6N). Together our data confirms that IL-10 variants which bind the beta receptor more strongly exhibit more robust activity at a wider range of ligand concentrations and open new avenues to boost IL-10 based anti-cancer immune-therapies.

Figure 7A:
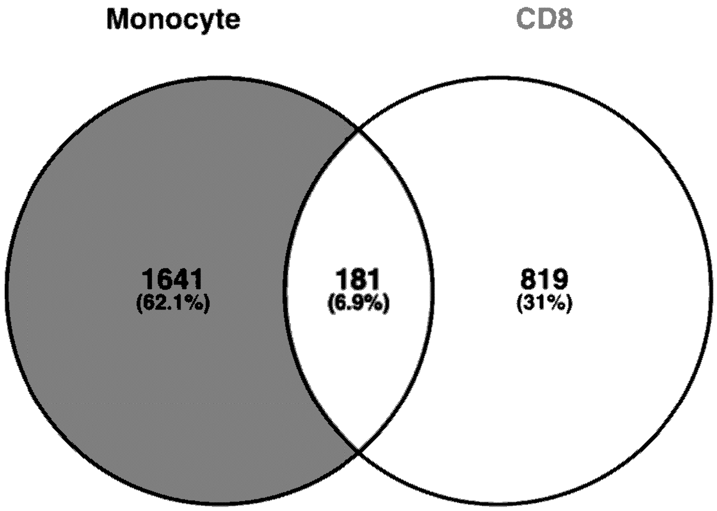
Figure 7B:
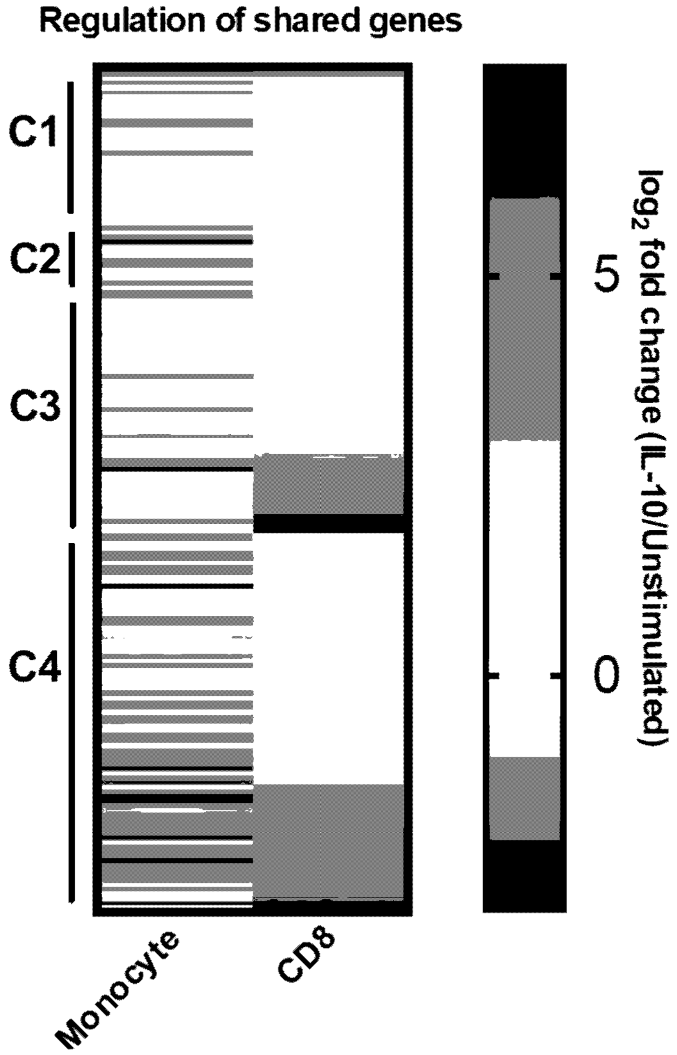
Figure 7C:
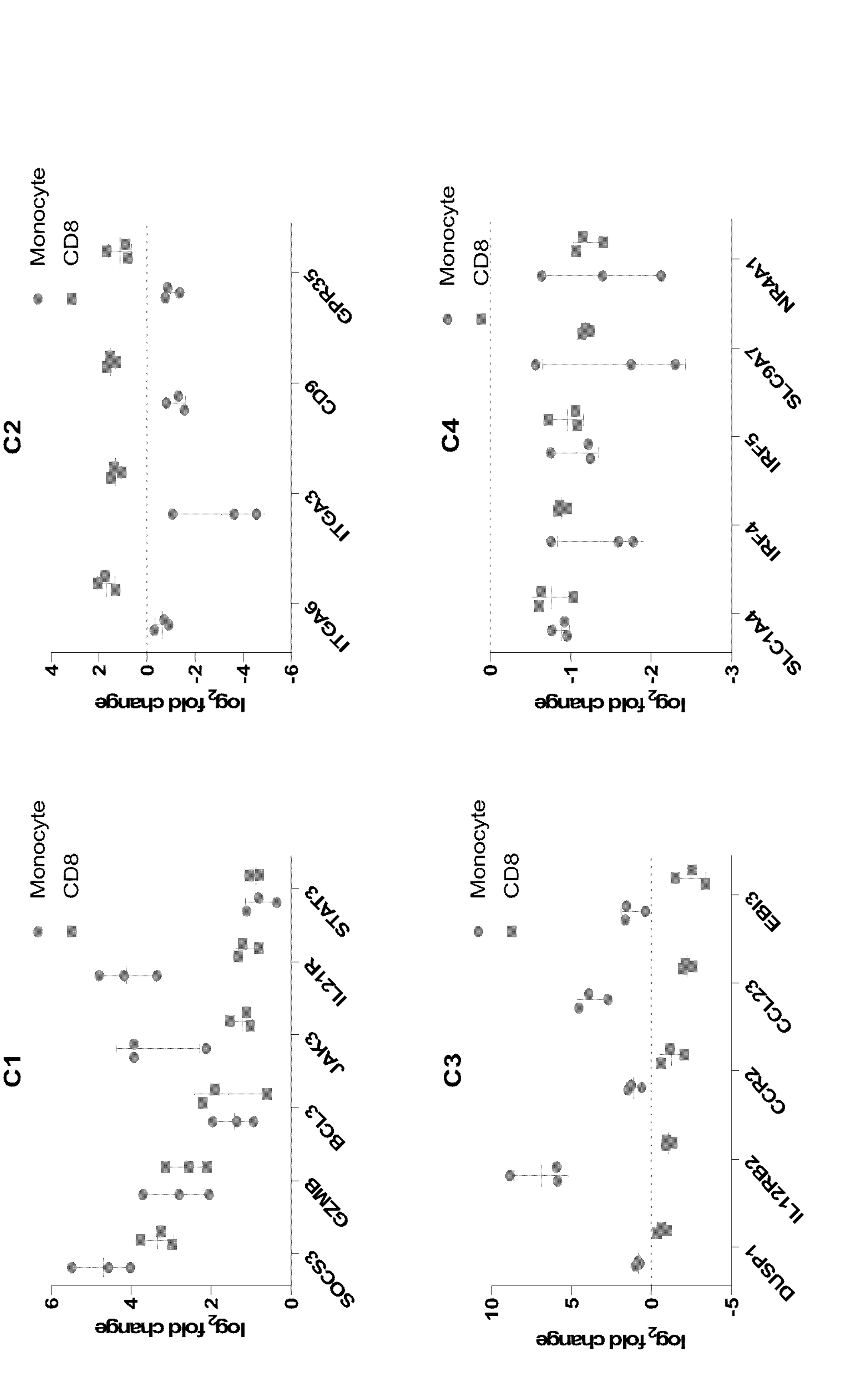

Differential Gene Expression Program Regulated by IL-10 in Monocytes and CD8 T Cells Our study provides a high detailed description of transcriptional changes induced by IL-10 in monocytes and CD8 T cells. Despite the obvious discrepancies in the manner that the two cell types were stimulated with IL-10, we decided to investigate similarities of the transcriptional program induced by IL-10 in the two cell subsets, as a proxy to understand STAT3 transcriptional activities. To minimize variability resulting from the different treatments, we focused on genes that were regulated by IL-10 treatment in both monocytes and CD8 T cells. Interestingly, 181 genes were regulated by IL-10 in monocytes and CD8 T cells (FIG. 7A). We could identify four gene clusters based on their regulation by IL-10 treatment (FIG. 7B). Cluster 1 comprises genes that were upregulated by IL-10 treatment in both monocytes and CD8 T cells (FIG. 7B). Cluster 2 correspond to genes that were downregulated by IL-10 in monocytes, but upregulated by IL-10 in CD8 T cells. Cluster 3 show genes that were upregulated by IL-10 treatment in monocytes and downregulated by IL-10 treatment in CD8 T cells. Cluster 4 comprise genes downregulated by IL-10 treatment in monocytes and CD8 T cells. A representative sample of regulated genes in each cluster is shown in FIG. 7C. Overall our comparative study highlights that although IL-10 induces a shared gene expression program between monocytes and CD8 T cells, whether those IL-10 regulated genes are induced or repressed by IL-10 treatment depend on the context where IL-10 stimulation takes place, providing an additional level of gene regulation by cytokines.

Production of Pentameric IL-10 Mutein and IL-10 Mutein/IL-4 Fusions

Our data have shown that a stabilization of the IL-10/receptor complex results in more potent immuno-modulatory activities by IL-10. Thus, we hypothesize that further stabilizing the IL-10/receptor complex by increasing the binding valency of IL-10 would result in a significant improvement on the activities induced by this ligand. For that, we took advantage of the pentameric BTB domain from KCTD protein to engineer a fusion protein comprised of the pentameric BTB domain and the monomeric R5A11 (Fig. X and Seq. ID. Y). We have recombinantly expressed high levels of this chimeric protein proving the feasibility of the approach (Figure X).

There are very few anti-inflammatory ligands described in the literature. One of them is IL-10, which we have engineered in this invention. An additional anti-inflammatory cytokine is IL-4. Here we have hypothesized that a synthetic cytokines comprising these two molecules would have exceptional anti-inflammatory properties. For that we have used our monomeric high affinity IL-10 variant as a scaffold and fuse it to three different IL-4 variants. IL-4 variant 1 correspond to the wild type molecule. IL-4 variant 2 correspond to an IL_4 variant that does not bind Gc or IL-13Ra1 and act as an antagonist. Variant 3 correspond to an IL-4 variant that exhibits reduced affinity for IL-4Ra. We expect that these mutations will affect the biodistribution of the synthetic molecules and target them to interesting immune cell subsets.

IL-10 in CART Cancer Therapy

Figure 16B:
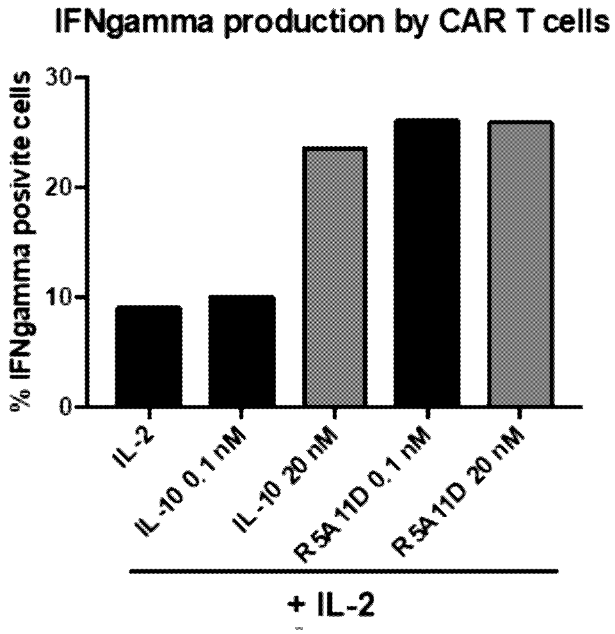

Our data support a positive role of IL-10 in boosting CD8 T cell cytotoxic activities. IL-10 treatment induced the upregulation of Granzyme B by CD8 T cells and reduced their exhaustion gene signature, overall increasing the fitness. Based on this findings we next decided to explore the potential use of IL-10 to enhance CAR T cell therapies. CAR T cells are T cells that have been engineered to express an artificial receptor that allow them to specifically target tumor cells of interest. In recent years this therapy have shown a lot of potential and have revolutionized cancer immunotherapy. However, CAR T cells still suffer from some drawbacks that reduce their efficacy, including the exhaustion of engineered CAR T cells due to over activation. Incubating CAR T cells with IL-10 before the administration to the patient could improve their fitness and therefore enhance their tumor killing potential. Here we provide some preliminary results that support this hypothesis. CAR T cells treated with either IL-10 wt or our engineered IL-10 variant (R5A11) show stronger killing activity in vitro (FIG. 16A) and higher induction of IFNgamma, a classical cytotoxic cytokine (FIG. 16B). Moreover our high affinity variant showed a stronger effect than IL-10 wt, highlighting again that enhance affinity for IL-10Rb boost IL-10 immuno-activities potency.

Discussion:

IL-10 is an important immuno-modulatory cytokine that regulates inflammatory responses and enhances CD8 T cells cytotoxic activities (Moore et al., 2001; Oft, 2014; Walter, 2014). Despite its central role preserving immune homeostasis, there is still a dearth of knowledge of the exact molecular mechanisms through which IL-10 carries out its functions. We postulate that the weak binding affinity that IL-10 exhibits for IL-10Rβ critically contributes to its functional fitness, by limiting the range of concentrations at which IL-10 elicits its full immuno-modulatory potential. Here we have engineered IL-10 to enhance its affinity for IL-10Rβ to investigate whether the stability of the IL-10 receptor complex determines IL-10 bioactivity potencies. Two main findings arise from our study: (1) Affinity-enhanced IL-10 variants trigger more robust responses at a wide range of ligand concentrations and in different immune cell subsets than wildtype IL-10, and (2) the stoichiometry of the IL-10-receptor complex contributes to IL-10 bioactivity potencies beyond regulation of STAT activation levels. More generally, this work outlines a strategy to improve the potency of low receptor binding affinity cytokines and presents new molecular and cellular data with the potential to revitalise failed IL-10 therapies.

IL-10 exerted a profound regulation of the monocytic transcriptional program in our studies, agreeing with previous observations (Moore et al., 2001). IL-10 treatment inhibited antigen presentation by monocytes, limited their ability to recruit inflammatory immune cell subsets through regulation of chemokines and chemokine receptor expression, and boosted their phagocytic activity through the upregulation of scavenger receptors such as CD93, CD47, CD163 and cytokine receptors such as IL-21Ra. In addition, IL-10 treatment modulated the metabolic activity of monocytes by altering their glycolytic and lipid biosynthesis potential, in line with recent studies (Ip et al., 2017). Interestingly, IL-10 effects were slightly biased towards gene repression, with 59% of genes regulated by IL-10 being downregulated. Indeed, several studies have reported the ability of STAT3 to inhibit transcription induced by other STATs (Costa-Pereira et al., 2002; Ray et al., 2014; Yang et al., 2011), suggesting that STAT3 activating cytokines may elicit their functions by disrupting transcriptional programs induced by other cytokines. In agreement with this model, we recently reported that IL-6, another STAT3 activating cytokine, promoted strong STAT3 binding to chromatin, but poor gene expression (Martinez-Fabregas et al., 2019).

The vast majority of reports in the literature describing IL-10 activities have focused on myeloid cells and use a single dose of IL-10, often at saturation (de Waal Malefyt et al., 1991a; Ding et al., 1993; Fiorentino et al., 1991a). However, we have a poor understanding regarding the range of IL-10 doses at which this cytokine elicits a full response in myeloid cells, a critical aspect when considering translation of this cytokine to the clinic. Here we provide transcriptional data from monocytes stimulated with two different doses of IL-10, one saturating and the second sub-saturating, with the latter more closely resembling the doses achieved during IL-10 therapies (Naing et al., 2018). Interestingly, 27% of genes regulated by IL-10 were affected when sub-saturating doses of IL-10 were used. The vast majority of affected genes (95%) were genes downregulated by IL-10 and encoded proteins critically contributing to establish an inflammatory environment i.e. key chemokines and cytokines such as IL-24, CXCL10, CXCL11, CCL22. This data suggests that IL-10 anti-inflammatory activities specifically require high and sustained doses to reach their full effect, explaining in part the failing of IL-10 therapies. Our engineered IL-10 variant exhibited a more robust activity at sub-saturating doses and induced potent inhibition of pro-inflammatory chemokines and cytokines, i.e. IL-24, CXCL10, CXCL11, CCL22. It is thus tempting to speculate that our engineered variant could rescue failed IL-10 therapies by promoting anti-inflammatory activities at low ligand doses.

The anti-inflammatory activities elicited by IL-10 and its effects on monocytes and macrophages are very well documented. How IL-10 regulates the activity of CD8 T cells on the other hand is less clear and more controversial (Oft, 2014). While some studies have reported that IL-10 enhances the function of CD8 T cells and their ability to kill tumour cells (Emmerich et al., 2012), others report that the presence of IL-10 in the tumour microenvironment predicts poor responses by inhibiting T cell activation (Zhao et al., 2015). Our results agree with a positive effect of IL-10 treatment in CD8 T cells cytotoxic activities. CD8 T cells stimulated in the presence of IL-10 exhibited enhanced levels of effector molecules such as granzyme B, agreeing with recent clinical trials that show an improvement in the tumour response of patients treated with Pegylated-IL-10 (Naing et al., 2019). However, the molecular bases by which IL-10 boosts the anti-tumour CD8 T cell response remains poorly defined. Our transcriptional studies highlighted that CD8 T cells stimulated with IL-10 exhibited a reduced exhaustion gene signature and were more functionally fit. IL-10 treated CD8 T cells also expressed lower levels of IL-2Ra, which correlated with a reduced IL-2 gene signature in these cells. Altogether, our data agree with a model where IL-10, by reducing the sensitivity of CD8 T cells to IL-2, may prevent their over-activation and decrease their transition towards an exhausted phenotype. Remarkably, IL-10 preferentially repressed gene expression in CD8 T cells, with 79% of the genes controlled by IL-10 being downregulated, suggesting that STAT3 activation by IL-10 may compete with other STATs for binding to relevant gene promoters, fine-tuning CD8 T cell responses. Indeed, previous studies have reported a competition between STAT3 and STAT5 proteins for binding to gene promoters that influence cell sensitivity to IL-2 and inflammation (Yang et al., 2011). Our engineered IL-10 variant outperformed IL-10 wildtype in every read out tested when sub-saturating doses were used, reproducing our observations in monocytes and highlighting its potential to boost anti-tumour responses at therapeutical doses.

The importance of the dimeric IL-10 architecture for generating its biological responses is not yet well understood. WTD binds IL-10Rα 60-fold more avidly than WTM, which contributes to its more efficient recruitment of IL-10Rβ to the signaling complex and its more potent activities (ref). Paradoxically, R5A11M, which binds IL-10Rβ with higher affinity and elicits more efficient receptor assembly than WTD, triggers weaker transcriptional responses, despite activating STATs to a very similar extent than WTD. In addition, viral IL-10 (also a dimeric ligand) induces the same specific activity than WTD even though binds IL-10Rα with lower affinity than WTM (Tan et al., 1993). Overall these observations suggest that in addition to receptor binding affinity, the stoichiometry of the IL-10-receptor complex contributes to fine-tune IL-10 bioactivity potencies. We recently showed that the number of phosphotyrosines available in cytokine receptor intracellular domains critically contribute to defining signalling identity by cytokines (Martinez-Fabregas et al., 2019). IL-6 variants that triggered partial phosphorylation of Tyr available in the gp130 intracellular domain exhibited a biased STAT3 versus STAT1 activation (Martinez-Fabregas et al., 2019). A similar model could be invoked to explain functional differences between monomeric and dimeric IL-10 ligands. The dimeric IL-10 variants engage two molecules of IL-10Rα and IL-10Rβ, providing twice as many Tyr available for phosphorylation than the monomeric ligands. This in turn would result in an increase local concentration of phosphorylated Tyr that potentially could engaged additional signaling molecules not recruited by the monomeric ligands, and provide functional specificity. In agreement with this model, WTM and R5A11M elicited biased STAT3 activation in CD8 T cells. Future studies will need to address whether the higher number of Tyr available in the hexameric complex engaged by WTD contribute to define its signaling signature and biological identity.

Our study provides a detailed description of how sub-optimal concentrations of IL-10, such as the one achieved during therapeutic interventions, differentially affects IL-10 immuno-modulatory properties. As concentrations of IL-10 decrease critical anti-inflammatory activities induced by this cytokine are lost. IL-10 therapies have been administrated to patients with a wide range of inflammatory disorders, but for the most part only produced disappointing results (Buruiana et al., 2010; Colombel et al., 2001). It is believed that local concentrations of IL-10 reached in the affected tissues during therapies are too low to trigger adequate anti-inflammatory responses (Buruiana et al., 2010; Colombel et al., 2001). In addition, the levels of IL-10 receptor significantly change across different myeloid cell populations, altering their sensitivity to IL-10 and possibly contributing to the poor responses observed in IL-10 therapies (Ding et al., 2001). Importantly, administration of IL-10 is well tolerated by patients, with only some mild side effects when high doses of IL-10 are used (Buruiana et al., 2010; Colombel et al., 2001). Our high affinity IL-10 variant has the potential to overcome these limitations and reinvigorate IL-10 therapies by eliciting strong anti-inflammatory and anti-cancer responses at therapeutically relevant doses, for example 100 μM-10 nM.

REFERENCES

BENGSCH, B., OHTANI, T., KHAN, O., SETTY, M., MANNE, S., O'BRIEN, S., GHERARDINI, P. F., HERATI, R. S., HUANG, A. C., CHANG, K. M., NEWELL, E. W., BOVENSCHEN, N., PE'ER, D., ALBELDA, S. M. & WHERRY, E. J. 2018. Epigenomic-Guided Mass Cytometry Profiling Reveals Disease-Specific Features of Exhausted CD8 T Cells. *Immunity,* 48, 1029-1045 e5.

BENNETT M L, BENNETT F C, LIDDELOW S A, AJAMI B, ZAMANIAN J L, FERNHOFF N B, MULINYAWE S B, BOHLEN C J, ADIL A, TUCKER A, WEISSMAN I L, CHANG E F, L I G, GRANT G A, HAYDEN GEPHART M G, BARRES B A. New tools for studying microglia in the mouse and human CNS. Proc Natl Acad Sci USA. 2016 Mar. 22; 113(12):E1738-46

BODER, E. T. & WITTRUP, K. D. 1997. Yeast surface display for screening combinatorial polypeptide libraries. *Nat Biotechnol,* 15, 553-7.

BRAAT, H., ROTTIERS, P., HOMMES, D. W., HUYGHEBAERT, N., REMAUT, E., REMON, J. P., VAN DEVENTER, S. J., NEIRYNCK, S., PEPPELENBOSCH, M. P. & STEIDLER, L. 2006. A phase I trial with transgenic bacteria expressing interleukin-10 in Crohn's disease. *Clin Gastroenterol Hepatol,* 4, 754-9.

BURUIANA, F. E., SOLA, I. & ALONSO-COELLO, P. 2010. Recombinant human interleukin 10 for induction of remission in Crohn's disease. *Cochrane Database Syst Rev*, CD005109.

CARDOSO, A., GIL CASTRO, A., MARTINS, A. C., CARRICHE, G. M., MURIGNEUX, V., CASTRO, I., CUMANO, A., VIEIRA, P. & SARAIVA, M. 2018. The Dynamics of Interleukin-10-Afforded Protection during Dextran Sulfate Sodium-Induced Colitis. *Front Immunol,* 9, 400.

CHAO, G., LAU, W. L., HACKEL, B. J., SAZINSKY, S. L., LIPPOW, S. M. & WITTRUP, K. D. 2006. Isolating and engineering human antibodies using yeast surface display. *Nat Protoc,* 1, 755-68.

COLLIN M, BIGLEY V. Human dendritic cell subsets: an update. Immunology. 2018 May; 154(1):3-20.

COLOMBEL, J. F., RUTGEERTS, P., MALCHOW, H., JACYNA, M., NIELSEN, O. H., RASK-MADSEN, J., VAN DEVENTER, S., FERGUSON, A., DESREUMAUX, P., FORBES, A., GEBOES, K., MELANI, L. & COHARD, M. 2001. Interleukin 10 (Tenovil) in the prevention of postoperative recurrence of Crohn's disease. *Gut,* 49, 42-6.

CORREA, I., VENY, M., ESTELLER, M., PIQUE, J. M., YAGUE, J., PANES, J. & SALAS, A. 2009. Defective IL-10 production in severe phenotypes of Crohn's disease. *J Leukoc Biol,* 85, 896-903.

COSTA-PEREIRA, A. P., TININININI, S., STROBL, B., ALONZI, T., SCHLAAK, J. F., IS'HARC, H., GESUALDO, I., NEWMAN, S. J., KERR, I. M. & POLI, V. 2002. Mutational switch of an IL-6 response to an interferon-gamma-like response. *Proc Natl Acad Sci USA,* 99, 8043-7.

DALLAGI, A., GIROUARD, J., HAMELIN-MORRISSETTE, J., DADZIE, R., LAURENT, L., VAILLANCOURT, C., LAFOND, J., CARRIER, C. & REYES-MORENO, C. 2015. The activating effect of IFN-gamma on monocytes/macrophages is regulated by the LIF-trophoblast-IL-10 axis via Stat1 inhibition and Stat3 activation. *Cell Mol Immunol,* 12, 326-41

DE WAAL MALEFYT, R., ABRAMS, J., BENNETT, B., FIGDOR, C. G. & DE VRIES, J. E. 1991a. Interleukin 10 (IL-10) inhibits cytokine synthesis by human monocytes: an autoregulatory role of IL-10 produced by monocytes. *J Exp Med,* 174, 1209-20.

DE WAAL MALEFYT, R., HAANEN, J., SPITS, H., RONCAROLO, M. G., T E VELDE, A., FIGDOR, C., JOHNSON, K., KASTELEIN, R., YSSEL, H. & D E VRIES, J. E. 1991b. Interleukin 10 (IL-10) and viral IL-10 strongly reduce antigen-specific human T cell proliferation by diminishing the antigen-presenting capacity of monocytes via downregulation of class II major histocompatibility complex expression. *J Exp Med,* 174, 915-24.

DING, L., LINSLEY, P. S., HUANG, L. Y., GERMAIN, R. N. & SHEVACH, E. M. 1993. IL-10 inhibits macrophage costimulatory activity by selectively inhibiting the up-regulation of B7 expression. *J Immunol,* 151, 1224-34.

DING, Y., QIN, L., ZAMARIN, D., KOTENKO, S. V., PESTKA, S., MOORE, K. W. & BROMBERG, J. S. 2001. Differential IL-10R1 expression plays a critical role in IL-10-mediated immune regulation. *J Immunol,* 167, 6884-92.

EMMERICH, J., MUMM, J. B., CHAN, I. H., LAFACE, D., TRUONG, H., MCCLANAHAN, T., GORMAN, D. M. & OFT, M. 2012. IL-10 Directly Activates and Expands Tumor-Resident CD8(+) T Cells without De Novo Infiltration from Secondary Lymphoid Organs. *Cancer Research,* 72, 3570-3581.

FARKAS S, HORNUNG M, SATTLER C, EDTINGER K, STEINBAUER M, ANTHUBER M, SCHLITT H J, HERFARTH H, GEISSLER E K. Blocking MAdCAM-1 in vivo reduces leukocyte extravasation and reverses chronic inflammation in experimental colitis. Int J Colorectal Dis. 2006 January; 21(1):71-8.

FINBLOOM, D. S. & WINESTOCK, K. D. 1995. IL-10 induces the tyrosine phosphorylation of tyk2 and Jak1 and the differential assembly of STAT1 alpha and STAT3 complexes in human T cells and monocytes. *J Immunol,* 155, 1079-90.

FIORENTINO, D. F., ZLOTNIK, A., MOSMANN, T. R., HOWARD, M. & O'GARRA, A. 1991a. IL-10 inhibits cytokine production by activated macrophages. *J Immunol,* 147, 3815-22.

FIORENTINO, D. F., ZLOTNIK, A., VIEIRA, P., MOSMANN, T. R., HOWARD, M., MOORE,

K. W. & O'GARRA, A. 1991b. IL-10 acts on the antigen-presenting cell to inhibit cytokine production by Th1 cells. *J Immunol,* 146, 3444-51.

FRAIETTA, J. A., LACEY, S. F., ORLANDO, E. J., PRUTEANU-MALINICI, I., GOHIL, M., LUNDH, S., BOESTEANU, A. C., WANG, Y., O'CONNOR, R. S., HWANG, W. T., PEQUIGNOT, E., AMBROSE, D. E., ZHANG, C., WILCOX, N., BEDOYA, F., DORFMEIER, C., CHEN, F., TIAN, L., PARAKANDI, H., GUPTA, M., YOUNG, R. M., JOHNSON, F. B., KULIKOVSKAYA, I., LIU, L., XU, J., KASSIM, S. H., DAVIS, M. M., LEVINE, B. L., FREY, N. V., SIEGEL, D. L., HUANG, A. C., WHERRY, E. J., BITTER, H., BROGDON, J. L., PORTER, D. L., JUNE, C. H. & MELENHORST, J. J. 2018. Determinants of response and resistance to CD19 chimeric antigen receptor (CAR) T cell therapy of chronic lymphocytic leukemia. *Nat Med,* 24, 563-571.

GONEN T, GUZEL S, KESKINBORA K H. YKL-40 is a local marker for inflammation in patients with pseudoexfoliation syndrome. Eye (Lond). 2019 May; 33(5):772-776.

HUANG DA, W., SHERMAN, B. T. & LEMPICKI, R. A. 2009a. Bioinformatics enrichment tools: paths toward the comprehensive functional analysis of large gene lists. *Nucleic Acids Res,* 37, 1-13.

HUANG DA, W., SHERMAN, B. T. & LEMPICKI, R. A. 2009b. Systematic and integrative analysis of large gene lists using DAVID bioinformatics resources. *Nat Protoc,* 4, 44-57.

IP, W. K. E., HOSHI, N., SHOUVAL, D. S., SNAPPER, S. & MEDZHITOV, R. 2017. Anti-inflammatory effect of IL-10 mediated by metabolic reprogramming of macrophages. *Science,* 356, 513-519.

ITO, S., ANSARI, P., SAKATSUME, M., DICKENSHEETS, H., VAZQUEZ, N., DONNELLY, R. P., LARNER, A. C. & FINBLOOM, D. S. 1999. Interleukin-10 inhibits expression of both interferon alpha- and interferon gamma-induced genes by suppressing tyrosine phosphorylation of STAT1. *Blood,* 93, 1456-63.

JIN K, LUO Z, ZHANG B, PANG Z. Biomimetic nanoparticles for inflammation targeting. Acta Pharm Sin B. 2018 January; 8(1):23-33.

JOSEPHSON, K., DIGIACOMO, R., INDELICATO, S. R., IYO, A. H., NAGABHUSHAN, T. L., PARKER, M. H., WALTER, M. R. & AYO, A. H. 2000. Design and analysis of an engineered human interleukin-10 monomer. *J Biol Chem,* 275, 13552-7.

KELLY T, HUANG Y, SIMMS A E, MAZUR A. Fibroblast activation protein-α: a key modulator of the microenvironment in multiple pathologies. Int Rev Cell Mol Biol. 2012; 297:83-116.

KIRCHER M, HERHAUS P, SCHOTTELIUS M, BUCK A K, WERNER R A, WESTER H J, KELLER U, LAPA C. CXCR4-directed theranostics in oncology and inflammation. Ann Nucl Med. 2018 October; 32(8):503-511.

KIRCHHOFER, A., HELMA, J., SCHMIDTHALS, K., FRAUER, C., CUI, S., KARCHER, A., PELLIS, M., MUYLDERMANS, S., CASAS-DELUCCHI, C. S., CARDOSO, M. C., LEONHARDT, H., HOPFNER, K. P. & ROTHBAUER, U. 2010. Modulation of protein properties in living cells using nanobodies. *Nature Structural & Molecular Biology,* 17, 133-U162.

KRUTZIK, P. O. & NOLAN, G. P. 2006. Fluorescent cell barcoding in flow cytometry allows high-throughput drug screening and signaling profiling. *Nat Methods,* 3, 361-8.

LAPORTE, S. L., JUO, Z. S., VACLAVIKOVA, J., COLF, L. A., QI, X., HELLER, N. M., KEEGAN, A. D. & GARCIA, K. C. 2008. Molecular and structural basis of cytokine receptor pleiotropy in the interleukin-4/13 system. *Cell,* 132, 259-72.

LEMAŃSKA-PEREK A, ADAMIK B. Fibronectin and its soluble EDA-FN isoform as biomarkers for inflammation and sepsis. Adv Clin Exp Med. 2019 November; 28(11): 1561-1567.

LOGSDON, N. J., JONES, B. C., JOSEPHSON, K., COOK, J. & WALTER, M. R. 2002. Comparison of interleukin-22 and interleukin-10 soluble receptor complexes. *J Interferon Cytokine Res,* 22, 1099-112.

MANNINO, M. H., ZHU, Z., XIAO, H., BAI, Q., WAKEFIELD, M. R. & FANG, Y. 2015. The paradoxical role of IL-10 in immunity and cancer. *Cancer Lett,* 367, 103-7.

MARTINEZ-FABREGAS, J., WILMES, S., WANG, L., HAFER, M., POHLER, E., LOKAU, J., GARBERS, C., COZZANI, A., FYFE, P. K., PIEHLER, J., KAZEMIAN, M., MITRA, S. & MORAGA, I. 2019. Kinetics of cytokine receptor trafficking determine signaling and functional selectivity. *Elife,* 8.

MEJIAS-LUQUE R, LINDÉN S K, GARRIDO M, TYE H, NAJDOVSKA M, JENKINS B J, IGLESIAS M, ERNST M, DE BOLOS C. Inflammation modulates the expression of the intestinal mucins MUC2 and MUC4 in gastric tumors. Oncogene. 2010 Mar. 25; 29(12):1753-62.

MENDOZA, J. L., SCHNEIDER, W. M., HOFFMANN, H. H., VERCAUTEREN, K., JUDE, K. M., XIONG, A., MORAGA, I., HORTON, T. M., GLENN, J. S., DE JONG, Y. P., RICE, C. M. & GARCIA, K. C. 2017. The IFN-λ-IFN-λR1-IL-10Rβ Complex Reveals Structural Features Underlying Type III IFN Functional Plasticity. *Immunity,* 46, 379-392.

MITTAL, S. K. & ROCHE, P. A. 2015. Suppression of antigen presentation by IL-10. *Curr Opin Immunol,* 34, 22-7.

MOORE, K. W., DE WAAL MALEFYT, R., COFFMAN, R. L. & O'GARRA, A. 2001. Interleukin-10 and the interleukin-10 receptor. *Annu Rev Immunol,* 19, 683-765.

MORAGA, I., RICHTER, D., WILMES, S., WINKELMANN, H., JUDE, K., THOMAS, C., SUHOSKI, M. M., ENGLEMAN, E. G., PIEHLER, J. & GARCIA, K. C. 2015a. Instructive roles for cytokine-receptor binding parameters in determining signaling and functional potency. *Science Signaling,* 8.

MORAGA, I., RICHTER, D., WILMES, S., WINKELMANN, H., JUDE, K., THOMAS, C., SUHOSKI, M. M., ENGLEMAN, E. G., PIEHLER, J. & GARCIA, K. C. 2015b. Instructive roles for cytokine-receptor binding parameters in determining signaling and functional potency. *Sci Signal,* 8, ra114.

MORAGA, I., WERNIG, G., WILMES, S., GRYSHKOVA, V., RICHTER, C. P., HONG, W. J., SINHA, R., GUO, F., FABIONAR, H., WEHRMAN, T. S., KRUTZIK, P., DEMHARTER, S., PLO, I., WEISSMAN, I. L., MINARY, P., MAJETI, R., CONSTANTINESCU, S. N.,

PIEHLER, J. & GARCIA, K. C. 2015c. Tuning cytokine receptor signaling by re-orienting dimer geometry with surrogate ligands. *Cell,* 160, 1196-208.
MOUTEL S, BEUGNET A, SCHNEIDER A, LOMBARD B, LOEW D, AMIGORENA S, PEREZ F, SEGURA E. Surface LSP-1 Is a Phenotypic Marker Distinguishing Human Classical versus Monocyte-Derived Dendritic Cells. iScience. 2020 Apr. 24; 23(4):100987
MUMM, J. B., EMMERICH, J., ZHANG, X., CHAN, I., WU, L., MAUZE, S., BLAISDELL, S., BASHAM, B., DAI, J., GREIN, J., SHEPPARD, C., HONG, K., CUTLER, C., TURNER, S., LAFACE, D., KLEINSCHEK, M., JUDO, M., AYANOGLU, G., LANGOWSKI, J., GU, D., PAPORELLO, B., MURPHY, E., SRIRAM, V., NARAVULA, S., DESAI, B., MEDICHERLA, S., SEGHEZZI, W., MCCLANAHAN, T., CANNON-CARLSON, S., BEEBE, A. M. & OFT, M. 2011. IL-10 elicits IFNgamma-dependent tumor immune surveillance. *Cancer Cell,* 20, 781-96.
MUMM, J. B. & OFT, M. 2013. Pegylated IL-10 induces cancer immunity: the surprising role of IL-10 as a potent inducer of IFN-γ-mediated CD8(+) T cell cytotoxicity. *Bioessays,* 35, 623-31.
NAING, A., INFANTE, J. R., PAPADOPOULOS, K. P., CHAN, I. H., SHEN, C., RATTI, N. P., ROJO, B., AUTIO, K. A., WONG, D. J., PATEL, M. R., OTT, P. A., FALCHOOK, G. S., PANT, S., HUNG, A., PEKAREK, K. L., WU, V., ADAMOW, M., MCCAULEY, S., MUMM, J. B., WONG, P., VAN VLASSELAER, P., LEVEQUE, J., TANNIR, N. M. & OFT, M. 2018. PEGylated IL-10 (Pegilodecakin) Induces Systemic Immune Activation, CD8. *Cancer Cell,* 34, 775-791.e3.
NAING, A., WONG, D. J., INFANTE, J. R., KORN, W. M., ALJUMAILY, R., PAPADOPOULOS, K. P., AUTIO, K. A., PANT, S., BAUER, T. M., DRAKAKI, A., DAVER, N. G., HUNG, A., RATTI, N., MCCAULEY, S., VAN VLASSELAER, P., VERMA, R., FERRY, D., OFT, M., DIAB, A., GARON, E. B. & TANNIR, N. M. 2019. Pegilodecakin combined with pembrolizumab or nivolumab for patients with advanced solid tumours (IVY): a multicentre, multicohort, open-label, phase 1b trial. *Lancet Oncol,* 20, 1544-1555.
OFT, M. 2014. IL-10: master switch from tumor-promoting inflammation to antitumor immunity. *Cancer Immunol Res,* 2, 194-9.
OFT, M. 2019. Immune regulation and cytotoxic T cell activation of IL-10 agonists—Preclinical and clinical experience. *Semin Immunol,* 44, 101325.
RAY, J. P., MARSHALL, H. D., LAIDLAW, B. J., STARON, M. M., KAECH, S. M. & CRAFT, J. 2014. Transcription factor STAT3 and type I interferons are corepressive insulators for differentiation of follicular helper and T helper 1 cells. *Immunity,* 40, 367-77.
RHODES J W, TONG O, HARMAN A N, TURVILLE S G. Human Dendritic Cell Subsets, Ontogeny, and Impact on HIV Infection. Front Immunol. 2019 May 16; 10:1088.
ROLLINGS, C. M., SINCLAIR, L. V., BRADY, H. J. M., CANTRELL, D. A. & ROSS, S. H. 2018. Interleukin-2 shapes the cytotoxic T cell proteome and immune environment-sensing programs. *Sci Signal,* 11.
SAXENA, A., KHOSRAVIANI, S., NOEL, S., MOHAN, D., DONNER, T. & HAMAD, A. R. 2015. Interleukin-10 paradox: A potent immunoregulatory cytokine that has been difficult to harness for immunotherapy. *Cytokine,* 74, 27-34.
SAXENA M, BHARDWAJ N. Turbocharging vaccines: emerging adjuvants for dendritic cell based therapeutic cancer vaccines. Curr Opin Immunol. 2017 August; 47:35-43.
SHIGEMORI, S. & SHIMOSATO, T. 2017. Applications of Genetically Modified Immunobiotics with High Immunoregulatory Capacity for Treatment of Inflammatory Bowel Diseases. *Front Immunol,* 8, 22.
SIEW J J, CHEN H M, CHEN H Y, CHEN H L, CHEN C M, SOONG B W, WU Y R, CHANG C P, CHAN Y C, LIN C H, LIU F T, CHERN Y. Galectin-3 is required for the microglia-mediated brain inflammation in a model of Huntington's disease. Nat Commun. 2019 Aug. 2; 10(1): 3473.
SPANGLER, J. B., MORAGA, I., JUDE, K. M., SAWIDES, C. S., AND GARCIA, K. C. (2019). A strategy for the selection of monovalent antibodies that span protein dimer interfaces. J Biol Chem 294, 13876-13886.
STEIDLER, L., HANS, W., SCHOTTE, L., NEIRYNCK, S., OBERMEIER, F., FALK, W., FIERS, W. & REMAUT, E. 2000. Treatment of murine colitis by *Lactococcus lactis* secreting interleukin-10. *Science,* 289, 1352-5.
TAN, J. C., INDELICATO, S. R., NARULA, S. K., ZAVODNY, P. J., AND CHOU, C. C. (1993). Characterization of interleukin-10 receptors on human and mouse cells. J Biol Chem 268, 21053-21059.
WALTER, M. R. 2014. The molecular basis of IL-10 function: from receptor structure to the onset of signaling. *Curr Top Microbiol Immunol,* 380, 191-212.
WEHINGER, J., GOUILLEUX, F., GRONER, B., FINKE, J., MERTELSMANN, R. & WEBER-NORDT, R. M. 1996. IL-10 induces DNA binding activity of three STAT proteins (Stat1, Stat3, and Stat5) and their distinct combinatorial assembly in the promoters of selected genes. *FEBS Lett,* 394, 365-70.
WILLEMS, F., MARCHANT, A., DELVILLE, J. P., GERARD, C., DELVAUX, A., VELU, T., D E BOER, M. & GOLDMAN, M. 1994. Interleukin-10 inhibits B7 and intercellular adhesion molecule-1 expression on human monocytes. *Eur J Immunol,* 24, 1007-9.
WILMES, S., BEUTEL, O., LI, Z., FRANCOIS-NEWTON, V., RICHTER, C. P., JANNING, D., KROLL, C., HANHART, P., HOTTE, K., YOU, C., UZE, G., PELLEGRINI, S. & PIEHLER, J. 2015. Receptor dimerization dynamics as a regulatory valve for plasticity of type I interferon signaling. *J Cell Biol,* 209, 579-93.
WILMES, S., HAFER, M., VUORIO, J., TUCKER, J. A., WINKELMANN, H., LOCHTE, S., STANLY, T. A., PULGAR PRIETO, K. D., POOJARI, C., SHARMA, V., RICHTER, C. P., KURRE, R., HUBBARD, S. R., GARCIA, K. C., MORAGA, I., VATTULAINEN, I., HITCHCOCK, I. S. & PIEHLER, J. 2020. Mechanism of homodimeric cytokine receptor activation and dysregulation by oncogenic mutations. *Science,* 367, 643-652.
YANG, X. P., GHORESCHI, K., STEWARD-THARP, S. M., RODRIGUEZ-CANALES, J., ZHU, J., GRAINGER, J. R., HIRAHARA, K., SUN, H. W., WEI, L., VAHEDI, G., KANNO, Y., O'SHEA, J. J. & LAURENCE, A. 2011. Opposing regulation of the locus encoding IL-17 through direct, reciprocal actions of STAT3 and STAT5. *Nat Immunol,* 12, 247-54.

YAZDANI S, BANSAL R, PRAKASH J. Drug targeting to myofibroblasts: Implications for fibrosis and cancer. Adv Drug Deliv Rev. 2017 Nov. 1; 121:101-116.
YUE, F. Y., DUMMER, R., GEERTSEN, R., HOFBAUER, G., LAINE, E., MANOLIO, S. & BURG, G. 1997. Interleukin-10 is a growth factor for human melanoma cells and down-regulates HLA class-I, HLA class-II and ICAM-1 molecules. *Int J Cancer,* 71, 630-7.
ZHAO, S., WU, D., WU, P., WANG, Z. & HUANG, J. 2015. Serum IL-10 Predicts Worse Outcome in Cancer Patients: A Meta-Analysis. *PLoS One,* 10, e0139598.
ZHU, L., SHI, T., ZHONG, C., WANG, Y., CHANG, M. & LIU, X. 2017. IL-10 and IL-10 Receptor Mutations in Very Early Onset Inflammatory Bowel Disease. *Gastroenterology Res,* 10, 65-69.

The invention claimed is:

1. An IL-10 mutein, wherein the IL-10 mutein comprises substitutions of 1 to 10 amino acids comprising at least one amino acid substitution at positions 18, 92 and 99, as compared to full-length wild-type IL-10 (SEQ ID NO: 1), and does not contain any additional substitutions, wherein numbering is with respect to the wild-type IL-10 sequence shown in SEQ ID NO: 1, but excluding the signal peptide sequence which constitutes the first 18 amino acid residues in SEQ ID NO: 1.

2. The IL-10 mutein according to claim 1, wherein the IL-10 mutein comprises at least two amino acid substitutions at positions 18, 92 and 99.

3. The IL-10 mutein according to claim 1, wherein the IL10 mutein comprises amino acid substitutions at all three positions, 18, 92 and 99.

4. The IL-10 mutein according to claim 1, comprising a substitution at position 18 and the substitution is Y or I.

5. The IL-10 mutein according to claim 1, comprising a substitution at position 92 and the substitution is I.

6. The IL-10 mutein according to claim 1, comprising a substitution at position 99 and the substitution is N.

7. The IL-10 mutein according to claim 1, wherein the IL-10 mutein comprises one or more substitutions at positions 55, 69, 97, 110, 111 and/or 148, and wherein numbering is with respect to the wild-type IL-10 sequence shown in SEQ ID NO: 1, but excluding the signal peptide sequence which constitutes the first 18 amino acid residues in SEQ ID NO: 1.

8. The IL-10 mutein according to claim 1, wherein the IL-10 mutein is at least 97, 98%, 99% or 100% identical to the sequence according to SEQ ID NO:5, 7, 11 or 15, but comprises at least the amino acid substitutions identified in SEQ ID NO:5, 7, 11 or 15, which differ with respect to the corresponding wild-type IL-10 sequence (SEQ ID NO: 1).

9. The IL-10 mutein according to claim 1, wherein the IL-10 mutein is further modified by PEGylation, phosphorylation, amidation and/or glycosylation.

10. A pharmaceutical composition comprising the IL-10 mutein according to claim 1, together with a pharmaceutically acceptable excipient.

11. The IL-10 mutein according to claim 1, wherein the IL-10 mutein binds to IL-10Rβ with a Kd which is 100-fold lower compared to the binding of wild type IL-10 to IL-10Rβ.

12. The IL-10 mutein according to claim 1, wherein the IL-10 mutein forms a dimer.

13. The IL-10 mutein according to claim 8, wherein the IL-10 mutein is further modified by PEGylation, phosphorylation, amidation and/or glycosylation.

14. A pharmaceutical composition comprising the IL-10 mutein according to claim 8, together with a pharmaceutically acceptable excipient.

15. The IL-10 mutein according to claim 8, wherein the IL-10 mutein binds to IL-10Rβ with a Kd which is 100-fold lower compared to the binding of wild type IL-10 to IL-10Rβ.

16. The IL-10 mutein according to claim 8, wherein the IL-10 mutein forms a dimer.

* * * * *